US011668713B2

(12) United States Patent
Chiu et al.

(10) Patent No.: US 11,668,713 B2
(45) Date of Patent: Jun. 6, 2023

(54) SYSTEMS AND METHODS FOR CYCLIC FLUORESCENCE IMAGING

(71) Applicant: University of Washington, Seattle, WA (US)

(72) Inventors: Daniel T. Chiu, Seattle, WA (US); Chun-Ting Kuo, Seattle, WA (US); Li Wu, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 584 days.

(21) Appl. No.: 16/347,502

(22) PCT Filed: Nov. 16, 2017

(86) PCT No.: PCT/US2017/062104
§ 371 (c)(1),
(2) Date: May 3, 2019

(87) PCT Pub. No.: WO2018/094113
PCT Pub. Date: May 24, 2018

(65) Prior Publication Data
US 2020/0057060 A1    Feb. 20, 2020

Related U.S. Application Data

(60) Provisional application No. 62/422,956, filed on Nov. 16, 2016.

(51) Int. Cl.
*G01N 33/554*    (2006.01)
*G01N 33/533*    (2006.01)
(Continued)

(52) U.S. Cl.
CPC ...... *G01N 33/554* (2013.01); *B01L 3/502715* (2013.01); *G01N 15/1484* (2013.01);
(Continued)

(58) Field of Classification Search
CPC ............. G01N 33/554; G01N 21/6458; G01N 2021/6432; G01N 33/533
See application file for complete search history.

(56) References Cited

U.S. PATENT DOCUMENTS 5,215,883 A * 6/1993 Chu ..................... G01N 27/447
                                                        204/452
2008/0118916 A1    5/2008 Sood et al.
(Continued)

FOREIGN PATENT DOCUMENTS

CN        101971029 A       2/2011
CN        102539506 A       7/2012
(Continued)

OTHER PUBLICATIONS

International Search Report and Written Opinion dated Mar. 7, 2018, issued in corresponding Application No. PCT/US2017/062104, filed Nov. 16, 2017, 10 pages.
(Continued)

*Primary Examiner* — Gailene Gabel
(74) *Attorney, Agent, or Firm* — Christensen O'Connor Johnson Kindness PLLC

(57) ABSTRACT

Methods and systems for improved labeling and/or de-labeling a molecule or cell in the context of scientific experimentation, industrial applications, and clinical investigation, including the means to repeat the process of labeling and de-labeling in an efficient manner.

16 Claims, 22 Drawing Sheets

(51) Int. Cl.
*B01L 3/00* (2006.01)
*G01N 15/14* (2006.01)
*G01N 21/64* (2006.01)

(52) U.S. Cl.
CPC ..... *G01N 21/6428* (2013.01); *G01N 21/6452* (2013.01); *G01N 21/6458* (2013.01); *G01N 33/533* (2013.01); *B01L 2300/047* (2013.01); *B01L 2300/06* (2013.01); *B01L 2300/0627* (2013.01); *B01L 2300/0819* (2013.01); *B01L 2300/0883* (2013.01); *B01L 2300/18* (2013.01); *G01N 2021/6432* (2013.01)

(56) References Cited

U.S. PATENT DOCUMENTS

| | | | |
|---|---|---|---|
| 2012/0034157 A1 | 2/2012 | Hyde et al. | |
| 2012/0123109 A1 | 5/2012 | Diwu et al. | |
| 2012/0282632 A1 | 11/2012 | Chiu et al. | |
| 2012/0288865 A1* | 11/2012 | Sundberg | C12Q 1/6862 435/6.12 |
| 2012/0329665 A1 | 12/2012 | Rimm et al. | |
| 2014/0274746 A1* | 9/2014 | Khurana | C12Q 1/6874 506/3 |
| 2015/0316482 A1* | 11/2015 | Natarajan | G01N 33/5306 506/9 |

FOREIGN PATENT DOCUMENTS

| | | |
|---|---|---|
| CN | 103201630 A | 7/2013 |
| CN | 104114713 A | 10/2014 |
| CN | 104620107 A | 5/2015 |
| CN | 104955958 A | 9/2015 |
| CN | 105586403 A | 5/2016 |
| EP | 2042861 A2 | 4/2009 |
| JP | 2009085634 A | 4/2009 |
| JP | 2009525759 A | 7/2009 |

OTHER PUBLICATIONS

Extended European Search Report dated May 19, 2020, issued in European Application No. EP17872573.5, filed Nov. 16, 2017, 8 pages.
First Office Action dated Feb. 7, 2021, for Chinese Patent Application No. 201780083120.4, with English translation, 33 pages.
Japanese Office Action dated Dec. 13, 2021, issued in JP Application No. 20190547251 filed on Jul. 4, 2019, 13 pages.

* cited by examiner 5 min 60 min 120 min

37°C, 5min

10xC, 5min

37°C +10xC(SCS), 5min

A) PE-anti-EpCAM

B) PE-anti-Cytokeratine

FIG. 13A  FIG. 13B  FIG. 13C  FIG. 13D  FIG. 13E
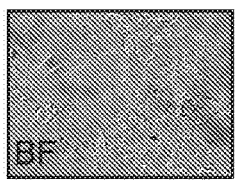 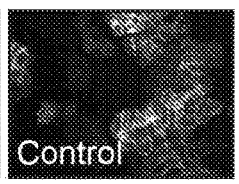 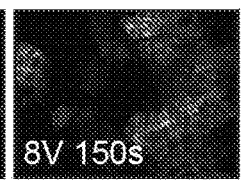  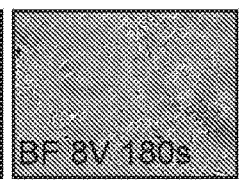
FIG. 13F  FIG. 13G  FIG. 13H  FIG. 13I  FIG. 13J
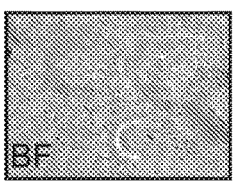 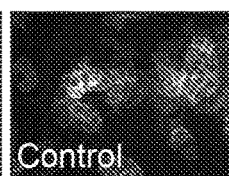 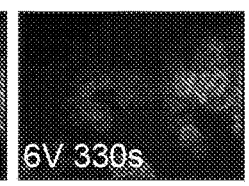  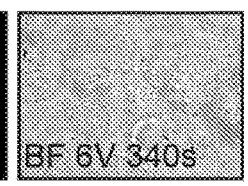
FIG. 13K  FIG. 13L  FIG. 13M  FIG. 13N  FIG. 13O
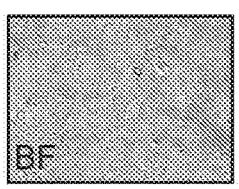 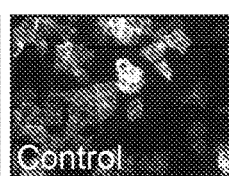 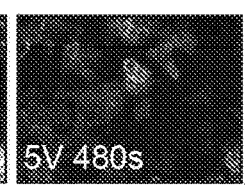  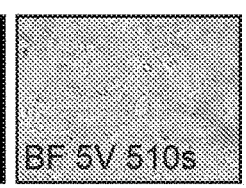
FIG. 13P  FIG. 13Q  FIG. 13R  FIG. 13S  FIG. 13T
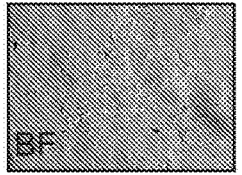 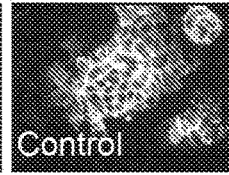 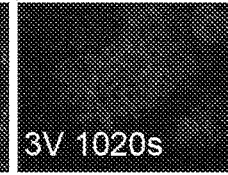 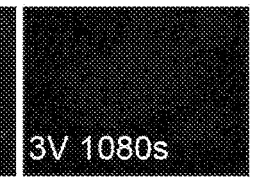 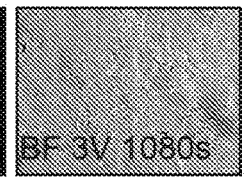

FIG. 17A
B cells
FIG. 17B
T cells and B cells mixture
Normal
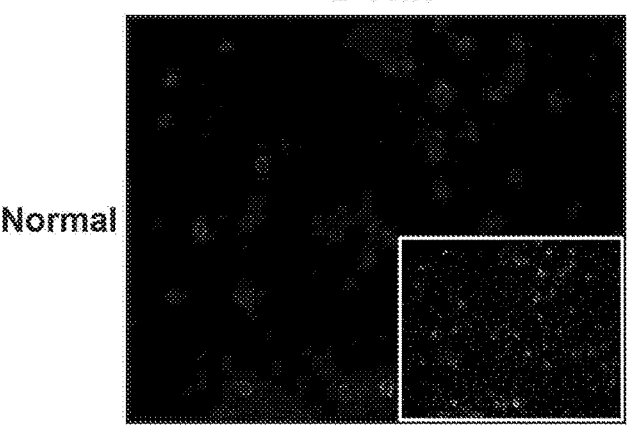
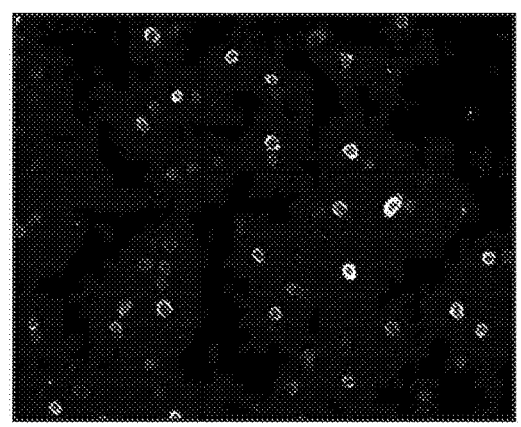
FIG. 17C
FIG. 17D
Ultrafast
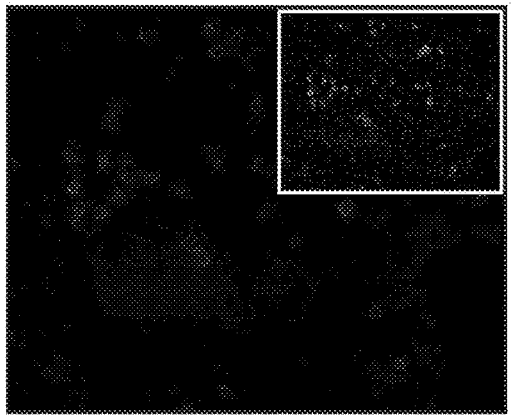
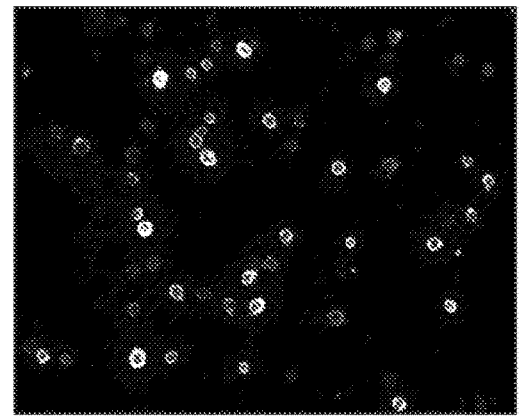

After last cell is trapped, oil (yellow) is flow Through the channel to displace aqueous (blue) solution.

SYSTEMS AND METHODS FOR CYCLIC FLUORESCENCE IMAGING

CROSS-REFERENCE

This application claims the benefit of U.S. Provisional Application No. 62/422,956, filed Nov. 16, 2016, which is incorporated herein by reference in its entirety.

BACKGROUND

Labeling and detecting molecules can be useful in scientific research, clinical treatment, and industrial applications. Labeling molecules in a biological context can allow for the identification of particular molecules of interest, which can be useful in determining the presence or absence of that molecule under defined experimental conditions. Detection of labeled molecules in an experimental system can be used to determine characteristics of cells associated with the labeled molecules, such as cellular phenotype. More than one kind of molecule in a cell can be labeled at one time in order to provide more information regarding the state of the experimental system. Through the improvement of methods and systems used in the processes of labeling and detecting molecules of interest, the utility of those methods and systems in the contexts of scientific research, clinical treatment, and industrial applications will increase.

SUMMARY

Described herein are methods of ultrafast labeling and de-labeling a cell or molecule, the method comprising: providing a cell or molecule associated with a substrate; contacting the cell or molecule with a detectable agent; labeling a plurality of sites of the cell or molecule with the detectable agent; applying a voltage across the cell or molecule; and de-labeling the cell or molecule, wherein de-labeling comprises removal of or quenching of the detectable agent on the cell or molecule. Also described herein are methods of ultrafast labeling, comprising: providing a cell or molecule associated with a substrate; heating the cell or molecule to a controlled temperature; delivering a detectable agent to the cell or molecule using a flow cell; and contacting the cell or molecule with the detectable agent. Also described herein are methods of de-labeling a labeled cell or molecule, the methods comprising: providing a cell or molecule associated with a substrate, wherein the cell or molecule is labeled with a plurality of detectable agents; and applying a voltage to the labeled cell or molecule; and de-labeling at least 75% of the plurality of detectable agents on the labeled cell or molecule in less than 15 minutes. Also described herein are systems for labeling and de-labeling a cell or molecule, the systems comprising: a substrate configured to hold a cell or molecule; a first detectable agent; a flow cell configured to pass a fluid across the cell or molecule; a voltage source; a temperature control device configured to heat the cell or molecule to a temperature set point, wherein the temperature of the cell or molecule is controlled to be within 3 degrees Celsius of a temperature set point; a detector configured to detect a first detectable agent; a computing device configured to operate the voltage source and the detector, the computing device comprising a processor and a non-transitory, tangible computer-readable storage medium, the storage medium storing a set of instructions that, when executed by the processor, cause; the detector to detect the first detectable agent signal; and the voltage source to apply a voltage to the solution in contact with the cell or molecule.

In various aspects, the methods described herein comprise methods for labeling and de-labeling a cell, the methods comprising: providing a cell associated with a substrate; contacting the cell with a detectable agent; labeling a plurality of sites of the cell with the detectable agent; applying an voltage across the cell; and de-labeling the cell, wherein de-labeling comprises removal of or quenching of the detectable agent on the cell.

In various aspects, the methods described herein comprise methods for labeling and de-labeling a cell, the methods comprising: providing a cell associated with a substrate; contacting the cell with a detectable agent; labeling a plurality of sites of the cell with the detectable agent; applying a voltage to a solution in contact with the cell; and de-labeling the cell.

In various aspects, applying voltage to the solution in contact with the cell generates one or more reactive chemical species. In various aspects, de-labeling of a cell comprises contacting the detectable agent with the one or more reactive chemical species.

In some aspects the methods for labeling and de-labeling a cell can further comprise detecting the detectable agent after labeling the plurality of sites. In some aspects, the methods for labeling and de-labeling a cell can comprise methods wherein the detecting comprises optically detecting the detectable agent.

In some aspects, the methods for labeling and de-labeling a cell can comprise labeling and de-labeling a cell in less than 20 minutes, less than 15 minutes, less than 10 minutes, less than 9 minutes, less than 8 minutes, less than 7 minutes, less than 6 minutes, less than 5 minutes, less than 4 minutes, or less than 3 minutes.

In some aspects, the methods for labeling and de-labeling a cell can comprise repeating the methods of labeling and de-labeling a plurality of times. In some aspects, the methods for labeling and de-labeling a cell can be performed 2 times within 30 minutes, 3 times within 45 minutes, 4 times within 60 minutes, 5 times within 75 minutes, or 6 times within 90 minutes.

In some aspects, the methods for labeling and de-labeling a cell can comprise repeating the methods of labeling and de-labeling in cycles for at least 2 times, at least 3 times, at least 4 times, at least 5 times, at least 10 times, or at least 50 times.

In some aspects, the methods for labeling and de-labeling a cell can further comprise labeling the cell with a plurality of detectable agents or imaging the cell labeled with a plurality of detectable agents. In some aspects, the methods for labeling and de-labeling a cell can comprise methods wherein the plurality of detectable agents can contact the cell alone or in combination.

In some aspects of the methods for labeling and de-labeling a cell can further comprise controlling the temperature of the cell to be from 26° C. to 60° C., from 30° C. to 45° C., from 35° C. to 45° C., from 35° C. to 40° C., from 36.5° C. to 37.5° C. In various aspects, the methods for labeling and de-labeling a cell can comprise methods wherein the temperature can be controlled within 0.5 degrees Celsius, within 1 degree Celsius, within 2 degrees Celsius, or within 3 degrees Celsius of the temperature set point.

In some aspects, the methods for labeling and de-labeling a cell can comprise methods wherein the detectable agent covalently attached to an antibody, wherein has a concentration of between 0.01 µg/ml to 500 µg/ml, 0.01 µg/ml to 100 µg/ml, 0.05 µg/ml to 10 µg/ml, or 0.1 µg/ml to 5 µg/ml during the labeling. In some aspects, the methods for labeling and de-labeling a cell can comprise methods wherein the detectable agent is covalently attached to a CD4 antibody, wherein the CD4 antibody has a concentration of between 0.01 µg/ml to 500 µg/ml, 0.01 µg/ml to 100 µg/ml, 0.05 µg/ml to 10 µg/ml, or 0.1 µg/ml to 5 µg/ml during the labeling. In some aspects, the methods for labeling and de-labeling a cell can comprise methods wherein the detectable agent is covalently attached to a CD3 antibody, wherein the CD3 antibody has a concentration of between 0.01 µg/ml to 500 µg/ml, 0.01 µg/ml to 100 µg/ml, 0.05 µg/ml to 10 µg/ml, or 0.1 µg/ml to 5 µg/ml during the labeling. In some aspects, the methods for labeling and de-labeling a cell can comprise methods wherein the detectable agent is covalently attached to a CD28 antibody, wherein the CD28 antibody has a concentration of between 0.01 µg/ml to 500 µg/ml, 0.01 µg/ml to 100 µg/ml, 0.05 µg/ml to 10 µg/ml, or 0.1 µg/ml to 5 µg/ml during the labeling.

In some aspects, the methods for labeling and de-labeling a cell can comprise methods wherein the detectable agent is covalently attached to a nucleic acid, wherein the nucleic acid has a concentration of between 0.01 µg/ml to 500 µg/ml, 0.014 µg/ml to 100 µg/ml, 0.05 µg/ml to 50 µg/ml, or 0.1 µg/ml to 5 µg/ml during the labeling. In some aspects, the methods for labeling and de-labeling a cell can comprise methods wherein the detectable agent is covalently attached to a ribonucleic acid, wherein the ribonucleic acid has a concentration of between 0.01 µg/ml to 500 µg/ml, 0.01 µg/ml to 100 µg/ml, 0.05 µg/ml to 50 µg/ml, or 0.1 µg/ml to 5 µg/ml during the labeling. In some aspects, the methods for labeling and de-labeling a cell can comprise methods wherein the detectable agent is covalently attached to a deoxyribonucleic acid, wherein the deoxyribonucleic acid has a concentration of between 0.01 µg/ml to 500 µg/ml, 0.01 µg/ml to 100 µg/ml, 0.05 µg/ml to 50 µg/ml, or 0.1 µg/ml to 5 µg/ml during the labeling.

In some aspects the methods for labeling and de-labeling a cell can further comprise contacting the cell with the detectable agent for a time of 10 seconds to 15 minutes, 30 seconds to 10 minutes, 1 minute to 8 minutes, or 2 minutes to 6 minutes, not more than 5 minutes, not more than 7.5 minutes, or not more than 10 minutes.

In some aspects, the methods for labeling and de-labeling a cell can comprise methods wherein a portion of the plurality of sites of the cell are labeled, the portion being at least 25%, at least 50%, at least 60%, at least 70%, at least 75%, at least 80%, at least 90%, or at least 95%. In some aspects, the methods for labeling and de-labeling a cell can comprise methods wherein the portion of the plurality of sites of the cell are labeled with the detectable agent in a time of not more than 15 minutes, not more than 10 minutes, not more than 7.5 minutes, not more than 5 minutes, not more than 4 minutes, not more than 3 minutes, not more than 2 minutes, or not more than 1 minute.

In some aspects, the methods for labeling and de-labeling a cell can comprise methods wherein the saturation of the plurality of detectable agents on the cell is more than 25%, more than 50%, more than 75%, or more than 90% of the saturation as compared to a second cell labeled under the same conditions, except that the labeling of the second cell is performed at 20° C. for 1 hour.

In some aspects, the methods for labeling and de-labeling a cell can comprise methods wherein the voltage applied to the solution in contact with the cell can be 1 V to 100 V, 1 V to 50 V, 1 V to 25 V, or 5 V to 15 V, or at least 8 V. In some aspects, the methods for labeling and de-labeling a cell can comprise methods wherein the voltage can be applied to the cell for 1 second to 20 minutes, 1 second to 15 minutes, 10 seconds to 10 minutes, 20 seconds to 5 minutes, 30 seconds to 3 minutes, or 50 seconds to 150 seconds. In some aspects, the methods for labeling and de-labeling a cell can comprise methods wherein the voltage can be a direct current (DC), an alternating current (AC), or a combination of DC and AC.

In some aspects, the methods for labeling and de-labeling a cell can comprise methods wherein at least 90% of the plurality of sites are de-labeled in a time of less than 15 minutes, less than 10 minutes, less than 6 minutes, less than 5 minutes, less than 4 minutes, or less than 3 minutes, less than 2 minutes, less than 1 minute, or less than 30 seconds. In some aspects, the methods for labeling and de-labeling a cell can comprise methods wherein at least 95% of the plurality of detectable agents on the cell are de-labeled in less than 10 minutes, less than 5 minutes, less than 4 minutes, less than 3 minutes, less than 2 minutes, or less than 1 minute. In some aspects, the methods for labeling and de-labeling a cell can comprise methods wherein at least 96%, at least 97%, at least 98%, at least 99%, at least 99.5%, or at least 99.9% of the plurality of detectable agents on the cell are de-labeled.

In some aspects, the methods for labeling and de-labeling a cell can comprise methods wherein a residual fluorescence detected from the cell is less than 5%, less than 2%, less than 1%, less than 0.5%, or less than 0.1%.

In some aspects of the methods for labeling and de-labeling, the methods can further comprise contacting the labeled cell with a quenching agent. In some aspects, the methods for labeling and de-labeling a cell can comprise methods wherein the quenching agent is Black Hole Quencher.

In some aspects, the methods for labeling and de-labeling a cell can comprise methods wherein the plurality of detectable agents can comprise a fluorescent detectable agent. In some aspects, the methods for labeling and de-labeling a cell can comprise methods wherein the plurality of detectable agents can be covalently attached to an affinity tag. In some aspects, the methods of labeling and de-labeling a cell can comprise methods wherein the affinity tag can be an aptamer or an antibody or a nucleic acid. In some aspects, the methods for labeling and de-labeling a cell can comprise methods wherein the nucleic acid comprises a ribonucleic acid, and in some aspects, the methods of labeling and de-labeling a cell can comprise methods wherein the nucleic acid comprises a deoxyribonucleic acid.

In some aspects, the methods for labeling and de-labeling a cell can comprise methods wherein the substrate can comprise a chip. In some aspects, the methods for labeling and de-labeling a cell can comprise methods wherein the substrate can comprise a single-cell array, and in some aspects, the methods for labeling and de-labeling a cell can comprise methods wherein the single-cell array is a regular array, comprising a plurality of cells arranged in periodic format. In some aspects, the methods for labeling and de-labeling a cell can comprise methods wherein the single-cell array is an unordered array, comprising a monolayer of a plurality of cells covering more than 30%, more than 40%, more than 50%, more than 60%, more than 70%, more than 80%, more than 90% of the substrate. In some aspects, the methods for labeling and de-labeling a cell can comprise methods wherein the substrate can be a planar substrate.

In some aspects, the methods for labeling and de-labeling a cell can comprise methods wherein the plurality of cells can comprise a tissue.

In some aspects the methods for labeling and de-labeling a cell can further comprise delivering a fluid to the substrate using a flow cell. In some aspects, the methods for labeling and de-labeling a cell can comprise methods wherein the flow cell is a microfluidic device.

In various aspects, the methods described herein comprise methods of labeling a cell, the method comprising: providing a cell associated with a substrate; heating the cell to a controlled temperature; delivering a detectable agent to the cell using a flow cell; and contacting the cell with the detectable agent.

In some aspects, the methods of labeling a cell further comprise detecting the detectable agent after labeling the plurality of sites. In some aspects the methods of labeling a cell can comprise methods wherein the detecting comprises optically detecting the detectable agent.

In some aspects, the methods of labeling a cell further comprise labeling the cell with a plurality of detectable agents. In some aspects, the methods of labeling a cell can comprise methods wherein the plurality of detectable agents can contact the cell alone or in combination.

In some aspects, the methods of labeling a cell can comprise methods wherein the controlled temperature is from 26° C. to 60° C., from 30° C. to 45° C., from 35° C. to 45° C., from 35° C. to 40° C., from 36.5° C. to 37.5° C. In some aspects, the methods of labeling a cell can comprise methods wherein the controlled temperature is within 0.5 degree Celsius, within 1 degree Celsius, within 2 degrees Celsius, or within 3 degrees Celsius of a temperature set point.

In some aspects, the methods of labeling a cell can comprise methods wherein the detectable agent is covalently attached to an antibody, wherein the methods of labeling a cell can comprise methods wherein the antibody has a concentration of between 0.01 µg/ml to 500 µg/ml, 0.01 µg/ml to 100 µg/ml, 0.05 µg/ml to 10 µg/ml, or 0.1 µg/ml to 5 µg/ml during the labeling. In some aspects, the methods of labeling a cell can comprise methods wherein the detectable agent is covalently attached to a CD4 antibody, wherein the CD4 antibody has a concentration of between 0.01 µg/ml to 500 µg/ml, 0.01 µg/ml to 100 µg/ml, 0.05 µg/ml to 10 µg/ml, or 0.1 µg/ml to 5 µg/ml during the labeling. In some aspects, the methods of labeling a cell can comprise methods wherein the detectable agent is covalently attached to a CD3 antibody, wherein the CD3 antibody has a concentration of between 0.01 µg/ml to 500 µg/ml, 0.01 µg/ml to 100 µg/ml, 0.05 µg/ml to 10 µg/ml, or 0.1 µg/ml to 5 µg/ml during the labeling. In some aspects, the methods of labeling a cell can comprise methods wherein the detectable agent is covalently attached to a CD28 antibody, wherein the CD28 antibody has a concentration of between 0.01 µg/ml to 500 µg/ml, 0.01 µg/ml to 100 µg/ml, 0.05 µg/ml to 10 µg/ml, or 0.1 µg/ml to 5 µg/ml during the labeling.

In some aspects, the methods of labeling a cell can comprise methods wherein the detectable agent is covalently attached to a nucleic acid, wherein the nucleic acid has a concentration of between 0.01 µg/ml to 500 µg/ml, 0.01 µg/ml to 100 µg/ml, 0.05 µg/ml to 50 µg/ml, or 0.1 µg/ml to 5 µg/ml during the labeling. In some aspects, the methods of labeling a cell can comprise methods wherein the detectable agent is covalently attached to a ribonucleic acid, wherein the ribonucleic acid has a concentration of between 0.01 µg/ml to 500 µg/ml, 0.01 µg/ml to 100 µg/ml, 0.05 µg/ml to 50 µg/ml, or 0.1 µg/ml to 5 µg/ml during the labeling. In some aspects, the methods of labeling a cell can comprise methods wherein the detectable agent is covalently attached to a deoxyribonucleic acid, wherein the deoxyribonucleic acid has a concentration of between 0.01 µg/ml to 500 µg/ml, 0.014 µg/ml to 100 µg/ml, 0.05 µg/ml to 50 µg/ml, or 0.1 µg/ml to 5 µg/ml during the labeling.

In some aspects, the methods for labeling a cell further comprise methods wherein the cell is contacted with the detectable agent for a time of 10 seconds to 15 minutes, 30 seconds to 10 minutes, 1 minutes to 8 minutes, or 2 minutes to 6 minutes, no more than 5 minutes, no more than 7.5 minutes, or no more than 10 minutes.

In some aspects, the methods for labeling a cell can comprise methods wherein at least 25%, at least 50%, at least 60%, at least 70%, at least 75%, at least 80%, at least 90%, at least 95%, or at least 99% of a plurality of sites of the cell are labeled. In some aspects, the methods for labeling a cell can comprise methods wherein the saturation of the plurality of detectable agent on the cell is more than 25%, more than 50%, more than 75%, or more than 90% of the saturation of a second cell labeled under the same conditions, except that the labeling of the second cell was performed at 20° C. for 1 hour.

In some aspects, the methods for labeling a cell can comprise methods wherein the plurality of detectable agents comprises a fluorescent detectable agent. In some aspects, the methods for labeling a cell can comprise methods wherein the plurality of detectable agents is covalently attached to an affinity tag. In some aspects, the methods for labeling a cell can comprise methods wherein the affinity tag is an aptamer or an antibody or a nucleic acid. In some aspects, the methods for labeling a cell can comprise methods wherein the affinity tag comprises a ribonucleic acid, and in some aspects, the methods for labeling a cell can comprise methods wherein the affinity tag comprises a deoxyribonucleic acid.

In some aspects, the methods for labeling a cell can comprise methods wherein the substrate comprises a chip, and in some aspects, the methods for labeling a cell can comprise methods wherein the substrate comprises a single-cell array. In some aspects, the methods for labeling a cell can comprise methods wherein the single-cell array is a regular array, comprising a plurality of cells arranged in periodic format. In some aspects, the methods for labeling a cell can comprise methods wherein the single-cell array is a random array, comprising a monolayer of a plurality of cells covering more than 30%, more than 40%, more than 50%, more than 60%, more than 70%, more than 80%, more than 90% of the substrate. In some aspects, the methods for labeling a cell can comprise methods wherein the substrate can be a planar substrate.

In some aspects, the methods for labeling a cell can comprise methods wherein the plurality of cells comprises a tissue.

In some aspects, the methods for labeling a cell can comprise methods wherein the flow cell is a microfluidic device.

In various aspects, the methods described herein can comprise methods for de-labeling a labeled cell, the methods comprising: providing a cell associated with a substrate, wherein the cell is labeled with a plurality of detectable agents; and applying a voltage to the labeled cell; and de-labeling at least 75% of the plurality of detectable agents on the labeled cell in less than 15 minutes.

In various aspects, the methods described herein can comprise methods for de-labeling a labeled cell, the methods comprising: providing a cell associated with a substrate, wherein the cell is labeled with a plurality of detectable agents; applying a voltage to a solution in contact with the cell to generate one or more reactive chemical species; and de-labeling at least 75% of the plurality of detectable agents on the labeled cell in less than 15 minutes, wherein de-labeling comprises contacting the detectable agent with the one or more reactive chemical species.

In some aspects, the methods for de-labeling a cell can further comprise detecting the detectable agent after de-labeling the plurality of sites.

In some aspects, the methods for de-labeling a cell can comprise methods wherein the detecting comprises optically detecting the detectable agent.

In some aspects, the methods for de-labeling a cell can comprise methods wherein the applied voltage is 1 V to 100 V, 1 V to 50 V, 1 V to 25 V, 5 V to 15 V, at least 7 V, or at least 8 V. In some aspects, the methods for de-labeling a cell can comprise methods wherein the voltage is applied to the labeled cell for 1 second to 20 minutes, 1 second to 15 minutes, 10 seconds to 10 minutes, 20 seconds to 5 minutes, 30 seconds to 3 minutes, or 50 seconds to 150 seconds. In some aspects, the methods for de-labeling a cell can comprise methods wherein the voltage is a direct current (DC), an alternating current (AC), or a combination of DC and AC.

In some aspects, the methods for de-labeling a cell can comprise methods wherein a fluidic flow is applied in a continuous, intermittent, timed, or controlled manner, or a combination thereof.

In some aspects, the methods for de-labeling a cell can comprise methods wherein at least 95% of a plurality of sites of the cell are de-labeled in a time of less than 15 minutes, less than 10 minutes, less than 6 minutes, less than 5 minutes, less than 4 minutes, or less than 3 minutes, less than 2 minutes, less than 1 minute, or less than 30 seconds. In some aspects, the methods for de-labeling a cell can comprise methods wherein at least 95% of the plurality of detectable agents on the cell are de-labeled in less than 10 minutes, less than 5 minutes, less than 4 minutes, less than 3 minutes, less than 2 minutes, or less than 1 minute. In some aspects, the methods for de-labeling a cell can comprise methods wherein at least 96%, at least 97%, at least 98%, at least 99%, at least 99.5%, or at least 99.9% of the plurality of detectable agents on the cell are de-labeled in less than 10 minutes.

In some aspects, the methods for de-labeling a cell can comprise methods wherein a residual fluorescence detected from the cell is less than 5%, less than 2%, less than 1%, less than 0.5%, or less than 0.1%.

In some aspects, the methods for de-labeling a cell can further comprise contacting the labeled cell with a quenching agent. In some aspects, the methods for de-labeling a cell can comprise methods wherein the quenching agent is Black Hole Quencher.

In some aspects, the methods for de-labeling a cell can comprise methods wherein the plurality of detectable agents comprises a fluorescent detectable agent.

In some aspects, the methods for de-labeling a cell can comprise methods wherein the plurality of detectable agents is covalently attached to an affinity tag. In some aspects, the methods for de-labeling a cell can comprise methods wherein the affinity tag is an aptamer or an antibody or a nucleic acid. In some aspects, the methods for de-labeling a cell can comprise methods wherein the affinity tag comprises a ribonucleic acid, and in some aspects, the methods for de-labeling a cell can comprise methods wherein the affinity tag comprises a deoxyribonucleic acid.

In some aspects, the methods for de-labeling a cell can comprise methods wherein the substrate comprises a chip. In some aspects, the methods for de-labeling a cell can comprise methods wherein the substrate comprises a single-cell array. In some aspects, the methods for de-labeling a cell can comprise methods wherein the single-cell array is a regular array, comprising a plurality of cells arranged in periodic format. In some aspects, the methods for de-labeling a cell can comprise methods wherein the single-cell array is a random array, comprising a monolayer of a plurality of cells covering more than 30%, more than 40%, more than 50%, more than 60%, more than 70%, more than 80%, more than 90% of the substrate. In some aspects, the methods for de-labeling a cell can comprise methods wherein the substrate is a planar substrate.

In some aspects, the methods for de-labeling a cell can comprise methods wherein the plurality of cells comprises a tissue.

In some aspects, the methods for de-labeling a cell further comprise delivering a fluid to the substrate using a flow cell. In some aspects, the methods for de-labeling a cell can comprise methods wherein the flow cell is a microfluidic device.

In various aspects, the systems described herein can comprise systems for labeling and de-labeling a cell, the systems comprising: a substrate configured to hold a cell; a first detectable agent; a flow cell configured to pass a fluid across the cell; a voltage source; a temperature control device configured to heat the cell to a temperature set point, wherein the temperature of the cell is controlled to be within 3 degrees Celsius of a temperature set point; a detector configured to detect a first detectable agent; a computing device configured to operate the voltage source and the detector, the computing device comprising a processor and a non-transitory, tangible computer-readable storage medium, the storage medium storing a set of instructions that, when executed by the processor, cause; the detector to detect the first detectable agent signal; and the voltage source to apply a voltage to the solution in contact with the cell.

In some aspects, the systems for labeling and de-labeling can comprise systems wherein the detector has a spatial resolution of less than 5 micrometers, 4, micrometers, 3, micrometers, 2 micrometers, 1 micrometer, 0.5 micrometer, or 0.1 micrometer.

In some aspects, the systems for labeling and de-labeling can comprise systems wherein the detector has a imaging sensitivity capable of detecting less than 10,000 detectable agents, less than 5,000 detectable agents, less than 1,000 detectable agents, less than 500 detectable agents, less than 100 detectable agents, less than 50 detectable agents, or less than 10 detectable agents.

In some aspects, the systems for labeling and de-labeling can comprise systems wherein at least 10 cells per second per detection channel, at least 100 cells per second per detection channel, at least 1000 cells per second per detection channel, at least 5000 cells per second per detection channel can be imaged.

In some aspects, the systems for labeling and de-labeling can comprise systems wherein the temperature-control device is configured to control the temperature of the cell to within a range of no more than 2° C., no more than 1° C., no more than 0.5° C. of a temperature set point. In some aspects, the systems for labeling and de-labeling can comprise systems wherein the temperature control device is configured to heat the cell to a temperature of at least 26° C., at least 30° C., at least 35° C., at least 40° C., at least 45° C., at least 60° C.

In some aspects, the systems for labeling and de-labeling can further comprise a voltage source configured to apply a voltage of at least 1 volt, at least 3 volts, at least 5 volts, at least 7 volts, at least 8 volts, at least 9 volts, at least 10 volts to the solution in contact with the cells.

In some aspects, the systems for labeling and de-labeling can further comprise an imaging device.

In some aspects, the systems for labeling and de-labeling can comprise systems wherein the first detectable agent is a fluorescent detectable agent. In some aspects, the systems for labeling and de-labeling can further comprise a light source configured to excite the fluorescent detectable agent.

In some aspects, the systems for labeling and de-labeling can further comprise a second detectable agent. In some aspects, the systems for labeling and de-labeling can further comprise a detector configured to detect the second detectable agent.

In some aspects, the systems for labeling and de-labeling can comprise systems wherein the substrate comprises a chip.

In some aspects, the systems for labeling and de-labeling can further comprise systems wherein the computing device is further configured to operate the flow cell.

In some aspects, the systems for labeling and de-labeling can further comprise a fluid reservoir connected to the flow cell. In some aspects, the systems for labeling and de-labeling can comprise systems wherein the flow cell comprises a microfluidic device.

In some aspects, the systems for labeling and de-labeling can comprise systems wherein the substrate is enclosed within the apparatus.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 10A and 10E are images of labeled cells prior to the application of voltage, according to an embodiment of the present disclosure. FIGS. 10B and 10F are images of labeled cells following the application of 8 volts to the solution in contact with the cells and/or detectable agent for 30 seconds, according to an embodiment of the present disclosure. FIGS. 10C and 10G are images of labeled cells following the application of 8 volts to the solution in contact with the cells and/or detectable agent for 60 seconds, according to an embodiment of the present disclosure. FIG. 10D and FIG. 10H are bright field images of the cells following the ultrafast de-labeling process, according to an embodiment of the present disclosure.

FIGS. 13A-13T show de-labeling of PE-anti EpCAM labeled cells after 150 seconds and 180 seconds of 8 volts (FIGS. 13A-13E), 330 seconds and 340 seconds of 6 volts (FIGS. 13F-13J), 480 seconds and 510 seconds of 5 volts (FIGS. 13K-13O), and 1020 seconds and 1080 seconds of 3 volts (FIGS. 13P-13T). FIG. 13E, FIG. 13J, FIG. 13O, and FIG. 13T are bright field images illustrating that the cells themselves have not been altered or lifted off from the substrate by the ultrafast de-labeling process.

FIGS. 17A-17D show similar antibody specificity and similar levels of non-specific binding when labeling B-cells alone, a cell type lacking the CD28 cell surface protein, (FIG. 17A and FIG. 17C) or 1:1 mixtures of B-cells and T-cells expressing CD28 (FIG. 17B and FIG. 17D) with PE-anti-CD28 antibody for 5 minutes using normal labeling methodology (FIG. 17A and FIG. 17B) or ultrafast labeling methodology (FIG. 17C and FIG. 17D). Panel insets have been subjected to post-processing in which the signal gain has been increased after image capture for the purpose of illustrating the presence of cells. Signal gain levels were identical for all image panels except the insets of FIG. 17A and FIG. 17C.

FIG. 18A shows mixed B-cells and T-cells labeled using normal and ultrafast labeling methods. FIG. 18B shows B-cell and T-cell labeled separately, using both normal and ultrafast labeling methods.

FIG. 19A shows labeled cells using bright field imaging, and FIG. 19B shows labeled cells using fluorescent imaging. FIG. 19C shows the same cells after de-labeling with Black Hole Quencher. FIG. 19D shows re-labeling with another fluorescent antibody (e.g., detectable agent).

FIG. 20A depicts cells contacted with PE-anti-cytokeratine, according to an embodiment of the present disclosure. FIG. 20B depicts the same cells following de-labeling by exposure to 8 volts for 5 minutes, according to an embodiment of the present disclosure. FIG. 20C depicts the same cells, which were subsequently labeled once again using PE-anti-MUC1, according to an embodiment of the present disclosure. The same cells were then de-labeled by exposure to 8 volts for 5 minutes (FIG. 20D), re-labeled with PE-anti-HER2 (FIG. 20E), de-labeled by exposure to 8 volts for 5 minutes (FIG. 20F), re-labeled with PE-anti-EpCAM (FIG. 20G), de-labeled by exposure to 8 volts for 5 minutes (FIG. 20H), and re-labeled with PE-anti-EGFR, according to an embodiment of the present disclosure.

FIG. 21G shows single cells in suspension in a single-cell array.

FIGS. 22A and 22B illustrate single-cell arrays, according to an embodiment of the present disclosure. FIG. 22C illustrates a single-cell array, according to an embodiment of the present disclosure.

DETAILED DESCRIPTION

Figure 1:
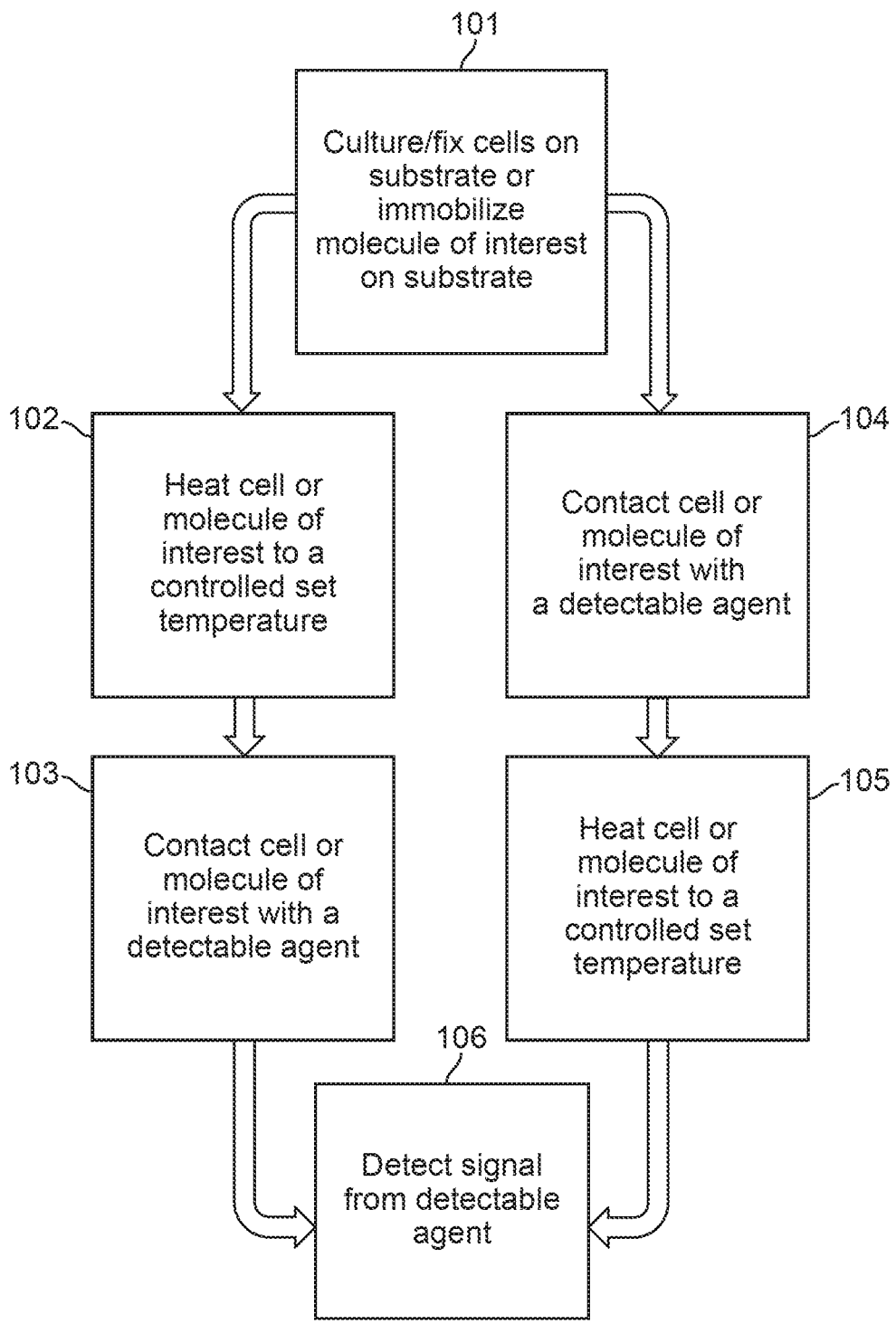
FIG. 1 shows a flow diagram of ultrafast labeling of cells or molecules of interest with a detectable agent. As shown, samples (e.g., cells or molecules of interest) can be heated to a set temperature first and then contacted with a detectable agent or samples can be contacted with a detectable agent first and then heated to a set temperature (compare diagram sequence 101-102-103-106 with diagram sequence 101-104-105-106).

The disclosure herein provides methods and systems for improved efficiency of labeling (e.g., staining) and de-labeling (e.g., destaining, removing a detectable agent, or decreasing a detectable signal produced by a detectable agent) cells or molecules with respect to a detectable agent or plurality of detectable agents. In addition to improving the efficiency of the individual tasks of labeling or de-labeling a molecule as an ends in and of themselves, the methods and systems disclosed herein can be of particular value in experimental systems in which the number of molecules to be detected exceeds the number of detectable agent signals that can be detected simultaneously. In such situations, the speed at which an experiment can be performed is limited by the time required to perform the steps of labeling a sample with a set of detectable agents, detecting the first set of detectable agents, de-labeling the sample which is labeled with the first set of detectable agents, and labeling the sample (e.g., a second set of molecules of interest) with a second set of detectable agents (a process which can include a plurality of cycles of labeling and/or de-labeling a sample such that all cells or molecules of interest are labeled and detected). Accordingly, improvements to the efficiency of each of the steps of labeling and de-labeling a cell or molecule are compounded with each repetition of the process of detecting, de-labeling, and labeling a given set of cells or molecules of interest with a given set of detectable agents.

For example, experiments in which a greater number of different types of molecules of interest are to be detected than can be simultaneously detected by the available detection system or than can be resolved from one another when used simultaneously (e.g., as a result of spectral overlap of fluorescent detectable agents) must either be repeated or subjected to a de-labeling and labeling procedure in order for each molecule of interest to be labeled and detected. Repeating an experiment can introduce experimental variability in addition to increasing the time required to detect all molecules of interest, while de-labeling and labeling molecules using conventional methods and systems can require considerable amounts of time. By employing the methods and systems described herein, which can improve the time required to label, de-label, and/or detect molecules, detection of a large number of different types of molecules in a single experiment can be accomplished quickly, even using a detection system of modest capabilities.

Therefore, the methods and systems described herein (as described in the process of FIG. 1) can involve providing a cell or molecule associated with or on a substrate (101, 201). Cells can be primary or immortalized and can be live or fixed. The substrate can be planar or it can comprise a multi-titer plate. The temperature of the cell or molecule (e.g., the sample) can be regulated such that it maintains a temperature within a specified range (e.g., 36.5° C. and 37.5° C.) or within an allowable temperature variation (e.g., 0.5° C.) (102, 202), while being contacted with a first detectable agent (or a first plurality of detectable agents, see 103, 203) to improve the speed of labeling of the cell or molecule with the detectable agent. Alternatively, the cell can be contacted with a first detectable agent (104, 205) prior to being heated (105, 206). A detectable agent can comprise a fluorophore, and the fluorophore can be, for example, a polymer dot, an organic dye, or a protein dye. In some embodiments, the sample can be cooled (e.g., allowed to cool by thermal radiation or thermal conductivity, or by refrigeration, 204, 207). The detectable agents can then be detected using a fluorescent microscope (106, 208) and subsequently de-labeled in less than 5 minutes (as described in the processes of FIG. 3-FIG. 8) by applying a voltage or an electric field to the detectable agents associated with the cell or molecule of interest (302, 405, 505, 605, 705, 805). The voltage or electric field can be generated by a power supply, which can be used to produce an electric potential across the sample (e.g., an electric potential of 8 volts created between electrodes 1 cm apart and oriented such that the sample is situated between the electrodes, which can comprise an electric field of 800 volts/meter through the sample). The voltage generated by the power supply can be used to produce reactive chemical species, such as reactive oxygen species, which can react with the detectable agent to quench or remove the fluorescence signal from the detectable agent. As further described in FIG. 4-FIG. 8, the processes of labeling, detecting, and de-labeling can then be repeated one, two, three, four, five, or more times with an additional detectable agent (e.g., a second detectable agent, a third detectable agent, etc.) or additional pluralities of detectable agents (e.g., a second plurality of detectable agents, a third plurality of detectable agents, etc.) in order to increase the total number of molecules or aspects of the sample analyzed in one experiment, while simultaneously improving the speed and the level of de-staining at which such a process is performed. The process of ultrafast cyclic labeling and de-labeling of a cell or molecule can be implemented by a system described herein, thus providing a platform for repeatable, high-speed, multiplex-capable cellular and molecular labeling and de-labeling.

Methods of Labeling

A cell or molecule of interest can be labeled with a detectable agent or a plurality of detectable agents to identify, quantify, or monitor aspects of the cell or molecule of interest. Labeling of a cell or molecule can comprise causing a specific cell or molecule to be associated with a detectable agent or a plurality of detectable agents, and this process can be influenced by several factors. A non-limiting list of aspects that can impact cell or molecule labeling include the amount of time a detectable agent is placed in contact with the cell or molecule, the concentration of the detectable agent used to label the cell or molecule, the temperature of the cell or molecule during the process of being contacted by the detectable agent, the choice of detectable agent, the method of contacting the cell or molecule with the detectable agent, whether the cell or molecule is fixed or unfixed, whether the cell or molecule is adhered, adsorbed, or otherwise immobilized on a substrate, whether the fluid around the cell is moving relative to the cell, and whether the cell or molecule is washed between steps of the labeling process. The methods disclosed herein can comprise the stipulation of certain aspects of the labeling process, giving rise to remarkably strong labeling (e.g., a detectable agent signal of high intensity compared to standard labeling protocols while retaining specificity for the targeted cell or molecule, as shown in FIGS. 17A-17D while requiring a surprisingly short period of time over which the cell or molecule need be contacted by the detectable agent.

Figure 9A:
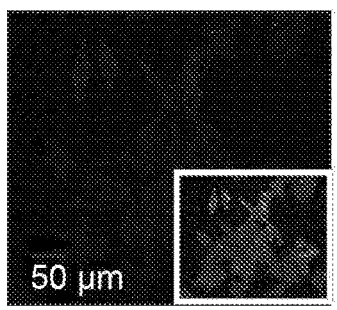
FIGS. 9D-9F show ultrafast labeling (or superfast cyclic staining, SCS, which can comprise a 10-fold increase in detectable agent concentration compared to normal labeling methods) of cells, as compared with labeling using standard protocols (FIGS. 9A-9C). Insets of FIG. 9A and FIG. 9D have been subjected to post-processing in which the signal gain has been increased after image capture for the purpose of illustrating the presence of cells. Signal gain levels were identical for all image panels except the inset panels of FIG. 9A and FIG. 9D.
FIG. 9G shows flow cytometry measurements of cells labeled using ultrafast labeling (e.g., 10×37° C., 5 min) and indicates the ultrafast labeling method results in highly efficient labeling as indicated by the high positive fluorescence intensity exhibited by the cells in flow cytometry, while at the same time maintains low non-specific binding that is comparable to that obtained with normal labeling methods.
Figure 9B:
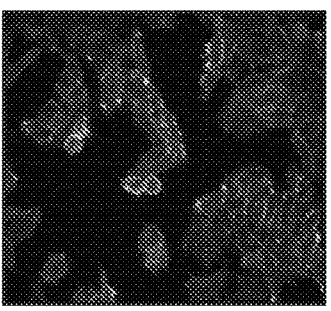
Figure 9C:
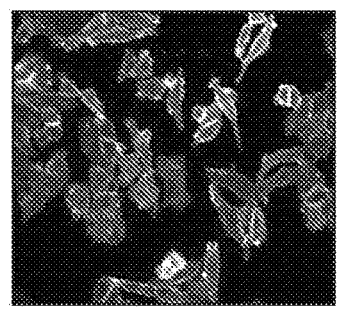
Figure 9D:
Figure 9E:
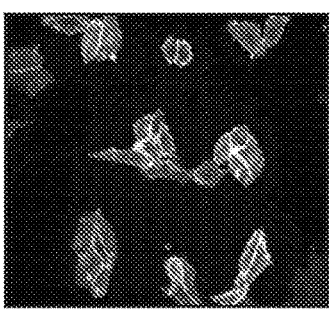
Figure 9F:
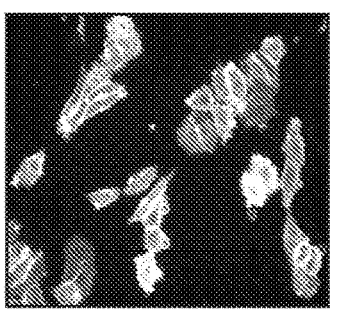
Figure 9G:
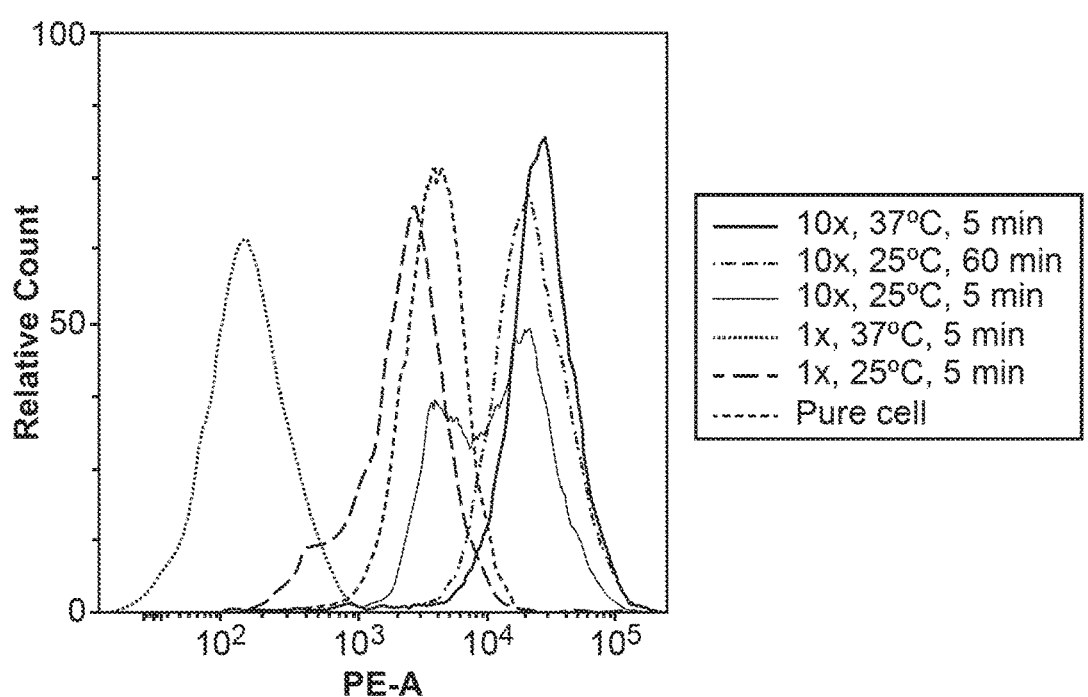

FIGS. 9A-9G shows the additive effects of increasing detectable agent concentration and increasing temperature on cell labeling. The extent of labeling (e.g., intensity of detectable agent signal) after 5 minutes of labeling is increased when temperature is increased from room temperature (approximately 24 degrees Celsius, FIG. 9A; inset represents post-processing increase of image gain for the purpose of illustrating the presence of cells) to 37 degrees Celsius (FIG. 9D; inset represents post-processing increase of image gain for the purpose of illustrating the presence of cells). The extent of labeling after 5 minutes is further increased if concentration of detectable agent is increased ten-fold at room temperature (10×C, FIG. 9E). The extent of labeling after 5 minutes is significantly improved over all conditions if temperature is increased to 37 degrees Celsius (° C.) at the same time that concentration is increased to ten-fold of normal labeling concentration ("10×C" in figure, FIG. 9F). The amount of detectable signal after 5 minutes under conditions of 37° C. and ten-fold detectable agent concentration is greater than the extent of labeling when cells or molecules of interest are labeled with detectable agent at room temperature and at normal labeling concentration, even after 60 minutes (FIG. 9B) and 120 minutes (FIG. 9C), implying that the combination of increased temperature and detectable agent concentration greatly increases the efficiency of labeling in less time than baseline labeling conditions (e.g., room temperature at normal labeling concentrations of detectable agent) require to reach steady state levels of labeling. FIG. 9G shows that maximum cell labeling (e.g., saturation of detectable agent signal or labeling intensity achieved after 60 min at room temperature) can be achieved in 5 minutes under ultrafast labeling conditions (e.g., 37° C. and 10-fold detectable agent signal).

A cell or molecule can be associated with another molecule (e.g., a detectable agent) or a substrate temporarily or permanently, for example, through preferential localization or chemical bonding. Association of molecules can occur as part of biological processes or as part of methods disclosed herein, such as contacting a molecule with a fluorescently-labeled affinity tag specific to that molecule. Alternatively, a cell can be said to be associated with a substrate if it is adherent to the substrate or if it is intentionally caused to be in prolonged contact with the substrate (e.g., if a force is applied to keep the cell in contact with the substrate, such as fluidic pressure).

An affinity tag is a molecule that is used to form a specific association with another molecule. An affinity tag can be an aptamer, an antibody, or a nucleic acid, and it can be associated with a detectable agent, such as a fluorophore. In some embodiments, an affinity tag can be associated with a detectable agent via a covalent bond. An aptamer can be an oligonucleotide or a peptide molecule, it can be naturally occurring or artificially engineered, and it can be used to specifically target a molecule of interest. In some cases, aptamers can limit the immune response in the system in which they are used. An antibody can be a polypeptide, comprising a light chain and a heavy chain, and the heavy and light chains can comprise a variable region. Each variable region of an antibody can comprise three complementarity determining regions (CDRs), which can determine the molecules with which the antibody specifically associates. A nucleic acid can comprise a ribonucleic acid or a deoxyribonucleic acid and can hybridize with a molecule of interest, as in fluorescence in situ hybridization (FISH). Thus, a nucleic acid affinity tag can be used to probe for an mRNA or DNA in cells used in the methods and systems disclosed herein. An affinity tag can be used to isolate cells or molecules before they are detected. For example, a fluorescent affinity tag can be used as a basis for sorting cells or molecules of interest before they are detected.

The methods of labeling (e.g., staining) described herein can incorporate standard methods of labeling a cell or molecule or they can be used in place of standard labeling procedures. Regular labeling procedures (e.g., standard labeling procedures) are commonly performed at room temperature (room temperature can be any temperature in the range of not less than about 20° C. and not more than about 25° C.) or colder, using a concentration of detectable agent within the manufacturer's recommended dilution range for that detectable agent and detection modality, for a period of at least thirty minutes and as long as 24 hours. Live cells in adherent culture and molecules associated with live cell are frequently stained with detectable agents at room temperature for a period of 60 to 120 minutes. Fixed cells and the molecules associated with them are commonly incubated in contact with a detectable agent overnight (e.g., 12 to 24 hours) at a temperature of 2-8 degrees Celsius (° C.) at the manufacturer's recommended dilution for the detectable agent and the intended detection modality.

A person of skill in the art will recognize that, while increasing the concentration of a detectable agent in contact with a cell or molecule of interest would be expected to increase the signal of the detectable agent, increasing detectable agent concentration would also be expected to increase undesirable non-specific labeling by the detectable agent (e.g., association of the detectable agent with non-targeted molecules and aspects of the cell based on stoichiometry rather than specific targeting of the detectable agent to a particular cell or molecule), diminishing the utility of any increases in detectable agent signal. Furthermore, a person of ordinary skill would understand that incremental returns on increasing detectable agent concentration, as evaluated by increased detectable agent signal, would diminish with each incremental increase in detectable agent concentration.

Therefore, the results produced using the methods and systems described herein are unexpected in that, by increasing temperature in addition to an increase in concentration of detectable agent the speed of sample labeling (e.g., the time required to reach 100% of maximum labeling achieved using conventional labeling protocols, see FIG. 9G) can be significantly increased without significant increases to non-specific labeling of detectable agents (see, e.g., FIG. 17A-17D).

Increased levels of detectable agent used to contact the sample (e.g., the molecule or cell of interest) can be quantified in a number of ways. With respect to a commercially obtained detectable agent, the concentration of detectable agent to be used in ultrafast labeling can be at least 5-fold (5×), 10-fold (10×), 20-fold (20×), 25-fold (25×), 50-fold (50×), 100-fold (100×), or 1000-fold (1000×) the lowest mass, concentration or dilution suggested by the supplier. In some embodiments, absolute concentration of detectable agent can be used to describe an appropriate amount of detectable agent with which to contact a sample (e.g., a cell or molecule of interest). In such situations, the concentration range for the detectable agent can be, for example, 0.01 µg/ml to 500 µg/ml, 0.01 µg/ml to 100 µg/ml, preferably 0.05 µg/ml to 10 µg/ml, or even more preferably 0.1 µg/ml to 5 µg/ml.

The volume of solution containing a detectable agent that is used to deliver the detectable agent to the sample can depend on the substrate used during labeling. In general, the detectable agent should be allowed to contact all sites of the sample that are to be labeled. In some embodiments, the substrate is a microfluidic device, and as little as 5 µl, 10 µl, 15 µl, 20 µl, 25 µl, 30 µl, 35 µl, 40 µl, 50 µl, 75 µl, 100 µl, 150 µl, 200 µl, 250 µl, or 300 µl can be used to label the cell. In some embodiments, the substrate is a 96-well plate, and as little as 10 µl, 15 µl, 20 µl, 25 µl, 30 µl, 35 µl, 40 µl, 50 µl, 75 µl, 100 µl, 150 µl, 200 µl, 250 µl, or 300 µl can be used to label the cell. In some embodiments, the substrate is a 384-well plate, and as little as 0.5 µl, 1 µl, 2 µl, 3 µl, 4 µl, 5 µl, 6 µl, 7 µl, 8 µl, 9 µl, 10 µl, 15 µl, 20 µl, 25 µl, 30 µl, 50 µl, 75 µl, 100 µl, or 150 µl can be used to label the cell.

The methods and systems of this disclosure, however, describe the means to improve the efficiency of labeling cells or molecules of interests with a detectable agent such that labeling of a cell or molecule can be accomplished (e.g., the association of a detectable agent with at least 50%, at least 80%, at least 85%, at least 90%, at least 95%, at least 99%, or at least 99.5% of sites available for specific labeling of a cell or molecule by that detectable agent) in less than 15 minutes, less than 10 minutes, less than 9 minutes, less than 8 minutes, less than 7 minutes, less than 6 minutes, less than 5 minutes, less than 4 minutes, less than 3 minutes, less than 2 minutes, or less than 1 minute.

A cell can comprise a plurality of sites, and those sites can be specific to individual affinity tags (e.g., aptamers, antibodies, or nucleic acid). For example, a site can be a molecule that is recognized by an affinity tag that is associated with a detectable agent. A sample can comprise a plurality of sites recognized by the same affinity tag or a plurality of sites recognized by a plurality of affinity tags. A molecule can comprise a plurality of sites with which a single type of affinity tag can associate or it can comprise a plurality of sites with which a plurality of types of affinity tags can associate. In some situations, not all sites may be available to affinity tags (e.g., as a result of molecular conformation, molecular interactions, or other circumstances which would prevent an affinity tag from contacting a site with which it would otherwise associate). Therefore, evaluation of the percentage of sites labeled by an affinity tag can take into account pertinent experimental considerations such as temperature, time, humidity, convective flow, pH, molecular conformations as they relate to hindrance of site-affinity tag interaction.

In particular, the temperature of a cell can be held or controlled to be no less than 26° C., no less than 30° C., no less than 31° C., no less than 32° C., no less than 33° C., no less than 34° C., no less than 35° C., no less than 36° C., no less than 37° C., no less than 38° C., no less than 39° C., no less than 40° C., no less than 45° C., no less than 50° C., no less than 55° C., no less than 60° C., or no less than 70° C. with an error of no more than 0.25° C., no more than 0.5° C., no more than 0.75° C., no more than 1° C., no more than 2° C., no more than 3° C., no more than 4° C., or no more than 5° C., while contacting the cell or molecule with an increased concentration of detectable agent (e.g., 1.5 times higher, 2 times higher, 5 times higher, 7 times higher, 10 times higher, 15 times higher, 20 times higher than the manufacturer's recommended concentration or dilution) to achieve the association of a detectable agent with at least 50%, at least 80%, at least 85%, at least 90%, at least 95%, at least 99%, or at least 99.5% of sites available for specific labeling of a cell or molecule by that detectable agent (e.g., saturation levels of labeling) in less than 15 minutes, less than 10 minutes, less than 9 minutes, less than 8 minutes, less than 7 minutes, less than 6 minutes, or less than 5 minutes, less than 4 minutes, less than 3 minutes, less than 2 minutes, less than 1 minute.

Saturation can refer to the relative intensity of a detectable agent signal of a labeled cell or molecule (e.g., relative to the signal of an unlabeled cell or molecule, relative to the signal of a cell or molecule labeled to saturation at room temperature, or relative to the signal of a maximally labeled cell) or it can refer to the percentage of sites with which an affinity tag (which can be associated with a detectable agent) is capable of associating that are occupied by the affinity tag (e.g., an affinity tag associated with a detectable agent). In each case, a saturation level (e.g., a semi-steady state maximum) is achievable as a function of variables such as time, concentration of detectable agent, and temperature. With respect to determining the degree or percentage of saturation (e.g., of a detectable agent or detectable agent signal following labeling or de-labeling), a reference condition can be used. For example, 100% saturation can represent the number of detectable agents or the detected signal (e.g., the number of photons per second) from detectable agents following labeling at 20 degrees Celsius for 2 hours. Likewise, background signal (e.g., 0% saturation) can be determined by using a reference point. For example, the amount of detectable agent or detectable agent signal detected from a sample that has not been labeled can be used as a reference point for saturation. Alternatively, control conditions (e.g., isotype controls, cells not expressing the particular biomarker in question, primary antibody without a fluorophore-conjugated secondary antibody, etc.) or specific spatial regions (e.g., an unstained region of the field of view) can be used as a reference point for background saturation. In some embodiments, reference points for saturation or detectable agent signal intensity can be used to normalize results from control samples or experimental samples.

As mentioned above, the methods disclosed herein for labeling a cell or molecule can comprise aspects of standardized staining or labeling protocols, such as the use of permeabilizing agents (e.g., the use of solutions comprising a detergent such as Triton X-100, Tween-20, or saponin), blocking agents (such as bovine serum albumin, casein, milk, or 0.1%, 0.5%, 1%, 2%, 5%, 10%, 15%, or 20% solutions of animal serum, including fetal bovine serum, rabbit serum, horse serum, goat serum, donkey serum, rat serum, mouse serum, dog serum, swine serum, monkey serum, chicken serum, and commercial blocking agents like BlockAid™), buffering agents (e.g., salts or ions like sodium, potassium, calcium, magnesium, chloride, citrate, borate, phosphate, acetate sulfate, tris, and bicarbonate, and phosphate buffered solutions like phosphate buffered saline, Dulbecco's phosphate buffered saline, Tris-buffered saline, HEPES, Hank's buffered saline solution, Earle's balanced salts solution, and culture media, including Dulbecco's modified Eagle's medium, Eagle's minimum essential medium, RPMI 1640) with or without indicator dyes (e.g., phenol red), chelators such as EDTA or heparin, and other common labeling solution additives like antibiotics and fungicides (e.g., streptomycin, penicillin, amphotericin B, and the like), L-glutamine, albumin, sodium azide, urea, and sodium dodecyl sulfate. In certain embodiments the methods disclosed herein can comprise washing the cell or molecule or performing antigen retrieval; however, these additions can increase the time required to complete labeling of the cell or molecule.

After the cell is labeled with a detectable agent, the detectable agent can be detected. In certain situations, it may be necessary to perform the method of labeling more than once, in succession. For example, if indirect immunofluorescence is to be used or if two different molecules capable of associating with the sample (e.g., antibodies, aptamers, or nucleic acids that have been linked to a detectable agent) or if 2, 3, 4, 5, 6, 7, or 8 pluralities of different types of molecules capable of associating with the sample requiring incompatible labeling solutions are being employed, the labeling procedure can be performed a plurality of times prior to detection.

Detectable Agents

A detectable agent can be a molecule or group of molecules that can be used to identify a cell, an aspect of a cell, or another molecule. Detectable agents can be used to label (e.g., to become associated with) a cell or a portion of a cell, such as a molecule of interest. Detectable agents can comprise molecules, dyes, proteins, polymers, or nanoparticles that, when stimulated, produce a signal (e.g., fluorophores) or molecules and dyes that produce a background signal (e.g., autofluorescent molecules) when under-stimulated. Detectable agents can be associated with a means of associating specifically with a cell or molecule of interest or a site on a cell or molecule of interest (e.g., an antibody, an aptamer, or a nucleic acid).

Detectable agents can be used to label specific molecules, aggregates of molecules, or cellular structures. As such, a detectable agent can be associated with (e.g., covalently bonded to) an affinity tag, such as an aptamer, an antibody, or nucleic acids (e.g., DNA or RNA) and proteins capable of hybridizing with, binding to, or otherwise associating with a molecule or cellular structure of interest. Affinity tags (e.g., aptamers, antibodies, or nucleic acids) can be specifically targeted to cellular or molecular targets (e.g., molecules of interest, including those listed below). A detectable agent can be associated directly with (e.g., conjugated directly to) an affinity tag capable of associating with the cell or molecule of interest or it can be associated with a molecule (such as an affinity tag) that is capable of associating specifically with another molecule, which is, in turn, capable of associating specifically with the cell or molecule of interest, as in indirect immunofluorescence.

An aptamer can comprise DNA, RNA, or a modified DNA or RNA and can be used to target a detectable agent, such as a fluorophore, to a specific target molecule (e.g., that is on or in a cell). Aptamers can be cleaved by enzymes, thus releasing the detectable agent from the bound target molecule.

An antibody can comprise a protein with a heavy chain and a light chain, and it can be directly bound to a detectable agent, such as a fluorophore, or it can be bound to a detectable agent through an intermediate moiety, such as a linker molecule. Similarly, an antibody (e.g., a primary antibody) can be specifically recognized by another antibody (e.g., a secondary antibody). If a primary antibody comprises an affinity tag, such as biotin, detectable agents associated with an avidin or streptavidin molecule can be indirectly associated with the primary antibody. Since avidin and streptavidin molecules can bind up to four biotin molecules, the number of detectable agents associated with a molecule can be increased by contacting a biotinylated antibody (e.g., a biotinylated antibody specific to a molecule of interest) with the molecule of interest and a biotinylated detectable agent in the presence of avidin or streptavidin molecules. Alternatively, an avidin or streptavidin molecule that is directly associated with a detectable agent (e.g., a fluorophore) can be used in a similar manner. Through the use of approaches such as primary-secondary antibody strategies, biotin-streptavidin strategies, and the like, it is possible to amplify cumulative detectable agent signal from a sample and to improve customization of labeling strategies.

Alternatively, a detectable agent can be associated with a protein in the form of a fusion protein that is expressed within the cell or introduced to the cell. If the protein with which the detectable agent (e.g., the fluorophore) forms a fusion protein is a molecule of interest, the detectable agent can be part of a molecule of interest.

A detectable agent can be an agent that can be detectable by a fluorescent imaging methodology. As such, a detectable agent can comprise a fluorophore. A fluorescent detectable agent can be an expressed molecule (e.g., a fluorescent protein) or a synthetic construct (e.g., a dye or fluorescent nanoparticle). A detectable agent can comprise a quantum dot, a polymer dot, or a similar fluorescent nanoparticle. A fluorescent detectable agent can be a small molecule (e.g., a dye) or a fluorescent protein.

A fluorescent detectable agent can be associated with a macromolecule. Therefore, a labeled molecule of interest can include a fluorescently labeled polypeptide (e.g., a labeled protein and/or a protein fragment), a fluorescently labeled nucleic acid molecule, a fluorescently labeled carbohydrate, a fluorescently labeled lipid, a fluorescently labeled macrocycle, a fluorescently labeled polyphenol, and/or a fluorescently labeled endogenous macromolecule complex (e.g., a primary antibody-secondary antibody complex).

A detectable agent can comprise a chromophoric polymer dot (e.g., a polymer dot). A polymer dot can be semiconducting, non-semiconducting or a combination thereof, and they can be developed to emit a signal with wavelengths ranging from ultraviolet to infrared, including the entire visual spectrum. Synthesis of polymer dots can include narrow-band emissive polymer dots such as boron-dipyrromethene (4,4-difluoro-4-bora-3a,4a-diaza-sindacene, BODIPY) or derivatives thereof. Polymer dots can be chemically functionalized by including functional groups (e.g., hydrophobic or hydrophilic groups) as part of the polymer dots' surfaces. Polymer dots can be used as a fluorophore (e.g., a detectable agent), and, thus, polymer dots can be bioconjugated or linked or cross-linked to biomolecules via a functional group on the polymer dot (e.g., through the use of click chemistry). Polymer dots can be conjugated to an antibody, aptamer, nucleic acid, or other affinity tag or linker, which can, in turn, be directed to a molecule such as a biomolecule (e.g., a synthetic or naturally occurring protein, glycoprotein, peptide, amino acid, metabolite, drug, toxin, nuclear acid, nucleotide carbohydrate, sugar, lipid, fatty acid, or the like). A polymer dot can be a nanoparticle with critical dimensions (e.g., the nanoparticle's radius or diameter) of 50 nm or less, 30 nm or less, 25 nm or less, 20 nm or less, 15 nm or less, 10 nm or less, or 5 nm or less.

Methods of de-labeling of a detectable agent comprising a polymer dot can include the use of a fluorescence quencher, such as Black Hole Quencher. Methods of de-labeling of a detectable agent comprising a polymer dot can also include the use of an applied voltage, or the use of an applied voltage in combination with a fluorescence quencher.

Fluorescent detectable agents can comprise non-protein organic fluorophores such as derivatives of xanthenes, cyanines, squaraines, naphthalenes, coumarins, oxadiazoles, anthracenes, pyrenes, oxazines, acridines, arylmethines, and tetrapyrroles. Fluorescent detectable agents can include rhodamine, eosin, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7 and other cyanine derivatives (e.g., PE-Cy5.5, PE-Cy7, APC-Cy7, etc.), peridinin and its derivatives (e.g., PerCP, PerCP 5.5), oxadiazole derivatives, pyridyloxazole, nitrobenzoxadiazole, benzoxadiazole, pyrene derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ Rho 101, ATTO™ 590, ATTO™ 633, ATTO™ 647N, other derivatives of ATTO dyes, TYE™ 563, TYE™ 665, or TYE™ 705, Q570, boron dipyrromethene (BODIPY) dyes (such as BODIPY FL $C_5$, BODIPY FL $C_5$, BOPIDY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, and BODIPY 650/655), CF610, Propidium iodide, Q670, Indocyanine green, Pacific Blue dye, Pacific Green dye, Pacific Orange dye, Hoeschst stains or any derivative thereof.

In some embodiments, the fluorophore is a fluorescent agent emitting electromagnetic radiation at a wavelength between 350 nm and 1500 nm, such emissions being used to detect such agent. Non-limiting examples of fluorescent dyes that could be used to label, e.g., a conjugating molecule, antibody tag, genetically encoded fusion protein, or genetically encoded fluorescent protein can include fluorescent proteins and any derivative thereof (e.g., green fluorescent protein (GFP), enhanced green fluorescent protein (eGFP), RoGFP, fluorescein isothiocyanate (FITC), Clover, yellow fluorescent protein (YFP), blue fluorescent protein (BFP), cyan fluorescent protein (CFP), red fluorescent protein (RFP)), Discosoma sp. red fluorescent protein (dsRed), synapto-pHluorin, and m isoform proteins and any derivative thereof (such as, for example, mCherry, mStrawberry, mKate2, mEmerald, and mNeonGreen). Similarly, dyes such as Hoeschst stains and any derivative thereof can be used to label cells and molecules of interest. In some aspects, near infrared dyes often include cyanine dyes. Additional non-limiting examples of fluorescent labels for use as a conjugating molecule in the present disclosure include acridine orange or yellow, Alexa Fluors and any derivative thereof, 7-actinomycin D, 8-anilinonaphthalene-1-sulfonic acid, auramine-rhodamine stain and any derivative thereof, bensanthrhone, bimane, 9-10-bis(phenylethynyl)anthracene, 5,12-bis(phenylethynyl)naththacene, bisbenzimide, brainbow, calcein, carbodyfluorescein and any derivative thereof, 1-chloro-9,10-bis(phenylethynyl)anthracene and any derivative thereof, hetamethine dye and any derivative thereof, DiOC6, DyLight Fluors and any derivative thereof, VivoTag and any derivative thereof, ZQ800, indocyanine green (ICG), epicocconone, ethidium bromide, FlAsH-EDT2, Fluo dye and any derivative thereof, FluoProbe and any derivative thereof, Fluorescein and any derivative thereof, Fura and any derivative thereof, GelGreen and any derivative thereof, GelRed and any derivative thereof, iminocoumarin, indian yellow, indo-1 and any derivative thereof, laurdan, mercocyanine and any derivative thereof, nile dyes and any derivative thereof, perylene, phloxine, phyco dye and any derivative thereof, propidium iodide, pyranine, rhodamine and any derivative thereof, ribogreen, rubrene, stilbene and any derivative thereof, sulforhodamine and any derivative thereof, SYBR and any derivative thereof, tetraphenyl butadiene, tetrasodium tris, Texas Red, Titan Yellow, TSQ, umbelliferone, violanthrone, YOYO-1, TOTO and any derivative thereof, lipophilic dyes (e.g., 3,3'-Dioctadecyloxacarboncyanine perchlorate), and fluorescent polymer dots and quantum dots. Other suitable fluorescent labels include, but are not limited to, tetramethylrhodamine (TRITC), fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), calcein, 7-aminoactinomycin D (7-AAD), 4',6-diamidino-2-phenylindole (DAPI), carbocyanine, merocyanine, styryl dyes, oxonol dyes, phycoerythrin and any derivatives thereof, erythrosin, eosin, allophycocyanin (APC) and any derivative thereof, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514., etc.), Texas Red, Texas Red-X, SPECTRUM RED, SPECTRUM GREEN, ALEXA FLUOR™ dyes and their derivatives (e.g., ALEXA FLUOR 350, ALEXA FLUOR 488, ALEXA FLUOR 532, ALEXA FLUOR 546, ALEXA FLUOR 568, ALEXA FLUOR 594, ALEXA FLUOR 633, ALEXA FLUOR 660, ALEXA FLUOR 680, etc.), IRDyes (e.g., IRD40, IRD 700, IRD 800, etc.), and the like.

In some embodiments, biotin conjugates that can act both as a detectable label and an affinity handle for secondary labels or purification can be used. Non-limiting examples of commercially available fluorescent biotin conjugates include Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, Alexa Fluor 488 biocytin, Alexa Fluor 546, Alexa Fluor 549, lucifer yellow, cadaverine, biotin-X cadaverine, Lucifer yellow biocytin, Oregon green 488 biocytin, biotin-rhodamine and tetramethylrhodamine biocytin. In some other examples, the conjugates can include chemiluminescent compounds, colloidal metals, luminescent compounds, enzymes, radioisotopes, and paramagnetic labels.

In some embodiments involving expression of detectable agents from a nucleic acid sequence, detectable agents (e.g., labels) can either take the form of a fusion protein, in which the label is physically connected to one or more proteins translated from RNA or to one or more proteins transcribed from DNA or cDNA and then translated from mRNA, or they can take the form of a separate protein, which is produced in the cell from RNA, DNA, or cDNA either in conjunction with another gene or gene segment (for example, separated by a 2A skip sequence) or on its own and is not physically connected to another protein immediately after it is created.

In some embodiments, the labeled protein can be incorporated into the structure of an organelle or other cellular structure or molecular complex, thus specifically labeling that organelle, structure, or complex. In other embodiments, the labeled protein is not permanently incorporated into any organelle, structure, or complex but can be associated with or otherwise temporarily incorporated into one or more organelle, structure, or complex for the purpose of qualitative or quantitative analysis involving those organelles, structures, or complexes. In other embodiments, free labels produced during the same transcription or translation event as the protein of interest can be evaluated quantitatively or qualitatively to assess the presence or extent of pathway activity.

Molecules of Interest

A molecule of interest can be a molecule in a sample that is to be detected, for example, by labeling the molecule of interest with a detectable agent. A cell can comprise a molecule of interest or a plurality of molecules of interest. A molecule of interest can comprise an unbound molecule or a molecule associated with a substrate or a cellular structure.

Molecules of interest can be molecules contained within a cell or they can be associated with the surface of a cell or they can be molecules secreted from the cell and captured onto the substrate. Molecules of interest can comprise a peptide, a functional protein, a non-functional protein, a lipid, an antibody, a cytokine, an organic or inorganic compound, or a nucleic acid. A nucleic acid can comprise DNA or RNA or a nucleic acid complex (e.g., double-stranded DNA, DNA/RNA hybrids, protein/DNA complexes, and protein/RNA complexes). A nucleic acid can also include non-coding RNA, such as transfer RNAs (tRNAs), ribosomal RNAs (rRNAs), snoRNAs, microRNAs, siRNAs, snRNAs, exRNAs, piRNAs, and scaRNAs.

Molecules of interest can be produced by a cell (e.g., proteins produced by immune cells), including the cell being examined, or they can be artificially created molecules or products of artificially created molecules. For example, molecules of interest can be synthesized oligonucleotides or nucleic acid plasmids. A molecule of interest (and, in certain embodiments, a detectable agent), can be produced from a nucleic acid plasmid. In some cases, molecules of interest can be isolated and used in the methods and systems described herein. A non-limiting example of such an embodiment can be a motility experiment in which a lawn of myosin molecules immobilized on a substrate while fluorescently-tagged actin filament molecules are allowed to translate over the myosin molecules.

Labeling a molecule with a detectable agent can provide a means of quantification or qualitative analysis of the molecule or molecules of interest. Detection and/or analysis of molecules of interest (e.g., through a detectable agent used to label the molecule of interest) can be performed to determine a plurality of experimental or clinical parameters, including molecular concentrations, persistence of molecules, spatial localization of molecules, colocalization or aggregation of molecules, metabolism of molecules, binding or inhibition of molecules, modification of a molecule (e.g., phosphorylation, dephosphorylation, ubiquitination, SUMOylation, glycation, alkylation, amidation, deamidation, glycosylation, oxidation, esterification, methylation, etc.), expression or production level of a molecule, cleavage or metabolism of a molecule, and changes in such parameters over time and/or with respect to other molecules.

A non-limiting list of molecules of interest, which can be labeled with a detectable agent (e.g., an antibody conjugated to a fluorescent detectable agent), includes 4-1BB Ligand (CD137L), CD221 (IGF-1R), Aiolos, CD223 (LAG-3), anti-His Tag, CD226 (DNAM-1), Arginase I, CD227 (MUC-1), BrdU, CD228 (MFI2, MTF1), CD1a (T6), CD229 (Ly-9), CD1b, CD231 (TALLA), CD1c, CD235a (Glycophorin A), CD1d, CD235ab (Glycophorin A/B), CD2 (LFA-2), CD243 (ABCB1), CD3 (T3), CD243 (MDR-1), CD3c, CD244 (2B4), CD4 (T4, L3T4), CD252 (OX-40L, CD134L), CD5, CD253 (TRAIL), CD6 (T12), CD255 (TWEAK), CD7 (gp40), CD257 (BAFF, BLYS), CD8a (T8, Leu2), CD258 (LIGHT), CD9 (Tetraspanin), CD261 (DR4, TRAIL-R1), CD10 (CALLA), CD262 (DR5, TRAIL-R2), CD11a (integrin αL), CD263 (DcR1, TRAIL-R3), CD11b (integrin αM), CD266 (Fn14/TWEAK Receptor), CD11c, CD267 (TACI), CD11c (integrin αX), CD268 (BAFFR, BAFF-R), CD13 (gp150, APN), CD269 (BCMA), CD14, CD271 (NGFR), CD15 (Lewis X), CD272 (BTLA), CD16 (FCγRIII), CD273 (B7-DC, PD-L2), CD18, CD274 (B7-H1, PD-L1), CD18 (integrin β2), CD275 (ICOSL, B7H2, B7-H2), CD19 (B4), CD275 (B7-H2, B7-RP1, ICOSL), CD20 (Bp35, B1), CD276 (B7-H3), CD21 (CR2, C3dR), CD277, CD22 (Siglec-2), CD278 (ICOS), CD23, CD279 (PD-1), CD24 (Heat Stable Antigen), CD281 (TLR1), CD25 (IL-2Ra), CD282 (TLR2), CD26 (DPP IV ectoenzyme), CD283 (TLR3), CD27 (S152, T14), CD284 (TLR4), CD28 (T44, Tp44), CD290 (TLR10), CD29 (integrin β1), CD294 (CRTH2), CD30 (Ki-1, Ber-H2), CD286 (TLR6), CD31 (PECAM-1), CD300c, CD32 (FCγRII), CD298, CD33 (Siglec-3), CD300e (IREM-2, CMRF35-A5), CD34, CD300F (IREM-1), CD35, CD301 (CLEC10A), CD36 (gpIIIb, gpIV), CD303 (BDCA-2), CD36L1 (SCARB1, SR-BI), CD304 (Neuropilin-1), CD37, CD305, CD38 (T10), CD307 (FcRL5), CD39 (NTPDase-1), CD309 (VEGFR2), CD40 (BP50), CD314 (NKG2D), CD40 Ligand (CD154), CD317 (BST2, Tetherin), CD41/CD61, CD318 (CDCP1), CD41 (gpIIb), CD319 (CRACC), CD41b, CD321 (F11R), CD42b (gpIbα), CD323 (JAM3), CD43 (Leukosialin), CD324 (E-Cadherin), CD44 (Hermes, Pgp-1), CD325 (N-Cadherin), CD45, CD326 (Ep-CAM), CD45 (LCA, T200), CD328 (Siglec-7), CD45R (B220), CD334 (FGFR4), CD45RA, CD335 (NKp46), CD45RB, CD336 (NKp44, NCR2), CD45RO, CD337 (NKp30, NCR3), CD46, CD338 (ABCG2), CD47, CD340 (erbB2/HER-2), CD48 (Blast-1), CD344 (Frizzled-4), CD49a (α1 integrin), CD349 (Frizzled-9), CD49b (a2 integrin), CD351, CD49c (α3 integrin), CD357 (GITR), CD49d (a4 integrin), CD360 (IL-21R), CD49e, CD365 (Tim-1), CD49e (c5 integrin), CD366 (Tim-3), CD49f (α6 integrin), CD369 (Dectin-1/CLEC7A), CD50 (ICAM-3), CD370 (CLEC9A/DNGR1), CD51, CD371 (CLEC12A), CD51/61 (α(V)/β(3) integrin), β2-microglobulin, CD52 (CAMPATH-1), 4-1BB (CDw137), CD53 (OX44), 4-1BBL (CDw137L), CD54, A2B5, CD55 (Decay Accelerating Factor), APCDD1 (DRAPC1), CD56 (NCAM), B7-H2 (ICOSL, B7H2, CD275), CD57, B7-H4, CD58, Bcl-6, CD59 (Protectin, H19), BrdU (Bromodeoxyuridine), CD61 (β3 integrin), Cadherin 11, CD62E (E-Selectin), C3AR, CD62L (L-Selectin), C5L2, CD62p (P-Selectin), CCL11, CD63, CCR8, CD64 (FCγRI), CCR10, CD66a/c/e, CLECiB (CLEC2), CD66b (CD67), CLEC4A, CD68, CLEC4D, CD69 (Very Early Activation Antigen), CLEC5A, CD70, CRTAM, CD71 (Transferrin Receptor), Cutaneous Lymphocyte-associated Antigen (CLA), CD72 (Lyb-2), CCX-CKR (CCRL1), CD73, CX3CR1, CD74 (MIF Receptor), CXCL5, CD75 (Lactosamines, CDw75), CXCL9 (MIG), CD77, CXCL16, CD79a, CXCR7, CD79b, DcR3 (Decoy Recptor 3, TR6), CD80 (B7-1), Delta Opioid Receptor, CD81 (TAPA-1), Dopamine Receptor D1 (DRD1), CD82, DR3 (TRAMP), CD83 (HB15), EGFR, CD84 (Ly9b), EGFR Phosphorylated (Tyr1068), CD85a (ILT5), EphA2, CD85d (ILT4), erbB3/HER-3, CD85g (ILT7, ILT-7), ERK1/2 Phospho (Thr202/Tyr204), CD85h (ILT1), FcεRIa, CD85j (ILT2), FcRL4, CD85k (ILT3), FcRL6, CD86 (B7-2), FOXP3 (Forkhead box protein P3), CD87 (uPA-R), FPR3 (FPRL2), CD88 (C5aR), Galectin-3 (Mac-2), CD89, Galectin-9, CD90 (Thy-1), Ganglioside GD2, CD92, GARP (LRRC32), CD93, GFP, CD94 (KP43), GITR (TNFRSFi8, AITR), CD95 (Fas, APO-1), GL7, CD96 (TACTILE), GPR19, CD97, GPR56, CD98 (4F2), GPR83, CD99, GPR183 (EBI2), CD99 (E2 antigen), Granulysin, CD99 (Ewings Sarcoma Marker), Granzyme A (CTLA-3), CD100, Granzyme B, CD101, Granzyme K, CD102 (ICAM-2), HLA-A2, CD103 (Integrin αIEL), HLA-A,B,C (MHC Class I), CD104 (integrin β4), HLA-B7, CD105 (Endoglin), HLA-DM, CD106 (VCAM-1), HLA-DQ, CD107a (LAMP-1), HLA-DRB 1, CD107b (LAMP-2), HLA-DR, DP, CD108 (H-SEMA, SEMAL), HLA-DR, DP, DQ, CD109, HLA-DR (MHC Class II), CD111 (Nectin-1), HLA-E, CD112 (Nectin-2), HRF, CD114 (G-CSFR), HVEM (TR2), CD116 (GM-CSFRα), IFN-γ R β chain, CD117 (c-kit), Ig light chain κ, CD119 (IFN-γRa), Ig light chain λ, CD120b, IgD, CD122 (IL-2R1), IgE, CD123 (IL-3Rα), IgM, CD124 (IL-4Rα), Ikaros, CD126 (IL-6Rα), IL-22, CD127 (IL-7Rα), Integrin β7, CD129 (IL-9R), IRF2, CD130 (gp130), KIR2DL2/L3 (NKAT2), CD131 (IL-3R common β), KIR3DL1 (NKB1), CD132 (common γ chain), KLRG1 (MAFA), CD134 (OX40), LAMP5, CD135 (Flt-3/Flk-2), LAP (TGF-β1), CDw137L (4-1BBL), LOX-1, CD137 (4-1BB), Lymphotoxin 3 Receptor (LT-R), CD138 (Syndecan-1), LY6G6D, CD140a (PDGF-Ra), M-CSF, CD140b (PDGF-R3), Mast Cell Tryptase, CD141 (Thrombomodulin), MERTK, CD142, MICA/MICB, CD143 (Angiotensin-converting enzyme), MR1, CD144 (VE-Cadherin), MRGX2, CD146, MRP1 (ABCC1), CD147 (Neurothelin), MRP-14 (S100A9), CD148, MS4A4A, CD150 (SLAM), MUC-13, CD151 (PETA-3), Notch 1, CD152 (CTLA-4), Notch 2, CD154 (CD40 Ligand), Notch 4, CD155 (PVR, NTAL (LAT2), CD156c (ADAM10), NTB-A (NTBA), CD158, PCNA (Proliferating Cell Nuclear Antigen), CD158b (KIR2DL2/L3, NKAT2), Perforin, CD158e1 (KIR3DL1, NKB1), Phosphotyrosine, CD158f (KIR2DL5), PNAd, CD160, Podoplanin, CD161, ROR1, CD162, S100A4, CD163, SCIMP, CD164 (MUC-24, MGC-24), SEMA4A, CD166, Sialyl Lewis X (dimeric), CD167a (DDR1), Siglec-9, CD169 (Sialoadhesin, Siglec-1), SIT, CD170 (Siglec-5), SSEA-1, CD171, SSEA-3, CD172a (SIRPα), SSEA-4, CD172b (SIRPβ), SSEA-5, CD172a/b (SIRPα/β), STAT2, CD172g (SIRPγ), STRO-1, CD177 (NB1), T-bet, CD178 (FasL/CD95L), TACSTD2 (TROP2), CD179b (Ig λ5), TCL1, CD180 (RP105), TCR Vα7.2, CD181 (CXCR1), TCR Vα24, CD182 (CXCR2), TCR Vα24-Jα18 (iNKT cell), CD183 (CXCR3), TCR Vβ1, CD184 (CXCR4, Fusin), TCR Vβ5, CD185 (CXCR5), TCR Vβ5 Related, CD186 (CXCR6), TCR Vβ7.1, CD191 (CCR1), TCR Vβ8, CD192 (CCR2), TCR Vβ13.1, CD193 (CCR3), TCR Vδ2, CD194 (CCR4), TICAM-1 (TRIF), CD195 (CCR5), TIGIT (VSTM3), CD195 (CCR5) Phosphorylated (Ser349), Tim-4, CD196 (CCR6), TLT-2, CD197 (CCR7), TM4SF20, CD199 (CCR9), TMEM8A, CD200 (OX2), TSPAN33, CD200 Receptor, TRA-1-60-R, CD201

(EPCR), TRA-1-81, CD202b (Tie2/TEK), TRA-2-49, CD203c (E-NPP3), TRA-2-54/2J, CD204, TREM-1, CD206 (MMR), TSLPR (TSLP-R), CD207 (Langerin), TSPAN8, CD209 (DC-SIGN), TWEAK (Apo-3 Ligand, DR3-L), CD210 (IL-10R), uPA (PLAU), CD213α1(IL-13Rα1), VEGF-165, CD213a2 (IL13Rα2), VEGFR-3 (FLT-4), CD217, Veri-Cells™ CD4-Low PBMC, CD217 (IL-17AR), Veri-Cells™ PBMC, CD218a (IL-18Rα), ZAP-70, CD220

In some respects, labeling a molecule can be considered labeling a cell, as detection of the molecule can provide information regarding the cell in which it is contained or with which it is associated. For example, a detectable agent used to identify a given protein can be used to track a cell's movement, to evaluate a cell's phenotype, to quantify a cell's proliferation rate, or a wide range of other biological metrics that will be apparent to a person skilled in the art.

Cells and Cellular Modification

A cell can be used in the methods and systems of this disclosure, and the cell can be eukaryotic or prokaryotic and can be derived from any species. The cells can be labeled, detected, de-labeled, stimulated, fixed, permeabilized, crosslinked to gels then washed, and/or lysed using the methods and systems of this disclosure. Cells can be primary, immortalized, or engineered cells of any phenotype or genotype. For example, cells can be derived from patients (e.g., white blood cells) or from established cell lines, which include stem cell lines such as induced pluripotent stem cell lines. The genotype and/or phenotype of a cell used in the methods and systems described herein can be representative of an abnormal condition and can be selected for that reason. Cells used in the disclosed methods and systems can also be cells derived from a patient-derived cell or an established cell line, such as cells differentiated from a stem cell. Cells used in the disclosed methods and systems can also comprise a plurality of cells (e.g., two or more individual cells in culture or a biological tissue).

Cells used in the methods and systems described herein can be cultured directly on the substrate (either in the wells of the substrate or on its surface, if the substrate is planar). Cells used in the methods and systems described herein can be immobilized or otherwise associated with the substrate for analysis (either in the wells of the substrate or on its surface, if the substrate is planar). Cells can be situated on a substrate such that they are spatially ordered on the substrate (e.g., a periodic array, which can be grown, for example, by depositing matrix proteins or molecules on specific sections of the substrate), or can be immobilized, for example, by attaching each cell to a sticky patch (e.g., a patch or area of the substrate that has been coated with one or more matrix proteins or molecules or that has been plasma-treated or that has been otherwise treated to potentiate or promote adhesion by the cell or molecule) or by placing each cell in a well of an array of patches or wells. Cells can be spatially unordered on the substrate (e.g., a random array). Cells associated with a substrate or grown on a substrate, as in a random array, can be labeled or de-labeled when they cover at least 20%, at least 30%, at least 40%, at least 50%, at least 60%, at least 70%, at least 80%, at least 90%, or at least 100% of the area of the substrate or confluence (e.g., coverage of the sample area of the substrate).

Cells used in the methods and systems described herein can be live or fixed. Fixation of cell can comprise the use of aldehydes (e.g., glutaraldehyde, formaldehyde, and paraformaldehyde), ethanol, methanol, formalin, acetone, or picrates, among other fixatives. Fixatives can be used alone, in combination with one another, and/or in combination with other reagents, such as buffering agents. The methods and systems described herein can also comprise various experimental interventions following procurement of primary cells from a patient and/or culture of cellular components and prior to detection of detectable agents. Cells can be chemically fixed or cryogenically treated prior to detection of detectable agents. In some embodiments, cells can be fixed and enzymatically or mechanically removed from culture or dissociated from a tissue (or removed from culture or dissociated from a tissue first and then fixed) prior to be subjected to one or more methods of detection (e.g., microscopy, flow cytometry, mass spectrometry, etc.). Cells can be permeabilized prior to detection using a permeabilization agent (e.g., detergents such as Triton X-100, Tween 20, saponin, organic solvents such as methanol and acetone, etc.). Cells can be stimulated to secrete proteins or activate certain pathways prior to detection. Cells can be crosslinked to a gel material such that the cellular components (e.g., proteins and nucleic acids) are crosslinked to the gel, thus preserving the number of cells and cellular components and their spatial locations, prior to labeling, detection, and de-labeling. Optionally, the cells and/or cellular components can be washed to remove certain other cellular components (e.g., lipids or enzymes). If additional detectable agents are to be used to label cells (e.g., detectable agents associated with affinity tags such as antibodies conjugated, fused, or otherwise associated with a detectable agent), the additional detectable agents may be added to the cells before or after permeabilization. If a given detectable agent is on the cell's surface or if the detectable agent is produced inside of the cell, permeabilization may not be required.

Cells can be cultured on a substrate in monolayer culture. Cells can be part of a tissue biopsy from a patient or a tissue slice from an animal. The cells can be labeled, detected, de-labeled, stimulated, fixed, crosslinked to gels, or lysed on the substrate. All fluids and reagents can be delivered to the cell or substrate by a flow cell (e.g., a microfluidic device), and the processes for delivering these fluids and reagents can be automated.

Detection of Detectable Agents

A molecule of interest can be detected by detecting an associated detectable agent. Various detectors can be used to detect a given detectable agent, the selection of which can depend upon the identity and nature of the detectable agent being detected. For example, a detectable agent can be detected by an optical detector. In some embodiments, a fluorescent detectable agent can be detected by a flow cytometer. In other embodiments, a fluorescent detectable agent can be detected by a microscope. In other embodiments, a fluorescent detectable agent can be detected by a camera. Detection of a detectable agent can be performed before, after, or during the process of labeling or de-labeling a cell or molecule of interest.

A detectable agent can be detected by using a microscope. Furthermore, the presence or absence of a detectable agent can be detected by optical microscopy. The microscopy can be fluorescence microscopy. Fluorescence microscopy can be one-photon or two-photon or multi-photon imaging. Furthermore, microscopy can be used to detect the localization of a detectable agent in an organelle or plasma membrane of a cell. For example, microscopy can be used to detect a fluorophore localized in the nucleus of a cell.

The spatial resolution of data recorded by a detector can be improved through the use of, for example, high powered microscope objectives, high-pixel camera image de-convolution algorithms, and optically clear imaging media (e.g., mounting media and suitable objective oils). In this way, resolution of detection can be as little as 5 micrometers, 4 micrometers, 3 micrometers, 2 micrometers, 1 micrometer, 0.5 micrometers, 0.25 micrometers, 0.1 micrometers, or less.

Detection of cells harboring fluorescent labels (e.g., fluorescent detectable agents) can comprise stimulating cells in micro-titer plate vessels or in microfluidic devices or on a substrate with light of a wavelength capable of exciting the fluorophore such that it emits photons within that fluorophore's theoretical emission spectrum and recording those emitted photons using an optical detector. Detection of cells harboring fluorescent labels while in culture or in a tissue can occur at any point over the course of their time in culture or in a tissue and can occur multiple times during experimentation (e.g., when observing changes in cells or their behavior over a time course). Detection of cells harboring fluorescent labels while associated with a substrate also can occur at any point over the course of their time associated with the substrate and can occur multiple times during experimentation.

The methods and systems described herein allow for high sensitivity detection of detectable agents. In some embodiments, using the methods and systems described herein, it may be possible to detect as few as 10,000 detectable agent molecules, 5,000 detectable agent molecules, 1,000 detectable agent molecules, 500 detectable agent molecules, 100 detectable agent molecules 50 detectable agent molecules, 10 detectable agent molecules, or even down to 1 detectable agent molecule in a given detector channel. In some embodiments, the amount of detectable agent that can be detected can be less than 1 ng, less than 100 pg, less than 10 pg, less than 1 pg, less than 100 fg, less than 10 fg, less than 1 fg, less than 100 ag, less than 10 ag, less than 1 ag, less than 100 zg, less than 10 zg, less than 1 zg, or less than 0.1 zg.

Multiple types of detectable agent can be used in ultrafast labeling, de-labeling, cyclic ultrafast labeling, or multiplexed ultrafast labeling. In this respect, the number of detectable agents (as opposed to the number of detectable agent molecules, which can refer to individual particles or molecules instead of different classes or types of detectable agent) that can be used simultaneously in the methods and systems described herein can be 1, at least 2, at least 3, at least 4, at least 5, at least 6, at least 7, at least 8, at least 9, at least 10, at least 11, at least 12, at least 13, at least 14, or at least 15. Different types of detectable agent can produce different signal spectra, which can have different intensities over different wavelength ranges. By coordinating selection of the types of detectable agents used in a single round of ultrafast labeling (either independent of any other experimentation or in coordination with other steps or rounds of ultrafast cyclic imaging), each detectable agent can be detected and distinguished from the other detectable agents that have been used at the same time or, if necessary, in previous rounds of labeling. In some embodiments, a quenching agent can be withheld during de-labeling of a sample that has been labeled with a detectable agent that requires a quenching agent for de-labeling. For example, in situations in which one or more molecule of interest is to be detected in one or more subsequent round of cyclic fluorescence imaging (e.g., in multiple rounds of detection separated by at least one step of de-labeling), one or more detectable agent out of a plurality of detectable agents selected to label the one or more molecule of interest that will be detected in one or more subsequent round of cyclic fluorescence imaging can be selected based on its relative resistance to voltage-based de-labeling. A non-limiting example can include using a detectable agent that requires a quenching agent for de-labeling to label a molecule that will be detected in more than one round of detection and withholding the required quenching agent in the intervening de-labeling step, allowing that molecule to remain labeled when other molecules labeled with a detectable agent (e.g., a detectable agent that is known to be sensitive to voltage-based de-labeling) are de-labeled. Such usage of a detectable agent that requires a quenching agent for de-labeling can be included, for example, in some embodiments in which the cell or molecule of interest are to be tracked from round to round. Therefore, coordination of the types of detectable agent(s) to be used in subsequent rounds of labeling can be coordinated with the types of detectable agents that have not been de-labeled or that have not been completely de-labeled in previous rounds of de-labeling.

Provisions to maximize detection sensitivity can be incorporated into a system for measuring and recording detectable agent signals. For example, ambient light from the sample and detector during detection, samples after they are contacted with detectable agent, using blocking buffers and reagents, and limiting autofluorescence by, for example, avoiding the use of fixatives and autofluorescent matrices.

Substrates

Various aspects of the present disclosure include providing a substrate with which a cell can be associated and where the cell can be labeled, de-labeled, and/or detected and which can improve the efficiency of the processes of labeling and de-labeling cells. The cells associated with the substrate can also be heated, cooled, have a voltage applied to them, and be subjected to fluid flow moving relative to the cells (e.g., via fluid flowing in a channel or via shaking or agitation of the substrate). A substrate can be planar. A substrate can be a petri dish. A substrate can be part of a fluidic or microfluidic system or device, such as forming the floor of a flow channel or an array of wells. A substrate can comprise a single vessel or a plurality of vessels, and the vessels can be the wells of a culture or well plate (e.g., a micro-titer plate, a 96-well plate, or a 384-well plate). The bottom of a vessel can be flat, round, conical, pyramidal, or any suitable configuration for performing the present methods. The well cross section can be circular, square, rectangular, triangular, trapezoidal, or any other suitable cross-sectional configuration. Increasing the concentration of an antibody or other affinity agent during labeling can increase cost, so the use of a substrate comprising wells or vessels or channels of a size requiring a minimum volume during labeling can be advantageous with respect to overall cost of labeling. The use of a fluidic or microfluidic device for introduction of an affinity agent can reduce the volume needed during labeling and can increase speed of labeling since the solution can be exchanged rapidly and via automated workflows. The presence of fluid flow (e.g., movement of fluid relative to the cell) can also facilitate labeling and/or de-labeling of the cells.

The association of a cell or molecule of interest with a substrate can comprise cellular adhesion, cross-linking, antibody-mediated capture, covalent bonding, non-specific absorption, or fluidically-induced association (e.g., via positive or negative fluidic pressure), mechanically-induced association (e.g., through agitation or centrifugation), electrically-induced association (e.g., through electrophoresis or dielectrophoresis or a combination thereof), or magnetically-induced association (e.g., through the use of magnetic materials or particles). Association of a cell or plurality of cells with a substrate can comprise general adhesive, gravitation, centrifugation, fluid flow, fluidic pressure, friction, or surface tension forces (e.g., a tissue placed on a substrate rather than having been grown on the substrate), or electrical or di-electrical or magnetic forces. Association of a sample, such as a cell, tissue, or molecule, with a substrate can be temporary (e.g., a tissue placed on a substrate), permanent (e.g., an adherent cell crosslinked to the substrate), or conditional (e.g., an unfixed adherent cell requiring divalent ions to remain attached to the substrate).

A substrate can comprise a single-cell array (FIG. 21). The single-cell array can be a regular array or a random array. Embodiments of the systems and methods of the present disclosure comprising a regular array can be arranged in periodic fashion. Random arrays can comprise coverage of at least 30%, at least 40%, at least 50%, at least 60%, at least 70%, at least 80%, at least 90% of the adhesion area.

Use of the single-cell arrays of the present disclosure, in some aspects, involves a method comprising the steps of; containment or physical trapping or surface attachment of single cells as the cells are transported in a liquid phase, and following the flow path of this phase, transiting to a physically defined position, and residing in the defined position due to the ensuing flow based forces or surface adhesive forces. In another case, the cells are trapped sequentially as the fluidic flow path is serial with respect to inlet to outlet. In another case, multiple fluid flow paths and commensurate multiple single cells are trapped/sequestered in a parallel manner, due to the numerous flow paths that can simultaneously be experienced by the cells between the inlet and outlet. In some cases, the array can have chambers with a variety of potential dimensions and shapes and surface properties. The dimensions and shapes and surface properties can affect the parallel flow trap design. In some aspects, the chambers of the device can be wells. The device can trap single particles/cells from a solution (e.g., such as beads, cells, etc.) and multiple wells can be arranged in parallel to form the device.

In some aspects, the single-cell array can be used with methods known to those of skill in the art for analysis of nucleic acids. In some aspects, the analysis of nucleic acids can include fluorescence in-situ hybridization (FISH) or polymerase chain reaction (PCR). In the case of performing PCR using the single-analyte array, all the chambers can be filled with a single analyte in a fluid. Each chamber can be sealed (e.g., using oil) and PCR can be performed on each single analyte in parallel. Analytes contained in the individual wells or chambers of the single-analyte array can be detected using a variety of techniques. For example, the analytes in the wells or chambers can be imaged using microscopy. In some aspects, microscopy can include bright field microscopy. In some aspects, microscopy can include fluorescence microscopy. In any case of microscopy, the sample can be placed on a stage. In some aspects, the stage can be manually operated. In other cases, the stage can be an automated translation stage that can be controlled by computer programs. In any case of microscopy, images can be acquired by CCD cameras.

Substrates can comprise a coated surface or an uncoated surface or a patterned surface, either with a chemical pattern (e.g., period array of adhesive patches) or topographical pattern (e.g., periodic array or raised or recessed regions or wells), the choice of which can be informed by the cell or molecule to be provided on the substrate. A coating can comprise a chemical, a biomolecule, a nucleic acid, a protein, a capture agent, a peptide, a lipid, a carbohydrate, a gel, a polymer, a conductor, a semiconductor, a non-conductor, an organic molecule, or an inorganic molecule. A substrate material or substrate coating can be selected for its ability to either repel or anchor a cell (e.g., gelatin, fibronec-tin, vitronectin, collagen, laminins, aggrecan, osteonectin, elastin, fibrinogen, fibrillin, tenascin, or other extracellular matrix compounds). The material(s) of which a substrate or its coating consists can be selected for characteristics that allow the system to repel or to capture desired molecules associated with or secreted from a cell. A substrate can be a film, and the substrate can comprise a conductor, such as graphene. A substrate can also have topographical patterning.

The substrate can be designed to promote cellular adhesion or it can employ a different mechanism for immobilizing a cell on its surface. For example, a substrate with a hole (or a plurality of holes) connected to a source of suction or fluidic pressure can be used to immobilize a live or fixed cell at the hole by drawing negative fluidic pressure (e.g., a vacuum) through the hole when the cell is present. The substrate can be designed to maximize capture of molecules associated with or secreted from a cell; or it can be designed to minimize non-specific binding of molecules associated with or secreted from a cell, for example, through physical configuration (e.g., geometries in the flow channel of a microfluidic device or topographical features of the substrate), selection of appropriate materials from which to derive the substrate and/or its coating (e.g., specific adhesion proteins localized to areas of the substrate or covering the culture area, or hydrophobic or hydrophilic surface chemistry or hydrogels), or functional capabilities, such as a means of suction or fluid pressure (e.g., negative or positive pressure).

A substrate itself can comprise a metal, a metal alloy or a non-metal and can be designed to enhance or modify an electric field or applied voltage, relative to a cell. A substrate can also be designed such that it has little effect on an electric field or applied voltage (e.g., a substrate made of a non-conducting, non-magnetic material). The substrate can also be designed comprising conductive materials that help to shape or administer a voltage or electric field applied to the cells, performed measurements (e.g., measurements of cellular proliferation or migration) and/or to deliver stimulation (e.g., for modifying cellular phenotype or for technical purposes such as electroporation). A substrate can comprise a magnet (e.g., a permanent magnetic or electromagnet) for purpose of creating or modifying a voltage or electric field or for the purpose of applying a molecule (e.g., an affinity tag comprising a magnetic tag) to a cell or molecule. A substrate can also comprise a means of heating the cell and/or a means of creating a voltage across the cell. A substrate can also comprise a means of measuring the temperature of or around the cell. A substrate can also comprise a means of measuring the amount of voltage or electric field applied to the cell. A substrate can also comprise a means of measuring the amount of reactive chemical species, such as reactive oxygen species, generated by the applied voltage. The substrate can also comprise a flow cell (e.g., microfluidics device) for the delivery and removal of reagents such as detectable agents and buffers. A substrate can comprise a transparent material, such as glass or a transparent plastic, to enable or enhance imaging of cells.

A substrate can be permanently attached to a detector (e.g., the tray of a bioanalyzer or a proximity detector) or it can be a removable unit. A substrate can be stackable (e.g., stackable multi-titer plates) for use in multiplexing strategies.

Flow Cell

The methods and systems of the present disclosure can also comprise a flow cell (e.g., a fluid management system) connected to the substrate. The fluid management system can comprise a flow channel used to supply a fluid to the sample cell (e.g., the biological cell's environment, such as the substrate) and/or to remove a fluid from the sample cell's environment (e.g., the biological cell's environment). The flow cell can comprise a peristaltic pump, an infusion pump, a syringe pump, a micropump (e.g., a microelectromechanical system, or MEMS pump), a vacuum pump, a mechanical pump, or a gravity pump. The flow cell can comprise a system of reservoirs, vials, tubes, valves, tubing, flow channels, and bifurcations that can either be integrated into the substrate or can be removable from the substrate or can be external to the substrate and can be used to contain reagents (such as fixatives, cell permeabilization agents, wash buffers, detectable agents, waste fluids, cell culture media, crosslinking agents, cell stimulants, capture molecules, drugs, etc.). The flow cell and its associated features (e.g., pumps and valves) can be operated by a computer processor and automated.

The fluid management system can comprise a fluidic or microfluidic system that is either permanently associated with the substrate or removable with respect to the substrate or is part of the substrate or is external to the substrate. For example, a microfluidic device can be integrated into the substrate or is part of the substrate or it can comprise a chamber created by securing an upper section onto a substrate (e.g., by suction or by a clip, screw, or other locking mechanism).

Fluids supplied to the cell by the flow cell can comprise cell culture medium, agonists, antagonists, drugs, stimulants, acids, bases, buffers, fixatives, cell permeabilization agents, capture agents, crosslinking chemicals, nucleic acid hybridization or de-hybridization agents, and detectable agents. The flow cell can be used to supply substances and solutions such as these to the cell for the purpose of culturing the cell, stimulating the cell, capturing molecules produced by the cell, fixing the cell, permeabilizing the cell, crosslinking the to a gel, embedding the cell, attaching the cell, detaching the cell, washing the cell, hydrating the cell, labeling the cell, or de-labeling the cell.

Temperature Control Apparatus

The methods and systems of this disclosure can comprise a temperature control apparatus (which can comprise a temperature-control device) for regulating the temperature of the cell and/or the fluids used in the methods and systems described herein. Thus a controlled (e.g., regulated) temperature can be applied to the cell by defining a target temperature, or temperature set point. By controlling the temperature of the sample (e.g., cells, molecules, or detectable agents), the speed at which cells, molecules, or detectable agents are labeled and/or de-labeled can be significantly improved.

In some embodiments, a plurality of temperature control devices can be used, for example, to improve uniformity of temperature across the individual vessels of a substrate. A temperature control device can be used to maintain consistent experimental conditions between samples, groups, assays, and experiments and can be used to improve either labeling or de-labeling efficiency. By increasing the temperature of a cell and an affinity tag or a detectable agent (e.g., a detectable label) during the process of labeling a cell or molecule, it is possible to decrease the amount of time required to label the cell or molecule. By increasing or decreasing the temperature of a cell and an affinity tag or detectable agent (e.g., a detectable label) during the process of de-labeling a cell or molecule, it is also possible to decrease the amount of time required to de-label the cell or molecule or to improve the efficiency or the extent with which the cell or molecule is de-labeled.

A temperature control device can comprise a heating element for increasing the temperature around a sample or of a sample (e.g., of a cell, molecule, or detectable agent). A heating element can comprise an electrical heating element, a convective heating element, an air heating element, a Peltier heating element, a resistive heating element, a combustion heating element, an induction heating element (which can be used with a substrate that comprises an induction coil or the like), a chemical heating element, or light heating element (e.g., infrared light). Selection of a heating element mechanism can be made based on the impact to applied voltages or electric fields created in the vicinity, capacity to precisely and accurately induce a prescribed temperature in a sample (e.g., a cell or molecule of interest) with little or no variation or noise, and considerations regarding suitability for a given application. A temperature control device can also comprise a cooling element for decreasing the temperature around a sample (e.g., of a cell, molecule, or detectable agent). A cooling element, for example, can comprise a Peltier device.

A temperature control device can comprise a system capable of varying temperature over time. The temperature control device or plurality of temperature control devices can be prescribed (manually or digitally) to vary the temperature of a cell, section of a cell, substrate, or section of a substrate over time, independently or in concert with other experimental conditions (e.g., the application of a voltage or electrical field, the de-labeling of a cell, the labeling of a cell, the delivery of detectable agents to the cell, or the detection of a cell and/or its associated detectable agents). In this way, heating and/or cooling of a cell, molecule, or substrate can be cyclical.

A temperature control device can also comprise a heat sink or cooling element, such as a refrigeration unit.

The temperature control device can comprise a thermocouple and/or a Peltier heat pump. The temperature control device can be used (e.g., manually or by a program executable with a computer processor) to control the temperature of a cell or molecule of interest by incorporating the temperature control device (which can comprise a means of increasing temperature, a means of detecting temperature, and/or a means of reducing temperature) into the substrate or by positioning the temperature control device in proximity to the cell or molecule of interest or by controlling the temperature around the substrate or cell of interest. Through the control feedback loop of the computer processor, a temperature detecting element such as a thermocouple, and the heating element or cooling element, the temperature of the sample (e.g., the cell, molecule, or detectable agent) can be controlled with a variation of no more than 0.25° C., no more than 0.5° C., no more than 0.75° C., no more than 1° C., no more than 2° C., no more than 3° C., no more than 4° C., or no more than 5° C., which can be measured relative to a temperature set point.

A temperature set point can be a target temperature at which experimentation (e.g., labeling, de-labeling, or detecting) is to be performed. A temperature set point can be stipulated by a programmed protocol stored in the computer's memory or it can be stipulated manually by the user (e.g., through an input interface such as a touchscreen or keyboard).

Increases to labeling efficiency through heating of a cell during labeling can be relative to a subjective reference temperature (e.g., 13 degrees Celsius above room temperature) or it can be prescribed based on a range of temperatures at a given atmospheric condition (e.g., between 30 degrees Celsius and 80° C. at one atmosphere of pressure). Therefore, the temperature control device (or plurality of temperature control devices) can be used to heat a cell or molecule of interest to temperatures of at least 26° C., at least 30° C., at least 31° C., at least 32° C., at least 33° C., at least 34° C., at least 35° C., at least 36° C., at least 37° C., at least 38° C., at least 39° C., at least 40° C., at least 45° C., at least 50° C., at least at least 55° C., at least 60° C., at least 65° C., at least 70° C., at least 75° C., or at least 80° C.

Methods of De-Labeling

In addition to labeling a cell or molecule of interest (e.g., a sample) with detectable agents, the methods and systems described herein can improve the efficiency of de-labeling a cell or molecule of interest, either as an ends of its own or as part of a cyclic fluorescent imaging protocol (e.g., as described in FIG. 3-FIG. 8).

De-labeling can include destruction of a detectable agent, chemical modification of a detectable agent (e.g., via a chemical reaction such as oxidation), disassociation of a detectable agent with a cell, molecule of interest, or affinity tag (e.g., an aptamer, antibody or nucleic acid), disassociation of the affinity tag with the detectable agent from a cell or molecule of interest, or decreasing the signal of a detectable agent either permanently or temporarily. De-labeling can include de-staining a sample, chemical reaction of a detectable agent that renders it undetectable or less detectable, photobleaching or photoquenching or photoswitching a detectable agent, or quenching a detectable agent signal with a quenching agent.

The number of different types of detectable agents that can be detected in each labeling experiment can be limited by the capabilities of the detector or detection scheme. Therefore, experimental studies requiring the analysis of cells, aspects of a cell (or cells), or molecules than can be detected at once by the detector or detection scheme will require additional experiments in which the remaining unassayed cells or molecules on the cells or molecules of interest can be measured with detectable agents. As repeating experiments with detectable agents directed to new cells or molecules of interest can be a time- and resource-intensive process, the ability to de-label and re-label a sample (e.g., a cell or molecule of interest) allows for increased efficiency of experimentation. Furthermore, reducing the time required to de-label a cell or molecule is a critical aspect of increasing efficiency of such experimentation.

Figure 3:
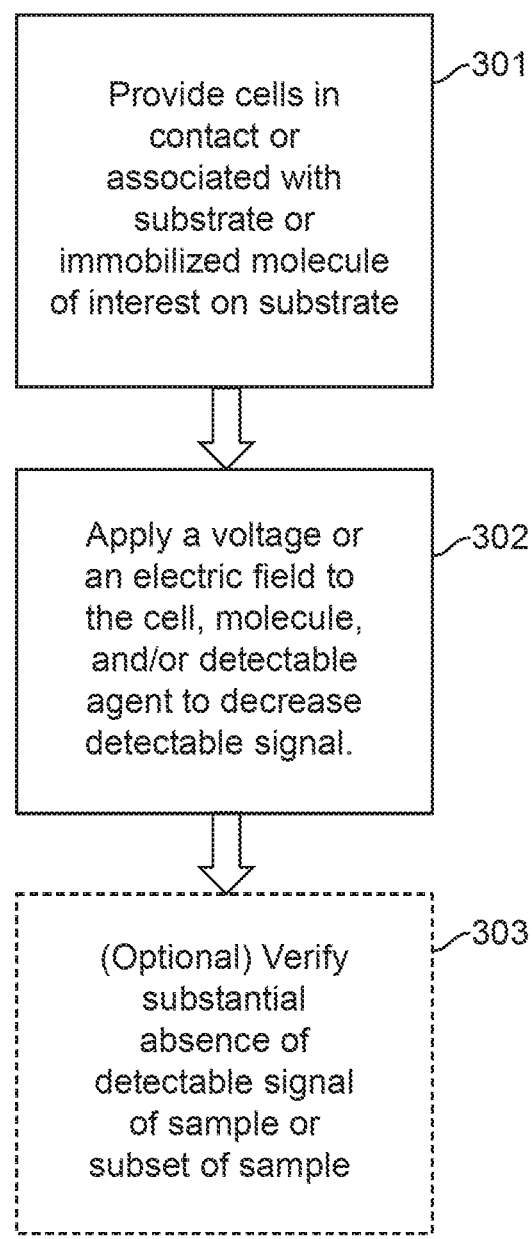
FIG. 3 shows a flow diagram of de-labeling of cells or molecules of interest. As shown, an optional step of verifying de-labeling of the detectable agent, which can comprise detecting the detectable agent signal, can be performed after de-labeling the sample (e.g., the cell or molecule of interest).

The process of ultrafast de-labeling can include the steps described in FIG. 3. Specifically, ultrafast de-labeling can include providing a cell or molecule of interest labeled with a detectable agent associated or in contact with a substrate (301), which can involve culturing or maintaining a cell in a desired state on a multi-titer plate or on a tissue culture plate. Ultrafast de-labeling can further comprise applying a voltage to the cell, molecule, or detectable agent (302), for example, with electrodes generating the voltage which are situated such that the voltage is applied across the sample, and, optionally, detecting the detectable agent, using detection methodology as described above to validate that the detectable agent signal has been diminished or is rendered absent or substantially absent (e.g., through destruction or inhibition of the detectable agent, which may occur through exposure to reactive oxygen species created during voltage application) (303).

Figure 10A:
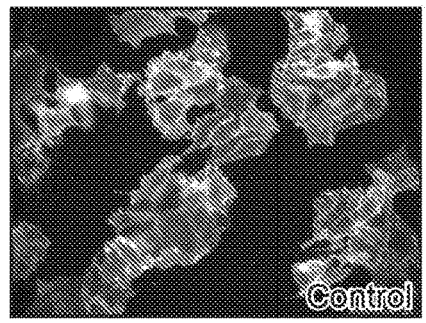
FIGS. 10A-10H show ultrafast de-labeling of cells with two separate detectable agents (PE-anti-EpCAM and PE-anti-Cytokeratine), according to an embodiment of the present disclosure.
Figure 10B:
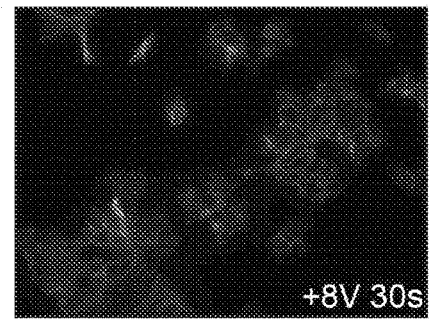
Figure 10C:
Figure 10D:
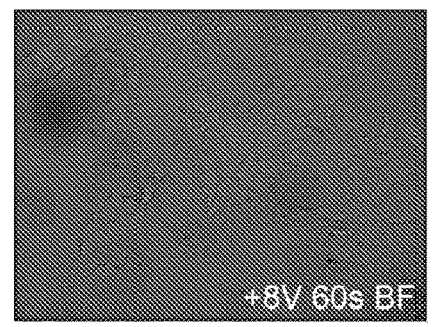
Figure 10E:
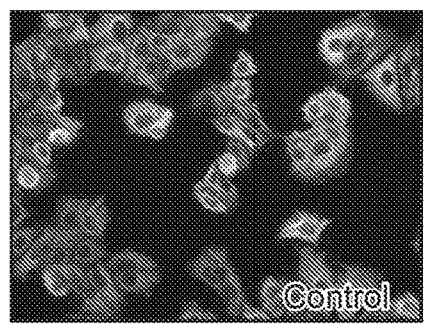
Figure 10F:
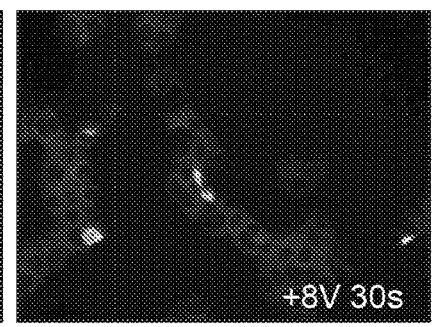
Figure 10G:
Figure 10H:
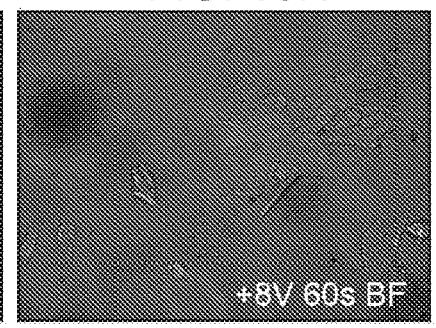

FIGS. 10A-10H shows the results of de-labeling of stained MCF-7 cells. The MCF-7 cells in FIGS. 10A-10H were stained with two different detectable agents (PE-anti-EpCAM and PE-anti-Cytokeratine) prior to undergoing de-labeling, as described in the methods of the disclosure. Labeled cells (FIG. 10A and FIG. 10E) can be rapidly de-labeled by applying a voltage of 8 volts to the solution in contact with the cells and/or detectable agent. After 30 seconds of non-photobleaching voltage application (FIG. 10B and FIG. 10F), the detectable agent signal (e.g., phycoerythrin signal) has been significantly reduced. After just 60 seconds of being subjected to an applied voltage, (FIG. 10C and FIG. 10G) the detectable agent signal has been drastically reduced. FIG. 10D and FIG. 10H are bright field images illustrating that the cells themselves have not been altered or lifted off from the substrate by the ultrafast de-labeling process.

Figure 11A:
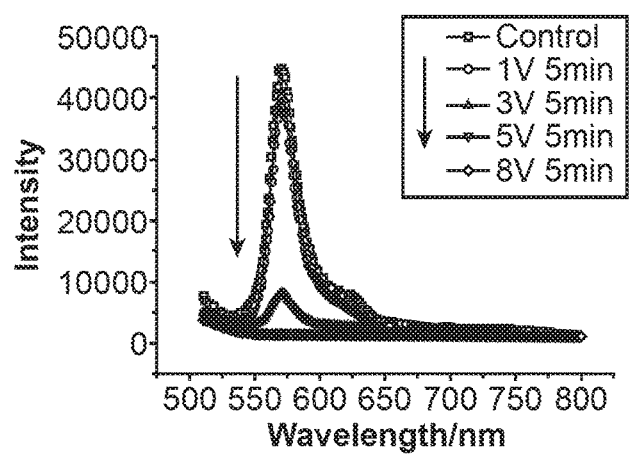
FIGS. 11A-11D show the effect of an applied voltage on de-labeling (FIGS. 11A-11B) and the speed at which de-labeling occurs at a given voltage (FIGS. 11C-11D) using ultrafast de-labeling methods. Intensity is expressed in arbitrary units of fluorescence (au) in FIG. 11A and FIG. 11C.
Figure 11B:
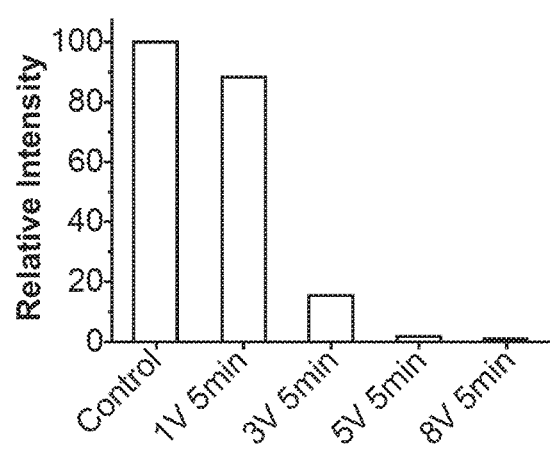
Figure 11C:
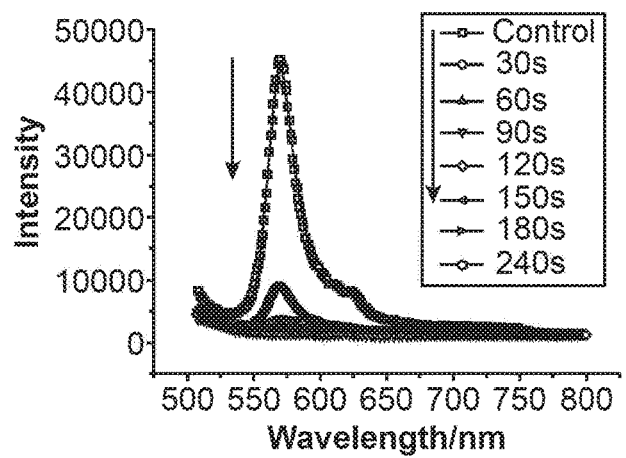
Figure 11D:
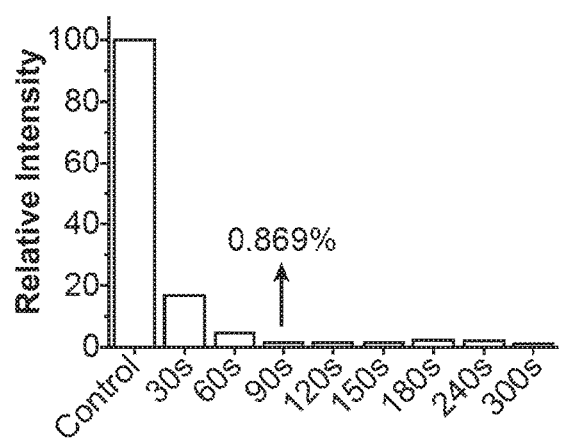
Figure 12A:
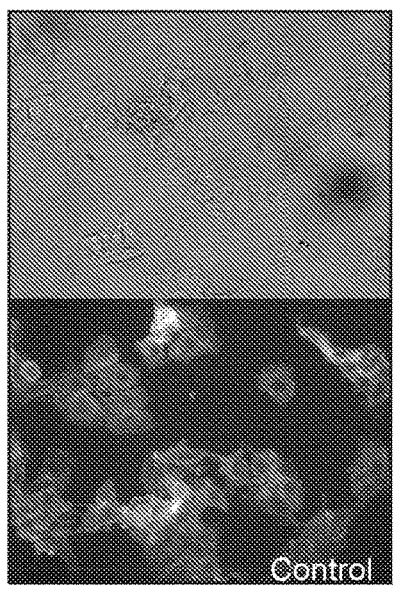
FIGS. 12A-12C show de-labeling of MCF-7 cells labeled with PFBT polymer dots after 3 minutes of 0 volts (FIG. 12A), 1 volt (FIG. 12B), and 5 volts (FIG. 12C).
Figure 12B:
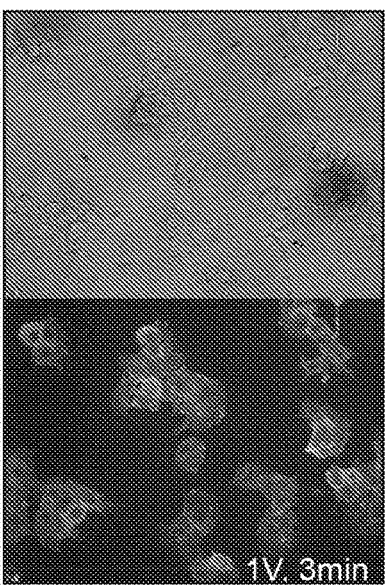
Figure 12C:
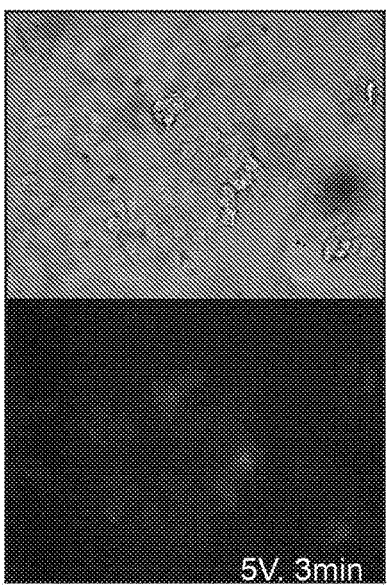

FIG. 11A-11D illustrates the surprising, nonlinear effect of voltage application on detectable agent signal (PE-anti-EpCAM) quenching or removal (FIG. 11A and FIG. 11B). Between 0 volts and 1 volt, the decrease in detectable agent signal after 5 minutes of treatment is less than 15%; however, when the applied voltage is increased to 3 volts for 5 minutes, detectable agent signal is decreased by over 80%. At a voltage of 8 volts, applied for 5 minutes, the detectable agent is no longer detectable. As seen in FIG. 11C and FIG. 11D, the quenching of detectable agent signal with a voltage of 8 volts occurs very rapidly. By 90 seconds of de-labeling, detectable agent signal has been reduced by over 99%.

De-labeling and de-staining can refer to the process of decreasing the signal produced by a detectable agent. De-labeling can involve destruction of the detectable agent, rendering the detectable agent unable to produce a signal without destroying and removing it (either temporarily or permanently), or disassociating a detectable agent from a molecule or cell so that the signal from the detectable agent is less able to be detected.

De-labeling can be performed in order to decrease the signal (or signals) from a detectable agent (or plurality of detectable agents). Likewise, labeling can be performed to create or enhance the amount of detectable signal, which can be associated with a cell or molecule of interest. De-labeling and labeling of a cell can be performed independently or in succession, increasing the efficiency of each process or the performance of each process or repeated cycles of de-labeling and labeling (e.g., destaining and staining) of a cell or plurality of molecules by taking advantage of fast de-labeling and labeling methods or the high labeling and de-labeling efficiencies provided by the described methods or both.

De-labeling a molecule can involve decreasing the signal of a detectable agent. In particular, de-labeling of a detectable agent can be accomplished with surprising efficiency (compared to techniques which are known in the art) when a voltage is applied to/across the detectable agent and/or the cell with which it is associated and/or to the solution in contact with a detectable agent (as described in 302 of FIG. 3; see also FIGS. 10A-10H, FIGS. 11A-11D, FIGS. 12A-12C, FIGS. 13A-13T, FIGS. 14A-14F, and FIGS. 15A-15C). A decrease in detectable agent signal of at least 90%, at least 95%, at least 96%, at least 97%, at least 98%, at least 99%, at least 99.5%, or at least 99.9% can be accomplished when a voltage of at least 1, 2, 3, 4, 5, 6, 7, 8, 9, 10, 15, 20, 25, 50, 75, or 100 volts is applied to the detectable agent and/or cell with which the detectable agent is associated and/or to the solution in contact with a detectable agent. Improved efficiency of de-labeling of a cell or molecule of interest, which can involve quenching (e.g., the process of de-labeling in which the signal from a detectable agent is decreased without removing the detectable agent from the molecule with which it is associated) or destruction of a detectable (e.g., rendering the detectable agent unable to produce a signal) agent, can be accomplished by applying a voltage of at least at least 1 volt, at least 2 volts, at least 3 volts, at least 4 volts, at least 5 volts, 6 volts, at least 7 volts, at least 8 volts, at least 9 volts, at least 10 volts, at least 15 volts, at least 25 volts, at least 50 volts, at least 75 volts, or at least 100 volts to a detectable agent or a cell or molecule associated with a detectable agent or to the solution in contact with a detectable agent. In some embodiments, voltage can be applied to the cell, molecule of interest, or solution in contact with the cell or molecule of interest for not more than 30 seconds, not more than 45 seconds, not more than 60 seconds, not more than 75 seconds, no more than 90 seconds, not more than 2 minutes, not more than 2.5 minutes, not more than 3 minutes, not more than 3.5 minutes, not more than 4 minutes, not more than 4.5 minutes, not more than 5 minutes, or not more than 10 minutes. De-labeling of a sample (e.g., a cell, molecule, or detectable agent) can be accomplished using the described methods to the degree described above in less than 20 minutes, 15 minutes, less than 10 minutes, less than 9 minutes, less than 8 minutes, less than 7 minutes, less than 6 minutes, less than 5 minutes, less than 4 minutes, less than 3 minutes, less than 2 minutes, less than 1.5 minutes, less than 1 minutes, less than 0.75 minutes or less than 0.5 minutes. Further improvements to de-labeling efficiency can be accomplished by heating the sample (e.g., a cell, molecule, or detectable agent) to above 26° C., 27° C., 28° C., 29° C., 30° C., 31° C., 32° C., 33° C., 34° C., 35° C., 36° C., 37° C., 38° C., 39° C., 40° C., 45° C., 50° C., 60° C., 70° C., or 80° C. and/or by introducing fluid flow across the sample (e.g., a cell, molecule, or detectable agent) and/or by physically agitating (e.g., shaking or rotating) the sample during de-labeling. Detection of a detectable agent can be performed before, after, or during de-labeling.

De-labeling of a molecule or cell can be performed in the presence of continuous, intermittent, timed, and controlled fluidic flow, or a combination thereof. For example, labeled cells were de-labeled in the presence of a continuous fluidic flow (as described in FIG. 14A-FIG. 14C), or in the presence of a controlled and timed application of fluidic flow (FIG. 14D-FIG. 14F).

When a sample (e.g., cell, molecule, or detectable agent) is de-labeled (e.g., quenched), the sample may contain some detectable agent capable of producing a detectable signal (e.g., a detectable agent signal). This can be described as residual detectable agent signal, and, in the case of a fluorescent detectable agent, it can be described as residual fluorescence. Residual detectable agent signal (e.g., residual fluorescence) can be determined, for example, relative to the detectable agent signal prior to de-labeling or prior to labeling, relative to a second similarly labeled sample that has not been de-labeled, relative to the background signal from the cell or molecule prior to labeling (e.g., autofluorescence), relative to the residual detectable signal or residual fluorescence after the previous round of de-labeling, relative to a saturation level of detectable signal (e.g., fluorescence after labeling with a detectable agent at 20 degrees Celsius for 1 hour), or as a percentage of sites of a cell (e.g., the percentage of sites with which a given detectable agent can specifically associate). Residual fluorescence, like measurement of detectable agent fluorescence prior to de-labeling, can be determined with respect to the intensity of detectable agent signal (e.g., the number of photons per second and/or relative energy of photons emitted by the detectable agent). Residual fluorescence following ultrafast de-labeling can be less than 5%, less than 2%, less than 1%, less than 0.5%, or less than 0.1%. To verify the residual fluorescence has reached a desired level, a portion of the de-labeled cells can be detected or imaged, either after de-labeling for verification or during de-labeling so the de-labeling process can be terminated after the desired residual fluorescence signal has been reached.

This result can be obtained through a number of non-exclusive mechanisms, each of which can be used in the methods and systems of this disclosure, including application of a voltage or electric field to the cell or detectable agent or to the solution in contact with the cell or detectable agent, the use of a chemical signal quencher (e.g., Black Hole Quencher®, such as available from Sigma-Aldrich, e.g., BHQ-1, BHQ-2, or BHQ-3), photobleaching, cleavage of a linker connecting a detectable agent to an affinity tag or molecule of interest (e.g., chemical cleavage of disulfide linkage, hydrolysis of a linker, glucose cleavage of a linker, cleavage of a linker with light, thermally-induced cleavage of a DNA linker, DNA/PNA (peptide nucleic acid) strand exchange (e.g., with respect to linker dissolution), pH-induced structural change to alter DNA linker, enzyme-based DNA linker cleavage, DNA aptamer-based cleavage system (in the presence of adenosine triphosphate), etc.), chemical reaction or chemical reduction or chemical oxidation of a detectable agent, photo switching or photo-quenching of detectable agents (e.g., photo-switching or quenching of polymer dots with light), cross-linking of a Forster resonance energy transfer (FRET) detectable agent to a quencher, electrochemical oxidation of a detectable agent, or stripping an antibody affinity tag with a stripping buffer. These mechanisms can be complementary to each other and thus combined to further increase the performance and efficiency of de-labeling.

De-labeling can be performed in the presence of fluidic flow, which can enhance the speed and/or efficiency of de-labeling and/or the extent of de-labeling over a given period of time. For example, in the case of chemical reaction-based de-labeling, or the electrochemical oxidation of the detectable agent upon application of a voltage to the solution in contact with the detectable agent, fluid flow will enhance the transport of reactive chemical species or oxygen species to the detectable agent, thus improving the speed and/or efficiency of de-labeling or the extent of de-labeling. Fluid flow can be introduced, for example, by flowing fluid in a flow channel or flow cell over the cells or molecules of interest or with respect to the detectable agent or cell. Fluid flow can be any fluid movement with respect to the detectable agent or cell or molecule of interest, and can be introduced, for example, by fluid agitation or shaking.

Generation of Voltages for De-Labeling

Figure 2:
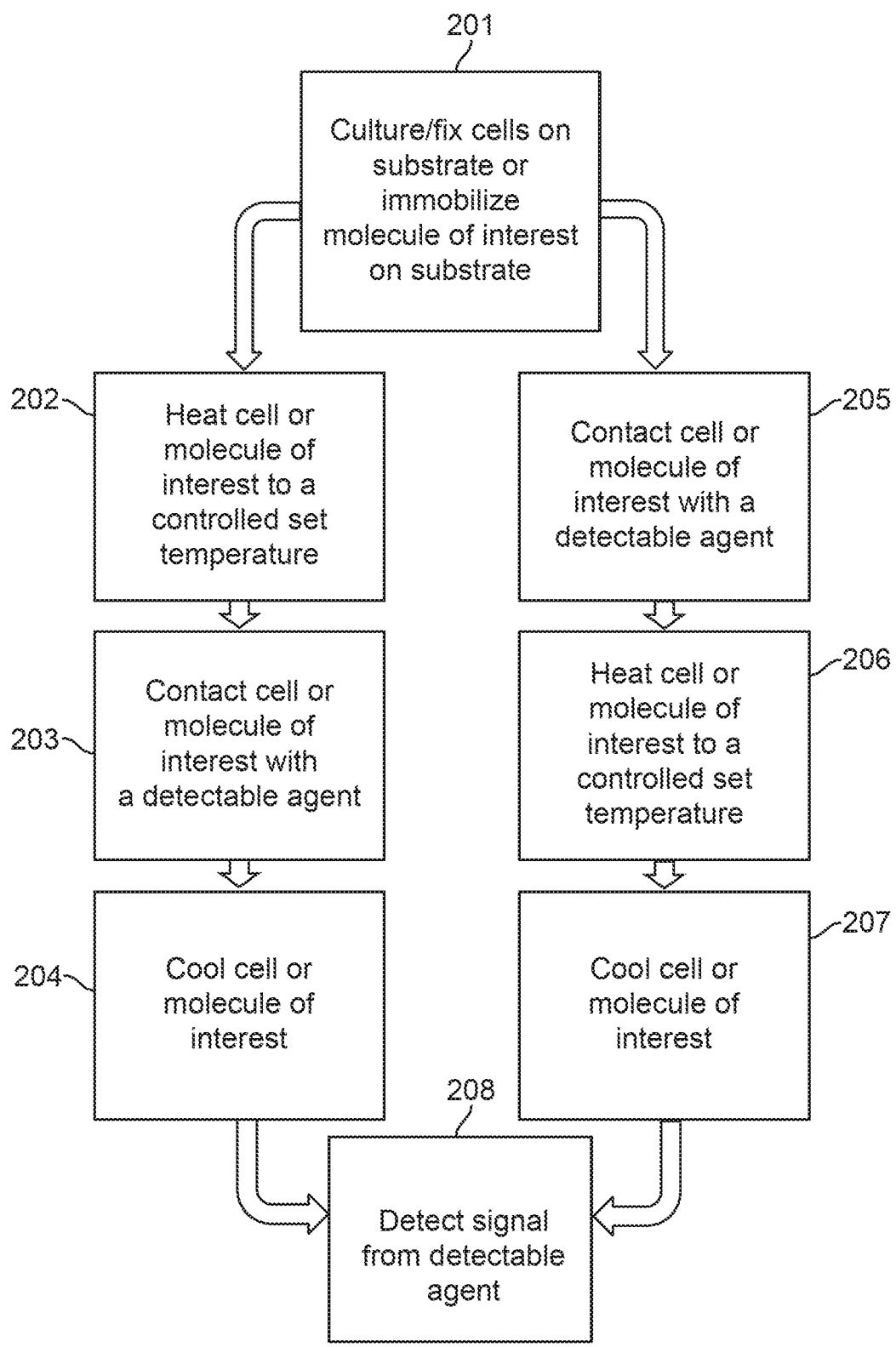
FIG. 2 shows a flow diagram of ultrafast labeling of cells or molecules of interest with a detectable agent, wherein a step for cooling the sample (e.g., the cell or molecule of interest) is performed after labeling and before detection.

A voltage, current, or electric field can be generated to aid in de-labeling of a molecule or cell (as described in step 202 of FIG. 2). The generation of a voltage, current, or electric field can be described using Maxwell's equations, and the voltage, electric field strength, directionality of current, or other parameters experienced by a sample (e.g., a cell, molecule, or detectable agent) can be prescribed using these relationships for the design of ultrafast de-labeling protocols and/or systems for use in ultrafast de-labeling procedures. A voltage can be specifically applied between electrodes (e.g., at least 2, 3, 4, 5, 6, 7, or 8 electrodes) so that the sample is exposed to a desired voltage or time-dependent voltage pattern. A voltage can also be applied to one electrode (e.g., to generate reactive chemical or reactive oxygen species) so that the sample is exposed to a desired voltage or time-dependent voltage pattern to achieve the most efficient de-labeling conditions. The voltage or electric field applied to the cell or molecule of interest can be direct current (DC), alternating current (AC), or a combination AC and DC. That is, the polarity or directionality of the voltage or electric field can change during application. The magnitude and/or polarity and/or directionality of the applied voltage or electric field can include sinusoidal patterns, sawtooth patterns, ramping patterns, step function patterns, square wave patterns, embodiments of those patterns that comprise a change in polarity or directionality of the voltage or field, or any combination thereof. The voltage or electric field can be constant or it can be pulsed or intermittently applied during de-labeling.

The voltage or electric field can be generated by a single electrode or a plurality of electrodes attached to a power supply. The voltage can be generated by a single electrode, between two electrodes or between a plurality of electrodes attached to a power supply. The number and arrangement of electrodes with which the voltage or current or electric field is produced can affect both the shape of the voltage pattern or electric field and the voltage or current or electric field experienced by the cell, molecule, or detectable agent (e.g., with respect to voltage or electric field strength and/or polarity and/or directionality and in accordance with Maxwell's equations).

An electrode can comprise a conductor or a semiconductor and can be comprised of a metal, a non-metal, an alloy, or a combination thereof. In some cases, an electrode can be integrated into the substrate in which the cell is located, while in other cases an electrode can be integrated into a microscope or fluidic apparatus. Alternatively, an electrode can be free-standing. In some embodiments, the electrode can be a platinum electrode, a gold electrode, a rhodium electrode, a copper electrode, a zinc electrode, a lead electrode, a silver electrode, a titanium electrode, a brass electrode, a palladium electrode, a graphite and carbon electrode, or a mixed metal oxide electrode.

When an electrode is integrated into an apparatus or substrate (e.g., a chip or cell array), the positioning of the electrode can be designed such that the appropriate voltage, current, or electric field geometry, directionality, and strength are experienced by the cell, molecule, or detectable agent. Furthermore, integration of an electrode into a substrate or apparatus decreases the amount of variability between experiments and reduces the time and calculations needed to calibrate a voltage or electric field generation system prior to experimentation. Integration of an electrode into a substrate or apparatus can decrease the amount of time for the reactive chemical species, such as reactive oxygen species, generated at the electrode to reach the cell, or molecule of interest, or detectable agent for de-labeling.

Even when an electrode is integrated into a substrate or an apparatus, mechanisms for correcting electrode positioning can be incorporated into the substrate or apparatus. For example, an electrode can be attached to a movable arm or platform, which can comprise a gear (e.g., a gear for moving a sample platform or tray) and can connect the electrode to the substrate or the apparatus or to the solution in contact with a detectable agent. Such a movable arm or platform can be adjusted manually or via a fine-tuning mechanism (e.g., a rack-and-pinion gear mechanism). In some embodiments, an electrode can be detached from the substrate or apparatus to which it is connected. The voltage or electric field source (e.g., the electrode) can be situated at least 1 mm from the sample, at least 5 mm from the sample, at least 1 cm from the sample, at least 2 cm from the sample, at least 3 cm from the sample, at least 4 cm from the sample, or at least 5 cm from the sample. At a distance of at least 1 cm from the sample, a voltage of at least 0.5 V, at least 1 V, at least 2 V, at least 3 V, at least 4 V, at least 5 V, at least 6 V, at least 7 V, at least 8 V, at least 9 V, at least 10 V, at least 15 V, at least 20 V, at least 25 V, at least 50 V, or at least 100 V can be applied to the cell or to the solution in contact with the cell for de-labeling. At a distance of at least 1 mm from the sample, a voltage of at least 0.5 V, at least 1 V, at least 2 V, at least 3 V, at least 4 V, at least 5 V, at least 6 V, at least 7 V, at least 8 V, at least 9 V, at least 10 V, at least 15 V, at least 20 V, at least 25 V, at least 50 V, or at least 100 V can be applied to the cell or to the solution in contact with the cell for de-labeling. The electrode through which a voltage is applied can be immersed in the solution in contact with the cell/detectable agent and the electrode is situated at least 1 mm from the farthest cell or detectable agent, at least 5 mm from the farthest cell or detectable agent, at least 1 cm from the farthest cell or detectable agent, at least 2 cm from the farthest cell or detectable agent, at least 3 cm from the farthest cell or detectable agent, at least 4 cm from the farthest cell or detectable agent, at least 5 cm from the farthest cell or detectable agent, at least 10 cm from the farthest cell or detectable agent, at least 20 cm from the farthest cell or detectable agent at least 30 cm from the farthest cell or detectable agent. At a distance of at least 1 cm from the farthest cell or detectable agent, a voltage of at least 0.5 V, at least 1 V, at least 2 V, at least 3 V, at least 4 V, at least 5 V, at least 6 V, at least 7 V, at least 8 V, at least 9 V, at least 10 V, at least 15 V, at least 20 V, at least 25 V, at least 50 V, or at least 100 V can be applied to the detectable agent or to the solution in contact with the detectable agent for de-labeling. At a distance of at least 1 mm from the farthest cell or detectable agent a voltage of at least 0.5 V, at least 1 V, at least 2 V, at least 3 V, at least 4 V, at least 5 V, at least 6 V, at least 7 V, at least 8 V, at least 9 V, at least 10 V, at least 15 V, at least 20 V, at least 25 V, at least 50 V, or at least 100 V can be applied to the detectable agent or to the solution in contact with the detectable agent for de-labeling.

When an electrode is free-standing, more flexibility can be afforded to the positioning of the electrode relative to the sample (e.g., the cell, molecule, or detectable agent). In embodiments where the geometry or size of the substrate, fluidic system, or detection system do not allow for the electrode to be left in position throughout the experiment, free-standing electrodes can be useful as they can easily be removed or repositioned when not in use or when the modality of usage changes.

When the means for generating a voltage or electric field comprises a single electrode, the electrode can be used as a source of negative charge and a separate ground can be employed, such as a conductor located in the local environment (e.g., the frame of the imaging apparatus or support structures, wiring located near the electrode, or fluids local to the electrode, such as buffers used in the fluidics system). The electrode can also be used as a source of positive charge. The electrode can also be used as a source of reactive chemical species, such as reactive oxygen species, through the occurrence of electrochemical reactions at the electrodes. In some embodiments, the substrate, a fluid, a metallic object such as a computer frame or instrument housing can be used as an electrode or a ground.

The electric field can also be induced by a magnet or magnetic element. A magnet used to create an electric field can be a permanent magnet or an electromagnet.

The electric field itself can be of any shape or orientation and can be created (e.g., through the positioning of electrodes relative to the sample or the magnitude of the electric field) such that it passes through the sample (e.g., a cell, molecule, or detectable agent). In some embodiments, the directionality of an electric field can be adjusted or reversed during de-labeling by adjusting electrode positioning or altering the magnitude or direction of electrical current supplied to the electrode or magnet.

Cyclic De-Labeling and Labeling

A labeled cell can be labeled and de-labeled or de-labeled and labeled in sequence or cycles for at least 2 times, at least 3 times, at least 4 times, at least 5 times, at least 10 times, or at least 50 times. For example, at least nine cycles of labeling and de-labeling can be conducted without noticeable epitope damage on the cells as described in FIGS. 15A-15C. Cyclic labeling and de-labeling can be accomplished by performing the methods of de-labeling (e.g., as described above) and labeling (e.g., as described above) in sequence, and the combined process of de-labeling and labeling a cell or molecule can be performed cyclically (e.g., repeatedly, in multiple rounds) in order to assay a larger number of molecules or to utilize a greater combination of detectable agents. In some embodiments, a wash step can be performed between the steps of de-labeling and labeling; however, a wash step is not necessary, and in some embodiments, greater efficiency can be accomplished without the inclusion of a wash step between de-labeling and labeling steps. In other embodiments, a wash step may be desired to wash away extraneous molecules around the cell prior to labeling. In yet another embodiment, the labeling step, which introduces the new detectable agent simultaneously can serve as a wash step In this way, a cell or molecule of interest can be de-labeled and labeled in less than 15 minutes, less than 14 minutes, less than 13 minutes, less than 12 minutes, less than 11 minutes, less than 10 minutes, less than 9 minutes, less than 8 minutes, less than 7 minutes, less than 6 minutes, less than 5 minutes, less than 4 minutes, less than 3 minutes, less than 2 minutes, or less than 1 minute.

Figure 16:
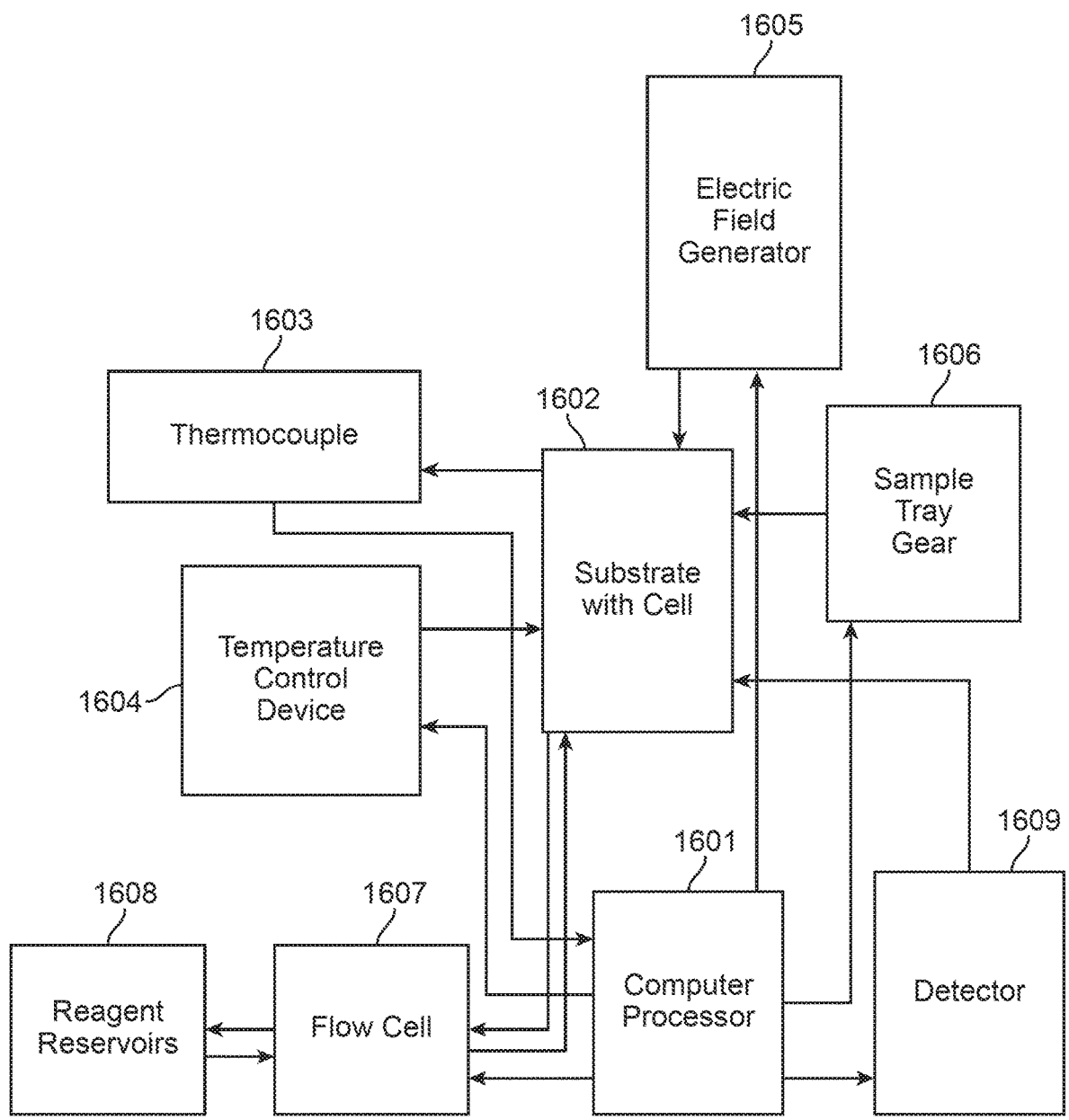
FIG. 16 shows a system for ultrafast cyclic fluorescent imaging.
Figure 18A:
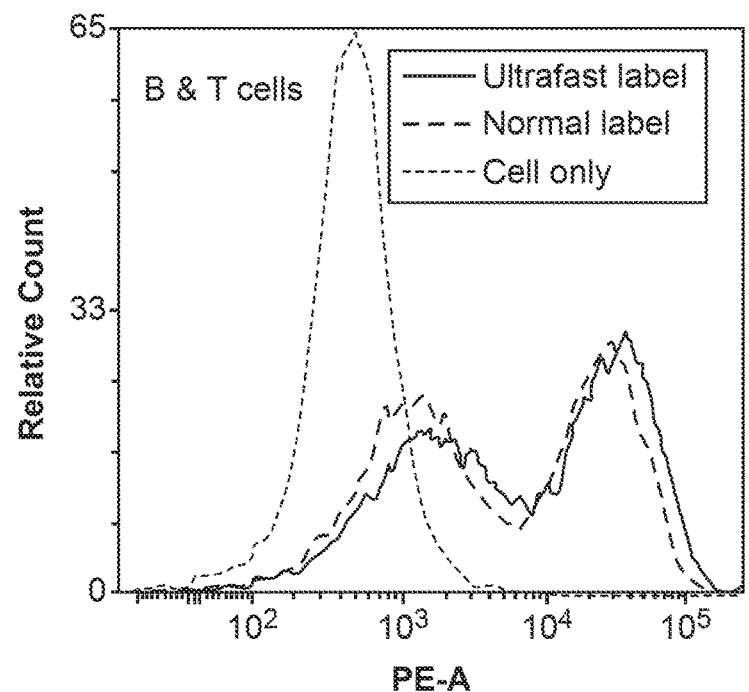
FIGS. 18A-18B show flow cytometry results following B-cell and T-cell labeling using ultrafast labeling methods, showing comparable non-specific binding and specific labeling between normal and ultrafast labeling methods.
Figure 18B:
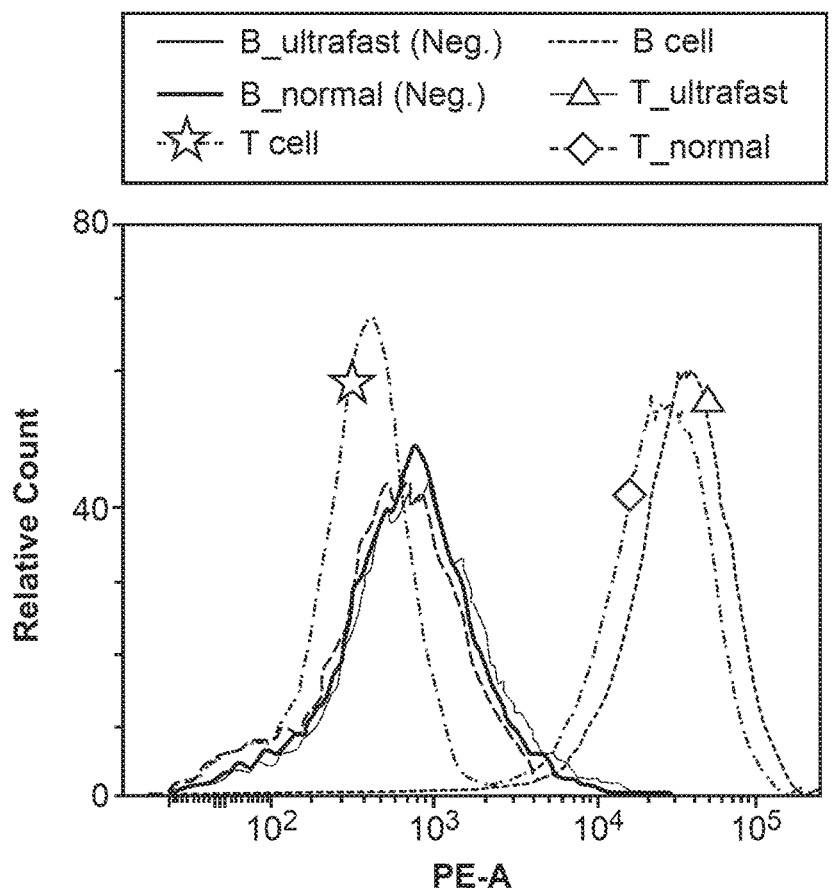

FIG. 16 shows a system for ultrafast cyclic fluorescent imaging. Computer processor 1601 can initiate staining, with user input, by signaling the sample tray 1606 to open. After the user inserts the substrate with a cell on it 1602, the user signals tray gear closes the tray by inputting a command into the computer processor or by pushing the tray closed. The computer processor 1601 executes a program to command the flow cell 1607 to deliver fixatives and permeabilizing agents from the reagent reservoir 1608 to the cell on the substrate 1602 before commanding the flow cell 1607 to remove those reagents from the substrate and cell 1602. Alternatively, the user can insert the substrate without any cells into the sample tray 1606, after which the user signals the tray gear to close the tray by inputting a command into the computer processor (e.g., via a keyboard, mouse, touchscreen, or other user interface) or by pushing the tray closed. The computer processor 1601 executes a program to command the flow cell 1607 to deliver cells from a cell reservoir or container to the substrate and for the cells to be associated or immobilized (e.g., to adhere) on the substrate before fixatives and/or permeabilizing agents and/or washing fluid from a reagent reservoir 1608 is delivered to the cell, which has associated with or been immobilized relative to the substrate 1602 before commanding the flow cell to remove those reagents from the substrate and cell 1602. In yet another embodiment, the user can insert a substrate that has no associated cells into the sample tray 1606, after which the user signals the tray gear to close the tray by inputting a command into the computers processor or by pushing the tray closed. The computer processor 1601 executes a program to command the flow cell 1607 to deliver cells that have previously been fixed and/or permeabilized from a cell reservoir or container to the substrate and for the cells to be associated or immobilized on the substrate. The computer processor 1601 then executes a program from its onboard storage, heating the substrate and cell 1602 by initializing the temperature control device 1604. Through the feedback provided by the thermocouple 1603, the computer processor controls the temperature of the substrate and cell within an acceptable tolerance range. Then the computer processor 1601 initializes the flow cell 1607 to deliver a first set of detectable agents from the reagent reservoir subsystem 1608 through the channels of the flow cell 1607 to the cell on the substrate 1602. Alternatively, the computer processor 1601 can execute a program to heat the substrate and cell 1602 after the flow cell 1607 has completed delivery of a first set of detectable agents to the cell on the substrate 1602. The cell is allowed to undergo labeling for less than 10 minutes (as described, for example, in FIG. 1 and FIG. 2 and illustrated in FIGS. 9A-9G) before the computer processor 1601 commands the flow cell 1607 to remove the detectable reagent from the cell and substrate. The computer processor 1609 commands the detector 1607 to image the cell. Optionally, the computer processor 1609 commands the cooling of the cell and substrate to a lower temperature or to room temperature prior to imaging. The computer processor 1601 then commands the voltage generator 1605 to generate a voltage of no less than 5 volts for no longer than 6 minutes, de-labeling the cell (as described above and in FIG. 3 and as illustrated in FIGS. 10A-10H, FIGS. 12A-12C, FIGS. 18A-18B, and FIGS. 19A-19D. Optionally, the computer processor 1601 can command temperature control device 1604 to reach a set temperature prior to or during voltage application. The computer processor 1601 then commands the flow cell 1607 to deliver a second set of detectable agents to the cell, labeling the cell with the second set of markers. Optionally, the computer processor 1601 can command the detector 1607 to image the cell to verify sufficient de-labeling either during or after voltage application. As before, the computer processor 1601 commands the detector 1609 to image the cell once ultrafast labeling is complete before instructing the voltage generator 1605 to apply a voltage and de-label the cell a second time.

Detectable agents and/or cellular structures can be detected (e.g., by optical fluorescent microscopy) at any point during any round of cyclic de-labeling and labeling. That is, a detectable agent can be detected prior to, after, or during any round of labeling or de-labeling. In some embodiments, the samples can be subjected to a detection step (e.g., stimulating the detectable agent with a laser and detecting the photons emitted by the detectable agent) after each labeling step and before each de-labeling step. In some embodiments, a separate detection step can be performed after a de-labeling step and before the following labeling step in order to, for example, verify that the signals from the detectable agent(s) have been diminished or to determine a baseline from which subsequent detection events can be normalized. For this purpose, it can be sufficient to carry out detection on a subset of the sample (e.g., a portion of the cells or molecules of interest).

In some embodiments, different conditions (e.g., temperature or concentration of detectable agent) may be required to label cells or molecules with certain detectable agents, for example, in labeling cells with fluorescent antibodies and with fluorescent nucleic acids. In these cases, multiple rounds of labeling, each of which comprising experimental conditions (e.g., temperature, time in contact with detectable agents, concentration of detectable agent during contact with sample, etc.) suitable for the detectable agents being used in that round of labeling, can be performed per round of de-labeling and/or detecting. Similarly, optimal de-labeling of individual detectable agents may require different experimental conditions for each individual combination of detectable agents (e.g., the use of Black Hole Quencher in addition to the application of a voltage); therefore, multiple rounds of de-labeling can be performed for each round of labeling and/or detecting.

In some embodiments, samples can be labeled with more detectable agents than the detector or detection system can detect without being reconfigured. Therefore, a labeling step can comprise the reconfiguring of the detector or detection system. Reconfiguration of a detector or detection system can also occur between labeling sequential steps, between sequential de-labeling steps, or between labeling and de-labeling steps. For example, the filter cube on a microscope may be changed so that each detectable agent on a cell can be detected. As another example, the excitation source (e.g., LEDs or lasers with different output light, such as wavelength or intensity) or the camera (e.g., with different sensitivity to different wavelengths of light or with different pixel size and pixel sensitivity or quantum efficiency) may be changed so that each detectable agent on a cell can be detected. In situations such as these, multiple rounds of detection can be performed for each round of labeling and/or de-labeling, as part of the methods described herein. The same detection channels can then be reused by de-labeling and re-labeling the cell.

As detection of a detectable agent can occur before, during, or after either labeling or de-labeling of a cell or molecule and labeling and/or de-labeling of a cell can be performed cyclically, detection of a detectable agent can occur multiple times for a given cell or molecule over the course of an experiment, via a detectable agent.

Figure 4:
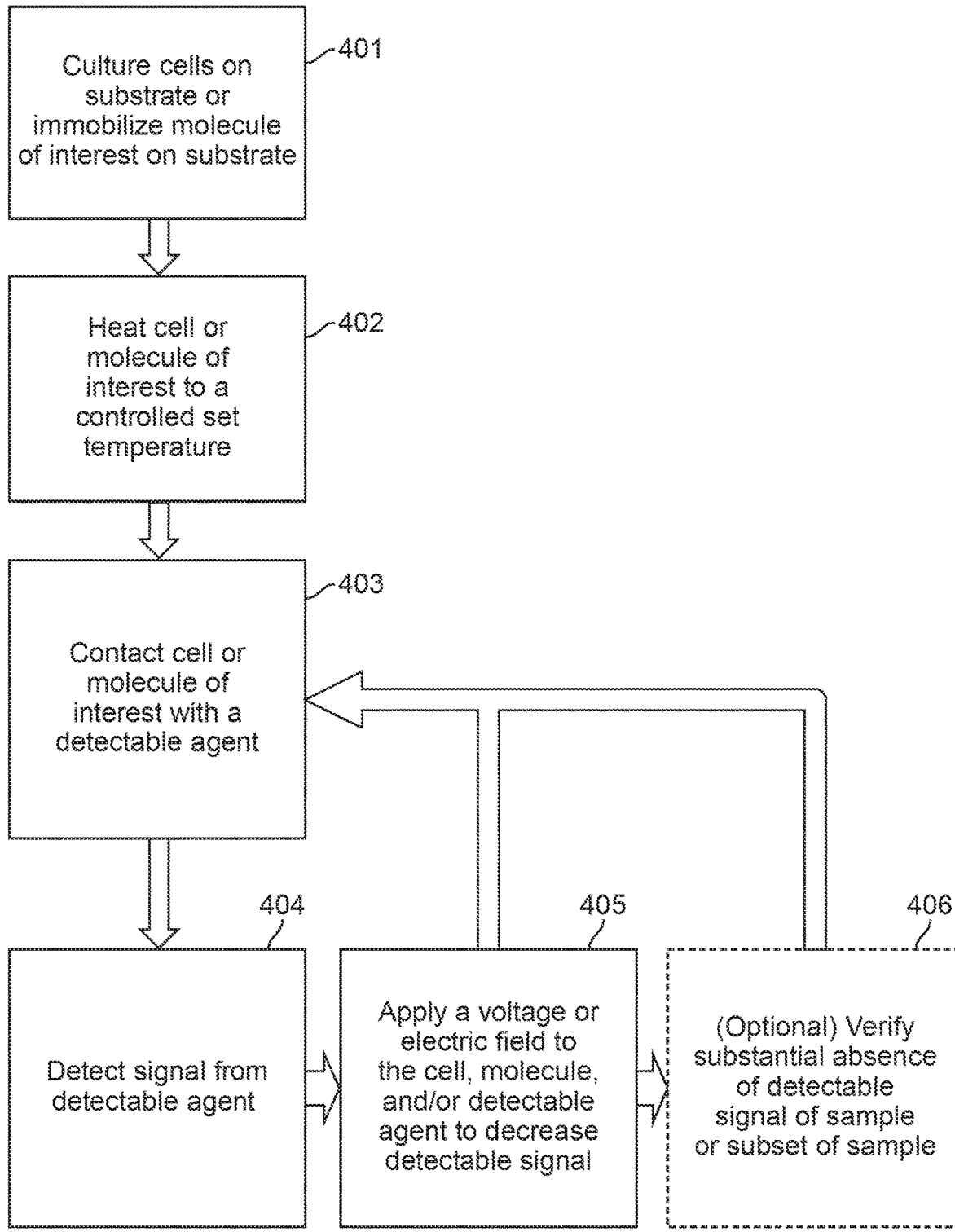
FIG. 4 shows a flow diagram of ultrafast cyclic fluorescent imaging involving ultrafast labeling and ultrafast de-labeling of cells or molecules of interest.
Figure 5:
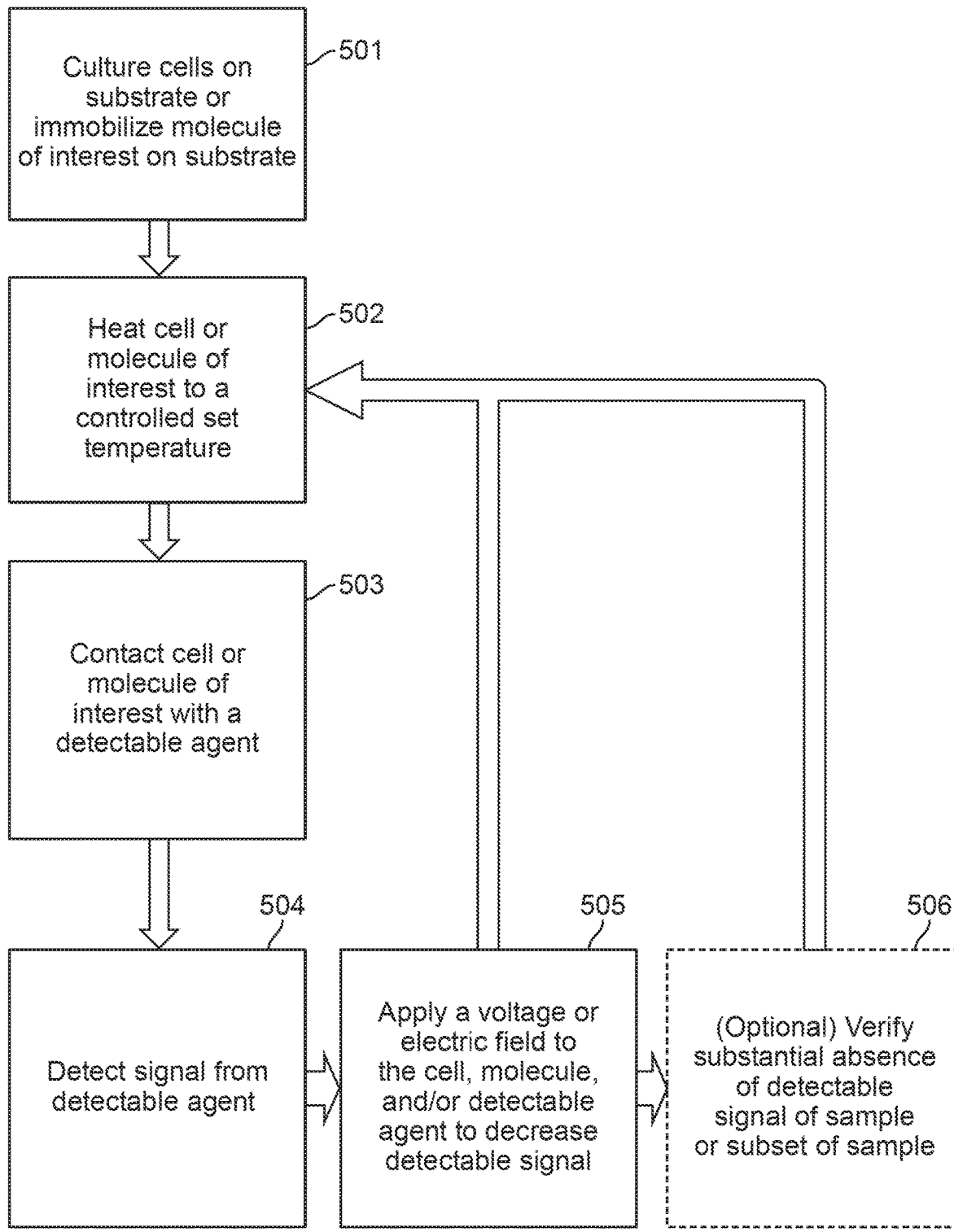
FIG. 5 shows a flow diagram of ultrafast cyclic fluorescent imaging involving ultrafast labeling and ultrafast de-labeling of cells or molecules of interest, wherein the step of heating the sample (e.g., the cell or molecule of interest) can be repeated in each cycle.
Figure 6:
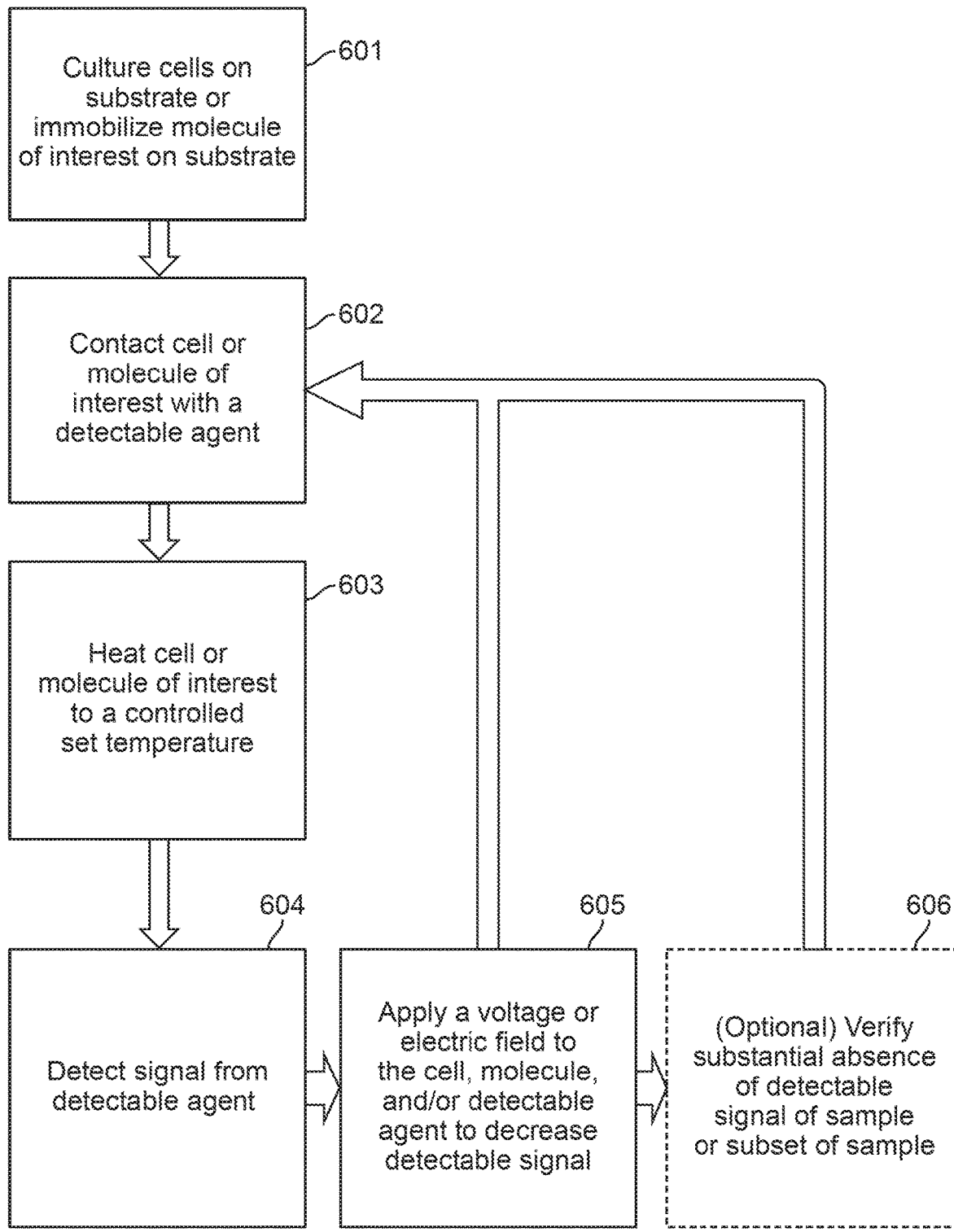
FIG. 6 shows a flow diagram of ultrafast cyclic fluorescent imaging involving ultrafast labeling and ultrafast de-labeling of cells or molecules of interest, wherein the step of heating the sample (e.g., the cell or molecule of interest) can be repeated in each cycle.
Figure 7:
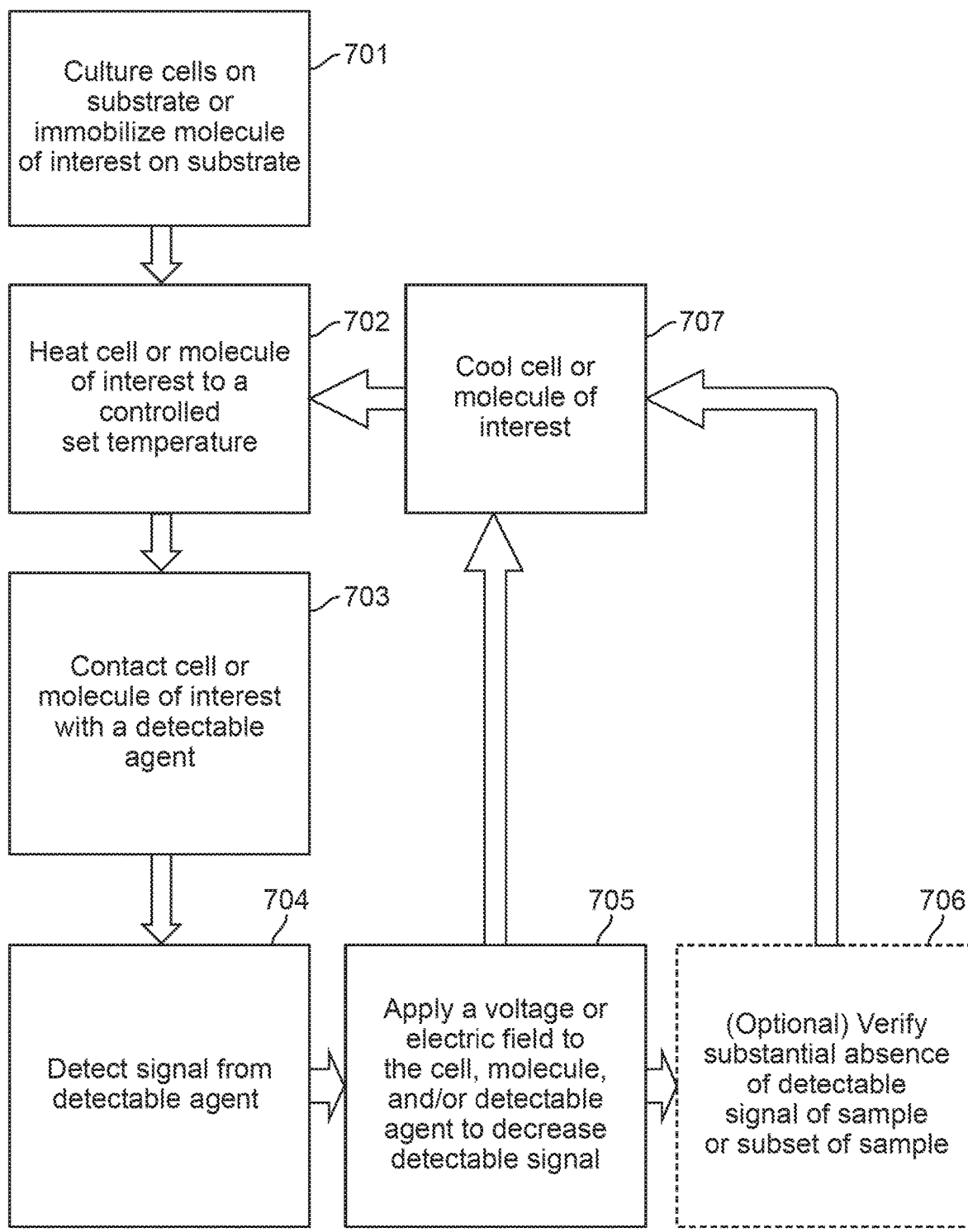
FIG. 7 shows a flow diagram of ultrafast cyclic fluorescent imaging involving ultrafast labeling and ultrafast de-labeling of cells or molecules of interest, wherein the step of heating the sample (e.g., the cell or molecule of interest) and a step for cooling the sample can be repeated in each cycle.
Figure 8:
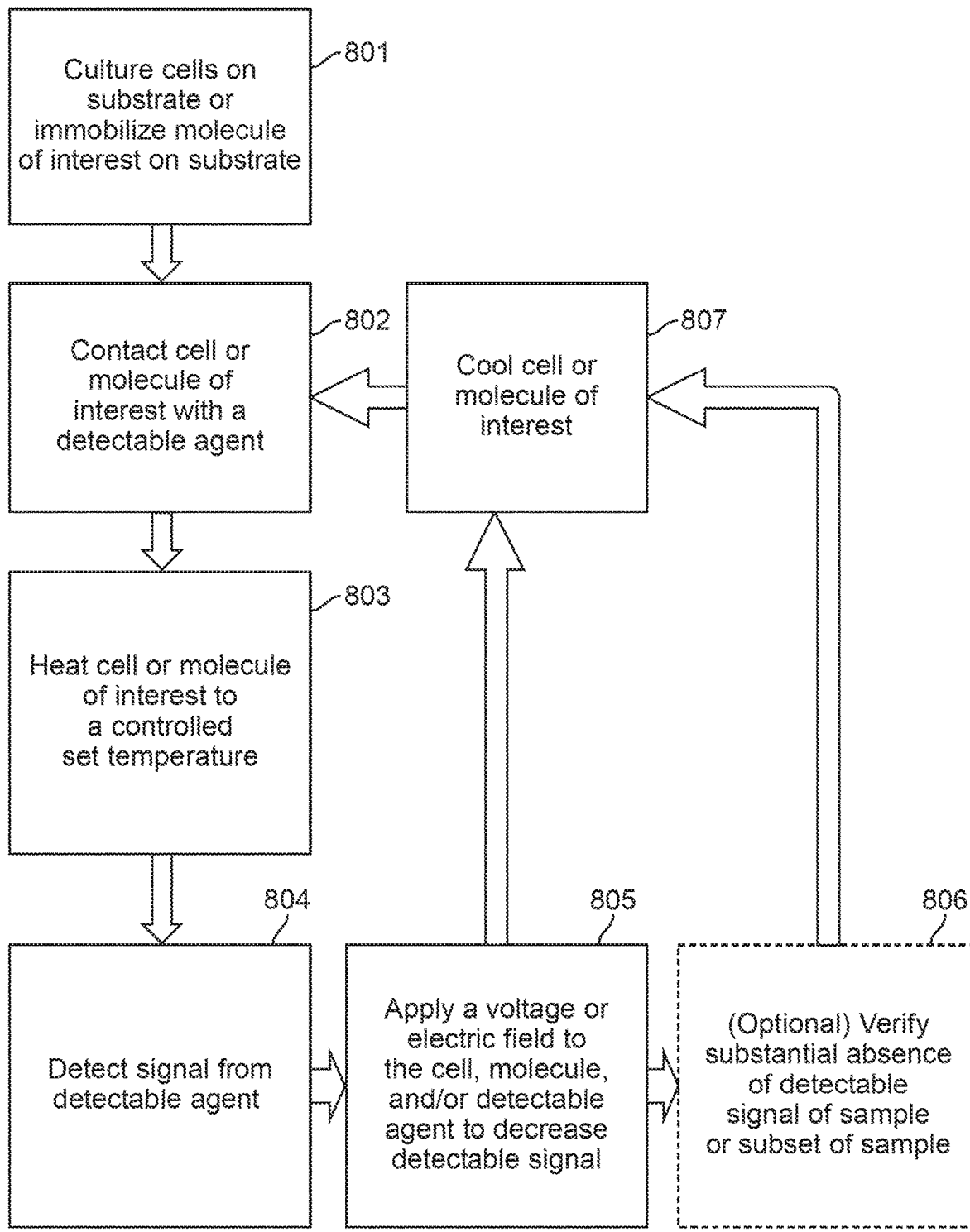
FIG. 8 shows a flow diagram of ultrafast cyclic fluorescent imaging involving ultrafast labeling and ultrafast de-labeling of cells or molecules of interest, wherein the step of heating the sample (e.g., the cell or molecule of interest) and a step for cooling the sample can be repeated in each cycle.

In addition to the methods described in FIG. 4-FIG. 6, ultrafast cyclic fluorescence imaging can comprise a step for cooling the sample (e.g., the cell or molecule of interest, 707, 807), which can comprise, for example, the allowing the sample to radiate heat passively, exposure to or convective flow of fluids (e.g., liquids in contact with the sample and/or substrate, gases such as air or vapor phase of liquid nitrogen in contact with the sample and/or substrate or in contact with the fluids that are in contact with the sample), or refrigeration of the sample and/or its environment (e.g., the substrate and/or the gas phase in contact with the sample or substrate). In some embodiments, cooling the sample can comprise defining a set point temperature (e.g., 20° C., 25° C., 30° C.) and controlling the temperature within 0.25° C., within 0.5° C., within 1° C., within 2° C., within 3° C., within 4° C., and within 5° C. of the set point temperature. In some embodiments, the temperature control device can comprise a means of cooling the sample or reagents (e.g., fluids in a reagent reservoir which will be placed in contact with the sample as a means of cooling the sample).

A cooling step in cyclic ultrafast fluorescence labeling and de-labeling (as described in some embodiments in FIG. 7 and FIG. 8) or ultrafast fluorescence labeling (as described in FIG. 2) can occur immediately prior to heating the sample (e.g., the cell, molecule of interest, or detectable agent, 702, 803), immediately prior to contacting the sample with a detectable agent (103, 104, 203, 205, 403, 503, 603, 703, 802), immediately prior to detecting the signal from the detectable agent (e.g., between 103 and 106, between 203 and 208, between 403 and 404, between 503 and 504, between 603 and 604, between 703 and 704, or between 803 and 804), or immediately prior to applying a voltage or electric field to the sample (e.g., between 301 and 302, between 504 and 505, between 604 and 605, between 704 and 705, or between 804 and 805). A cooling step, which can comprise cooling the cell, molecule, or detectable agent, can also occur immediately prior to optionally verifying substantial absence of (e.g., substantial decrease in) detectable signal (e.g., between 302 and 303, between 405 and 406, between 505 and 506, between 605 and 606, between 705 and 706, or between 805 and 806).

Labeling and/or de-labeling of a sample, either as independent methods or as part of ultrafast cyclic fluorescence imaging, can comprise applying mechanical forces to the sample. Applying mechanical forces to a sample can, in some embodiments, comprise flowing a fluid over the sample or agitating the cells and/or the substrate or fluids in contact with the sample. Such application of mechanical force can occur at any point in ultrafast labeling, de-labeling, or cyclic fluorescence imaging and can be performed for the purpose of improving contact of the detectable agent with the sample or improving wash/removal of detectable agents or improving de-labeling. Fluid flow over the sample can also be useful in improving mass transfer (e.g., mass transport) during labeling (e.g., by improving transport of detectable agents to the cells or molecules of interest) or de-labeling (e.g., by improving transport of reactive chemical species, such as reactive oxygen species, from the electrode region to the cells/detectable agents). Therefore, a step involving fluid flow can be incorporated at any point in ultrafast labeling, de-labeling, imaging, or cyclic fluorescent imaging methods, as described herein. Fluid flow steps can involve the use of a flow cell.

Multiplexing and Automation

The process of cyclic de-labeling, labeling, and detection of molecules can be automated and/or multiplexed to further improve the efficiency of the process. In such a multiplexed method, a plurality of substrates, each of which containing a cell or molecule of interest, can be processed (e.g., labeled, de-labeled, washed, stimulated, detected, etc.) in rapid succession. To facilitate multiplexing, substrates can be stacked and moved into position for individual steps of the labeling and/or de-labeling process (e.g., heating, labeling, detecting, application of voltage or electrical field, etc.) through a moveable sample tray capable of moving substrates individually into position for each step. This movement of substrates into position for each step can comprise a gear that operates the sample tray, and the gear can be operated by the computer processor as part of a pre-established program, which, in turn can be customized for individual protocols or detectable agents to be used in experimentation. In some embodiments, multiple steps, such as labeling and detection, or detection and de-labeling, can occur in the same location, without requiring the substrate to be moved between steps.

The processes of activating and deactivating flow cell(s), voltage or electric field generator(s), temperature control device(s), moving microscope stage(s) and filter cube(s), and detector(s) can be automated such that a cell (or molecule of interest) is labeled, de-labeled, and a detectable agent (or plurality of detectable agents) is detected without additional intervention from a user. As these processes can be performed cyclically according to the methods mentioned above, multiple sets of detectable agents can be used to label a cell and can be detected in a surprisingly short period of time by employing the methods and systems described herein. Therefore, in some embodiments, the system can comprise an open or enclosed system in which the user initiates a program (e.g., a pre-programmed or user-defined program that performs the method of labeling, de-labeling, or labeling and de-labeling a sample) and all other steps of the program are performed automatically by the system. In some embodiments, user intervention is only required at the beginning (e.g., inserting the substrate and/or cells and/or detectable reagents, initiating the program or computer processor) and at the end (e.g., obtaining the results from the computer processor and removing the reagents/disposables from the system) of the experiment.

Improvements to the efficiency of labeling, de-labeling, and imaging of cells conferred by multiplexing and automation of the methods described herein can improve throughput of cell staining and de-staining and detection protocols to an average of at least 10 wells per minute, at least 20 wells per minute, at least 30 wells per minute, at least 40 wells per hour, at least 50 wells per hour, at least 100 wells per hour, at least 10 cells per second, at least 100 cells per second, at least 1000 cells per second, at least 2500 cells per second, at least 5000 cells per second, at least 10 cells per second per detection channel, at least 100 cells per second per detection channel, at least 1000 cells per second per detection channel, at least 2500 cells per second per detection channel, or at least 5000 cells per second per detection channel.

Data Processing

The apparatuses and methods described herein can include a digital processing device, or use of the same. The digital processing device can include one or more hardware central processing units (CPU) that carry out the device's functions. The digital processing device can further comprise an operating system configured to perform executable instructions. In some embodiments, the digital processing device is optionally connected to a computer network, is optionally connected to the Internet such that it accesses the World Wide Web, or is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices can include, by way of non-limiting examples, server computers, desktop computers, and portable computing devices. The digital processing device can include an operating system configured to perform executable instructions. The operating system can be, for example, software, including programs and data, which can manage the device's hardware and provides services for execution of applications.

In some embodiments, the device can include a storage and/or memory device. The storage and/or memory device can be one or more physical apparatuses used to store data or programs on a temporary or permanent basis. In some embodiments, the device is volatile memory and requires power to maintain stored information. In other embodiments, the device is non-volatile memory and retains stored information when the digital processing device is not powered. The device can be a storage device including, by way of non-limiting examples, CD-ROMs, DVDs, flash memory devices, magnetic disk drives, magnetic tapes drives, optical disk drives, and cloud computing based storage. The storage and/or memory device can also be a combination of devices such as those disclosed herein.

The digital processing device can include a display to send visual information to a user. In some embodiments, the display comprises a touch screen. The digital processing device can also include an input device to receive information from a user. For example, the input device can be a keyboard, a mouse, a touch screen, etc.

Non-Transitory Computer Readable Storage Medium

In some embodiments, the systems, apparatus, and methods disclosed herein can include one or more non-transitory computer readable storage media encoded with a program including instructions executable by the operating system of an optionally networked digital processing device. A computer readable storage medium can include, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

The systems, apparatus, and methods disclosed herein can include at least one computer program, or use of the same. A computer program includes a sequence of instructions, executable in the digital processing device's CPU, written to perform a specified task. In some embodiments, computer readable instructions are implemented as program modules, such as functions, objects, Application Programming Interfaces (APIs), data structures, and the like, that perform particular tasks or implement particular abstract data types. In light of the disclosure provided herein, those of skill in the art will recognize that a computer program, in certain embodiments, is written in various versions of various languages.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed.

In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 aL" means "about 5 aL" and also "5 aL." Generally, the term "about" includes an amount that would be expected to be within experimental error.

The section headings used herein are for organizational purposes only and are not to be construed as limiting the subject matter described.

EXAMPLES

The following examples are included to further describe some aspects of the present disclosure, and should not be used to limit the scope of the invention.

Example 1

Fixing and Labeling of Cells on a Substrate

This example describes fixing and ultrafast labeling of cells with a detectable agent, as described in FIG. 1 and FIG. 2 and illustrated in FIG. 4.

MCF-7 cells were seeded onto a petri dish in Eagle's minimum essential medium (with L-glutamine) supplemented with 10% fetal bovine serum and 1% penicillin (50 U ml$^{-1}$)-streptomycin (5 μg ml$^{-1}$) at 37° C. and 5% CO$_2$ and allowed grow until 80% confluent. Cells were then washed with PBS and fixed with 4% paraformaldehyde/PBS for 15 minutes at room temperature before being washed three times with PBS. Cells were heated to 37° C. (as in step 102 of FIG. 1), and 1 μg/ml PE-anti-human CD326 (EpCAM) antibody was applied to the cells (as in step 103 of FIG. 1). After washing away free PE-conjugated antibodies, labeled cells were detected using a fluorescent microscope (Nikon Eclipse TE2000) with a Xe lamp source under ambient conditions (as in step 106 of FIG. 1). The fluorescence signal was filtered by a 556-nm long-pass and a 585/42 nm band-pass filter, and images of PE-stained cells were recorded and analyzed using the computer software suite.

Ultrafast labeling of fixed MCF-7 cells for 5 minutes resulted in an average brightness of more than 6 times the average brightness of cells labeled using conventional labeling protocols (e.g., labeling at room temperature, that is, around 24° C., using 1:10 detectable agent dilution relative to ultrafast labeling protocol). FIG. 9G shows signal intensity of cells labeled using ultrafast labeling (e.g., 10×, 37° C., 5 min) with flow cytometry, and indicates that the ultrafast labeling method results in highly efficient labeling as evident from the high positive fluorescence intensity exhibited by the cells in flow cytometry. At the same time, ultrafast labeling maintains low non-specific binding that is comparable to that obtained with the normal labeling methods.

Example 2

De-Labeling a Cell with an Applied Voltage

This example describes ultrafast de-labeling of cells using an applied voltage, as described in FIG. 3 and illustrated in FIGS. 10A-10H, FIGS. 11A-11D, FIGS. 12A-12C, FIGS. 13A-13T, FIGS. 14A-14F, and FIGS. 15A-15C.

MCF-7 cells cultured to 80% confluence in a petri dish and labeled with PE-anti-EpCAM as in Example 1 were oriented such that the substrate was between a pair of platinum electrodes, capable of generating a voltage and emitting an electric field and in contact with the 1×PBS (pH 7.3) solution in which the cell was bathed, and placed on either side of the substrate or fluidic inlet and outlet (301). One of the electrodes was connected to a power supply and the other was connected to a grounded wire, thus forming an electrical circuit. The solution in contact with the cells on the substrate was exposed to a voltage of 8 volts for 60 seconds (302). The power supply was de-energized; optionally, and to verify de-labeling of detectable agents, the substrate with the de-labeled cells were moved into position on a fluorescent microscope with a Xe lamp source under ambient conditions for imaging. Cells were imaged and analyzed as in Example 1 to verify that detectable agent signal had been decreased by 99% (303).

Ultrafast de-labeling at 8 volts decreased detectable agent signal intensity to less than 10% of the signal from samples that had not been de-labeled after 60 seconds (see FIG. 11C and FIG. 11D) and to less than 1% of the signal from samples that had not be de-labeled after 90 seconds (see FIG. 11C and FIG. 11D).

Example 3

Non-Specific Binding of Ultrafast Labeling

This example describes the non-specific binding of ultrafast labeling, as shown in FIGS. 17A-17D.

Ultrafast and normal labeling methods were performed on B-cell and B-cell/T-cell mixture to assess non-specific background signal resulting from ultrafast labeling as compared to normal labeling. Cells labeled using normal labeling methods were treated with 0.125 μg/mL anti-CD28 PE-antibody at room temperature for 5 minutes. Cells labeled with ultrafast labeling methods were treated with 1.25 μg/mL anti-CD28 PE-antibody at 37° C. for 5 minutes. Cells were then imaged using a Nikon Eclipse TE2000 fluorescent microscope with a lamp source under ambient conditions. The signals detected from the samples were filtered with a 556-nm long-pass and a 585/42 nm band-pass filter, and images of PE-stained cells were recorded and analyzed using the computer software suite.

Results show that non-specific staining of B-cells was minimal and comparable for normal and ultrafast labeling methods (see FIGS. 17A-17D, compare FIG. 17A and FIG. 17B with FIG. 17C, and FIG. 17D), both in B-cell only suspension and the B-cell/T-cell mixed suspension. Note that B-cells do not express the protein for binding to PE-antibody, and thus serves as the negative control and for determining the level of non-specific staining; T-cells express the protein for binding PE-antibody, and thus serve as the positive control. Insets of FIG. 17A and FIG. 17C represent post-processing of images in which the gain of the image was increased by the same amount in silico to illustrate the presence of cells. Thus, non-specific background staining (e.g., non-specific detectable agent signal) was found to be minimal in cells stained with ultrafast labeling methods.

Example 4

De-Labeling a Cell with a Black Hole Quencher

This example describes ultrafast de-labeling of labeled cells using a detectable agent signal quencher, as shown in FIG. 19A-19D.

Figures 19A, 19B, 19C, 19D:
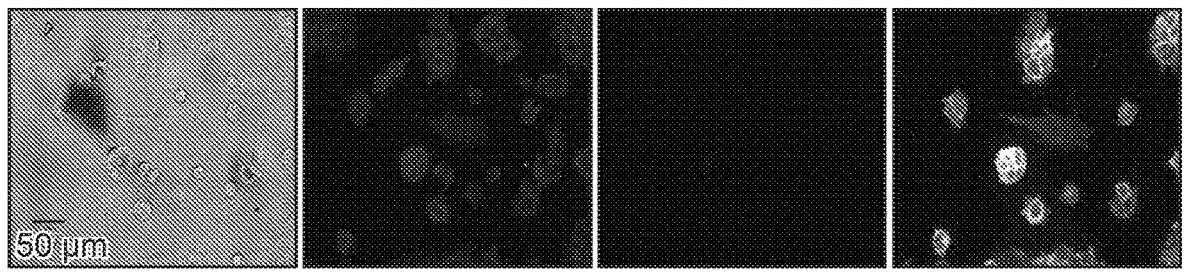
FIGS. 19A-19D show cyclic ultrafast labeling, involving de-labeling with Black Hole Quencher.

Cells were labeled as in Example 1, with the exception that streptavidin-conjugated polymer dot antibodies were used as the detectable agent instead of PE-anti-EpCAM. Polymer dots conjugated with streptavidin were used at a final concentration of 5 ppm. The cells were labeled with biotinylated anti-EpCAM prior to contact with streptavidin-conjugated polymer dots. FIG. 19A and FIG. 19B show bright field and fluorescent images, respectively, of the cells after labeling with biotin-anti-EpCAM and streptavidin-polymer dots. BHQ2-NH2 Black Hole Quencher, a broad absorption spectrum quencher centering around 600 nm with a quenching reaction at a distance of approximately 2 nm, was prepared in DMSO at 2 mM stock concentration and diluted with 1×PBS (pH 7.3) to a final concentration of 60 μM before being applied to the cells for 90 seconds. Cells were washed with 1×PBS and, optionally, were imaged (as in Example 2 and FIG. 3, step 303) to verify that detectable agent signal had been decreased by 95% (see FIG. 19C). Cells were then re-stained using PE-anti-EpCAM (see FIG. 19D).

Example 5

Ultrafast Labeling and De-Labeling of a Cell

This example describes ultrafast labeling, detection, and de-labeling of cells, as described in FIG. 4 and as illustrated in FIGS. 20A-20I.

MCF-7 cells were seeded onto a petri dish in Eagle's minimum essential medium (with L-glutamine) supplemented with 10% fetal bovine serum and 1% penicillin (50 U ml$^{-1}$)-streptomycin (5 µg ml$^{-1}$) at 37° C. and 5% CO$_2$ and allowed grow until 80% confluent. Cells were then washed with PBS and fixed with 4% paraformaldehyde/PBS for 15 minutes at room temperature before being washed three times with PBS. Cells were heated to 37° C. (as in step 402 of FIG. 4) before being contacted with PE-anti-cytokeratine at a concentration of 1 µg/ml for 5 minutes (see step 403), using similar experimental labeling conditions as in Example 1. Cells were then imaged using a fluorescent microscope with a Xe lamp source under ambient conditions (404). The signal detected from the sample was filtered with a 556-nm long-pass and a 585/42 nm band-pass filter, and images of PE-stained cells were recorded and analyzed using the computer software suite. Representative results from labeling can be seen in FIG. 20A (upper panel, bright field; lower panel, fluorescence detection). Cells were then subjected to a voltage of 8 volts in strength for 5 minutes (step 405). After this, cells were imaged again to confirm de-labeling of detectable agents (step 406 and FIG. 20B).

Example 6

Ultrafast Cyclic Labeling and De-Labeling of a Cell

This example describes iterative, cyclic labeling, detection, and de-labeling of cells, as described in FIG. 4 and as illustrated in FIGS. 20A-20I.

The advantages of applying ultrafast labeling and de-labeling methods cyclically in a protocol to label, de-label, and re-label MCF-7 cells was assayed. Ultrafast labeling methods, as described in Example 5, were used to label and to image a cell with 1 µg/ml PE-anti-cytokeratine. The cell was then subjected to ultrafast de-labeling, as described in Example 5 before ultrafast labeling and de-labeling steps were repeated four more times (FIG. 20C-FIG. 20I).

Figure 20A:
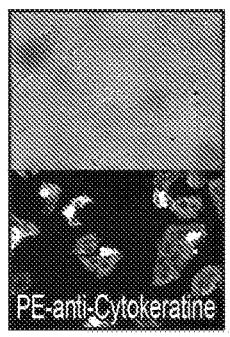
FIGS. 20A-20I show images of five cycles of ultrafast cyclic fluorescence imaging, using five different detectable agents (PE-anti-cytokeratine, PE-anti-MUC1, PE-anti-HER2, PE antiEpCAM,and PE-anti-EGFR) and 5 minutes of de-labeling at 8V between labeling steps, according to embodiments of the present disclosure. The top half of each image depicts the brightfield images of the cells and the bottom half depicts the fluorescence imaging of the cells.
Figure 20B:
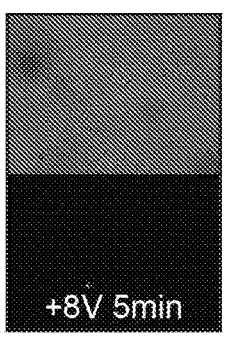
Figure 20C:
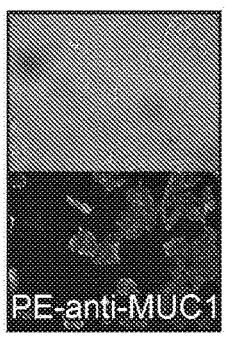
Figure 20D:
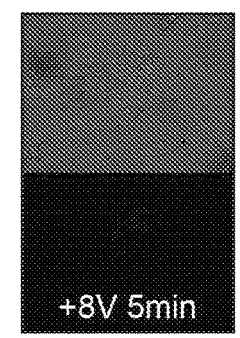
Figure 20E:
Figure 20F:
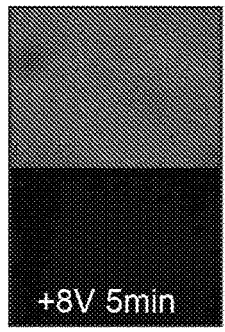
Figure 20G:
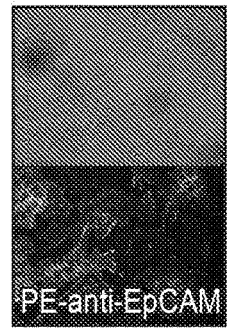
Figure 20H:
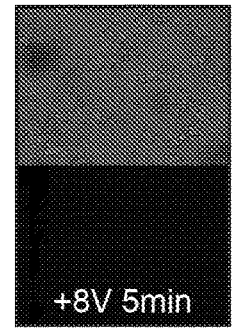
Figure 20I:
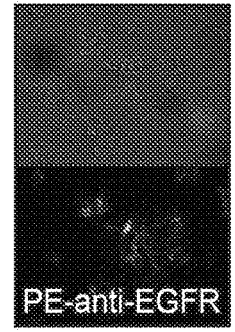
Figure 21A:
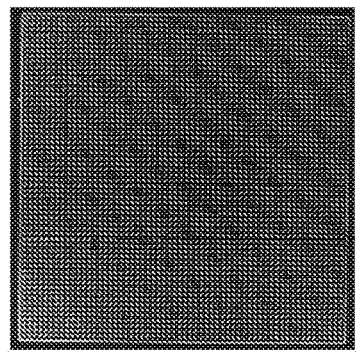
FIGS. 21A-21G show single-cell arrays for cyclic fluorescence single-cell labeling. Single-cell arrays can be generated in different densities and sizes (FIGS. 21A-21F), depending on the design and microfabrication of the array.
Figure 21B:
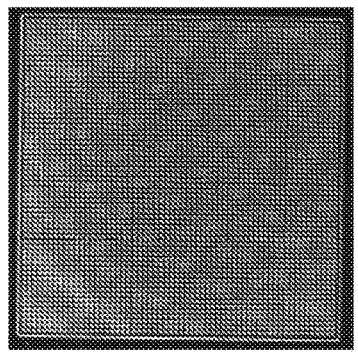
Figure 21C:
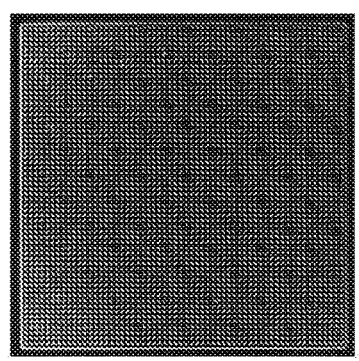
Figure 21D:
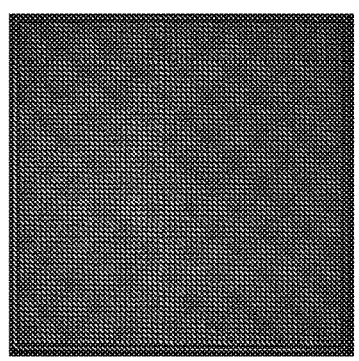
Figure 21E:
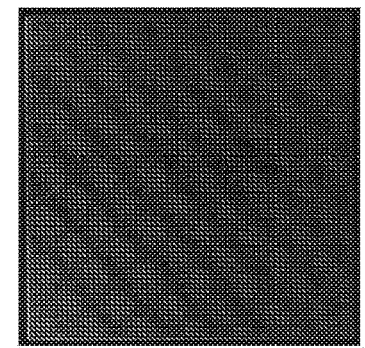
Figure 21F:
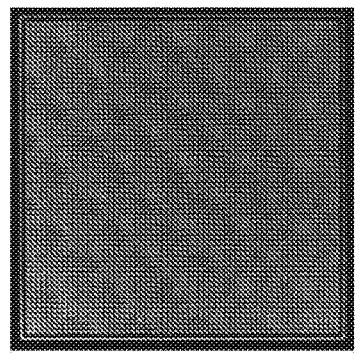
Figure 21G:
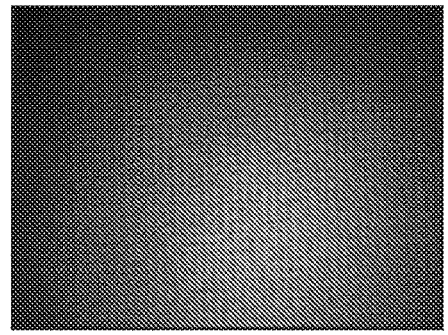
Figure 22A:
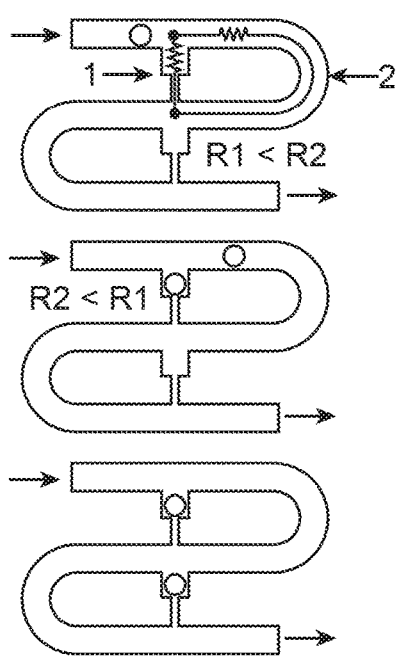
FIGS. 22A-22C show examples of single-cell arrays according to an aspect of the present disclosure.
Figure 22B:
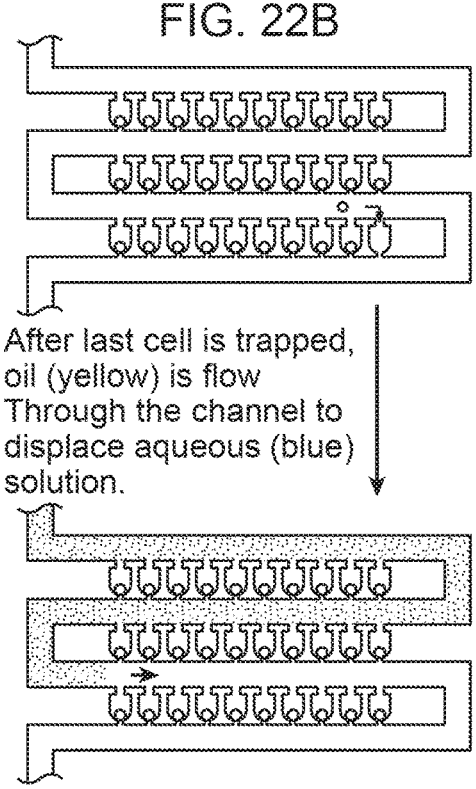
Figure 22C:
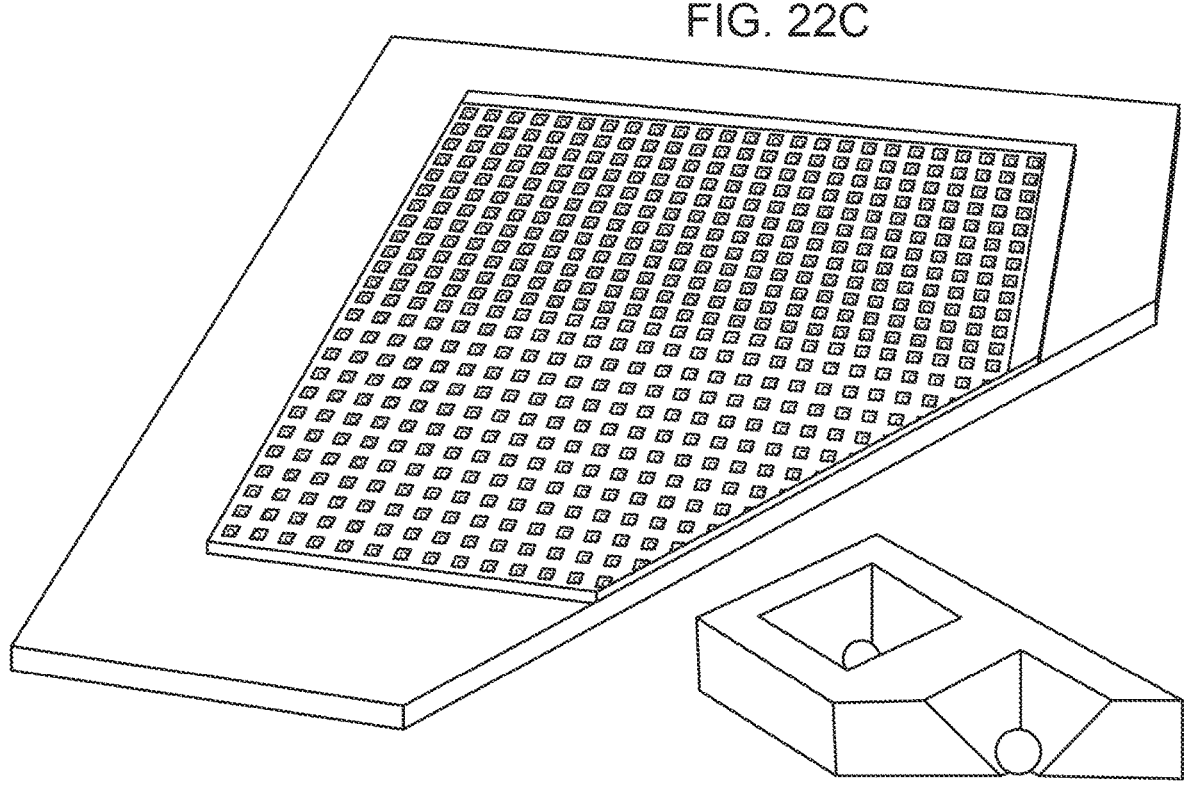

That is, cells were fixed for 15 minutes with 4% paraformaldehyde/PBS at room temperature, washed, heated, and contacted with PE-anti-cytokeratine according to the methods described in Example 5, prior to being imaged on a microscope (FIG. 20A). Cells were then exposed to a voltage of 8 volts for 5 minutes (similarly to the methods of Example 5) to de-label the cells, and the cells were imaged to confirm de-labeling (FIG. 20B). The cells were then labeled once again using 1 µg/ml PE-anti-MUC1 antibody and identical conditions as in the first round of labeling (e.g., the sample was brought to a temperature of 37° C. and labeled for 5 minutes). The sample was then imaged using the same settings as were used for PE-anti-cytokeratine detection (FIG. 20C) before the sample was de-labeled and imaged (FIG. 20D). The processes of de-labeling, labeling, and detecting were repeated to label (FIG. 20E) and de-label (FIG. 20F) the same sample with PE-anti-HER2, to label (FIG. 20G) and de-label (FIG. 20H) the same sample with PE-anti-EpCAM, and to label (FIG. 20I) the same sample with PE-anti-EGFR. Experimental results showed that the process of labeling, detecting, and de-labeling a cell with respect to detectable agents could be accomplished in 10-15 minutes or less, suggesting that sequential labeling and de-labeling of cells could be made significantly more cost effective and significantly less time- and effort-intensive.

Example 7

Multiplexed Ultrafast Cyclic Fluorescent Imaging of a Cell

This example describes automated, multiplexed ultrafast labeling, detection, and de-labeling of cells, as described above and in FIG. 4 and FIGS. 20A-20I.

Cells are subjected to multiplexed ultrafast cyclic fluorescent imaging by placing a stack of substrates containing cells of interest into an analyzer tray connected to a fluorescent microscope (which comprises an epi-fluorescence microscope with a blue LED (centered around 480 nm emission wavelength) and shutters and an optical detector equipped with 556-nm long-pass and 585/42 nm band-pass filters), a voltage or electrical field source (which is connected to a power supply), a heating element connected to a thermocouple such that both can be placed in contact with the substrate, and a microfluidic system, which comprised a peristaltic pump, a reagent reservoirs for fixatives, buffers, and each detectable agent, a waste fluid reservoir, and a plurality of fluid channels and valves connecting the substrate, the pump, and the reservoirs. Parameters that include the desired quantity of detectable agent to apply per cycle, detectable agent excitation source, time of contact between detectable agent and sample, detection methods (e.g., wells of the substrate to be analyzed, exposure time of cells to light excitation, the integration time of the detector, the position of the filter, etc.), and the number of rounds of labeling and de-labeling are input into the computer through a user interface. Upon user initiation, the computer executes a program that engages the microfluidic device to deliver 20 µl of 4% paraformaldehyde/PBS and 0.25% Triton X-100 (a cell permeabilization agent) from one of the fluid reservoirs to the cells on the substrate. After 15 minutes, the computer commands the microfluidic device to remove the paraformaldehyde to the waste reservoir and to deliver wash buffer containing 20 µl of 150 µM BlockAid™ to the substrate for 5 minutes. The computer processor then automatically initiates the heating element (and negative feedback loop involving the thermocouple) to heat the cells on a substrate to 37° C. then employs the microfluidic system to deliver 20 µl of PBS containing 1 µg/ml of PE-anti-EpCAM, 1 µg/ml of APC-anti-cytokeratine, 1 µg/ml of FITC-anti-MUC1, 1 µg/ml of AlexaFluor594-anti-HER2, and 1 µg/ml of PE-Cy7-anti-EGFR to the cells on the substrate. The detectable agent is allowed to contact the cells for 5 minutes before the supernatant containing the detectable agent is removed via the microfluidic device to the waste reservoir upon a command from the computer processor. The cells are imaged using the fluorescent microscope. The differently-colored antibodies were imaged by using different filter cubes, as dictated by the program executed by the computer processor. The substrate is then moved by the system's sample tray gear mechanism to an electrically-shielded region of the apparatus, housing the voltage source and exposed to a voltage of 8 volts for 60 seconds. As this is occurring, a second substrate is moved into position and labeled for 5 minutes using the same method as was used for labeling the first substrate. As the cells on other substrates are being imaged or de-labeled, the first substrate is labeled with a second set of detectable agents (1 µg/ml of PE-anti-E-Cadherin, 1 µg/ml of APC-CD49d, 1 µg/ml of PE-Cy7-anti-CD11b, 1 µg/ml of AlexaFluor594-anti-ckit, 1 µg/ml of FITC-anti-EpCAM, 1 µg/ml of BODIPY R6G-anti-CD68, 1 µg/ml of Cy5.5-APC-anti-CD45) and imaged again. When a system capable of simultaneous labeling of a first sample and de-labeling of a second sample is unavailable, labeling and de-labeling steps are performed consecutively for a single sample, without simultaneous processing of a second sample. The process is continued in this manner until all cells on all substrates have been labeled and detected with all detectable agents required for the experiment.

When de-labeling of multiply-labeled cells requires a quenching agent to de-label one detectable agent that has been used to label the cell, the step of the ultrafast cyclic labeling protocol requiring the detectable agent is defined by the user via the user interface before the program is initiated by the computer processor, and the processor commands the flow cell to deliver the quenching agent from the appropriate reagent reservoir to the appropriate substrate (e.g., the appropriate well of the substrate) at the appropriate step.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 8

De-Labeling of a Cell Under Continuous Fluidic Flow

Figure 14A:
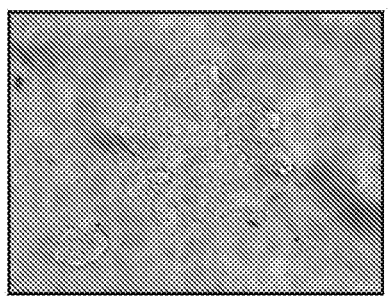
FIGS. 14A-14F show de-labeling of MCF-7 cells under a continuous flow of buffer (FIGS. 14A-14C), and under a controlled and timed application of buffer flow (FIGS. 14D-14F).
Figure 14B:
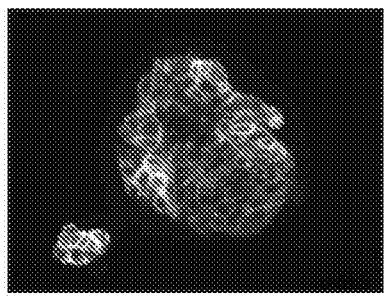
Figure 14C:
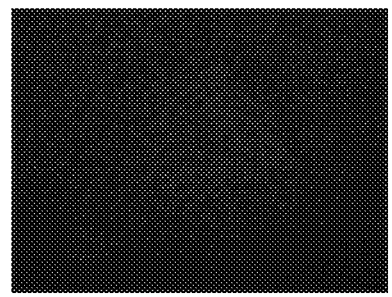
Figure 14D:
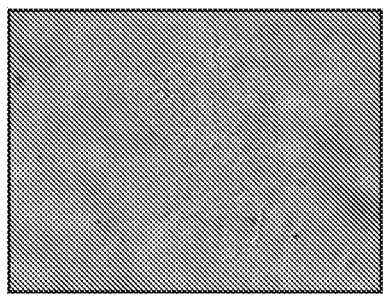
Figure 14E:
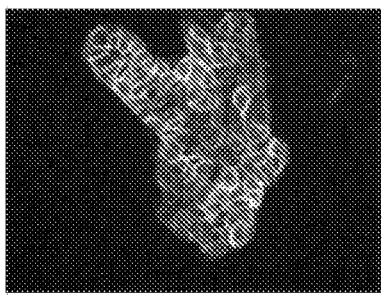
Figure 14F:
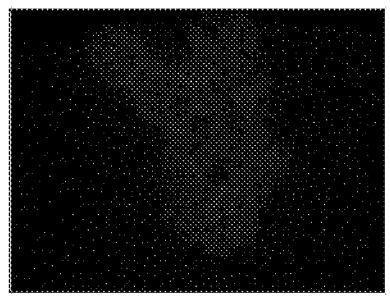

This example describes de-labeling of cells under continuous flow of a fluid, as described in FIG. 14A-FIG. 14C.

MCF-7 cells were seeded onto a petri dish in Eagle's minimum essential medium (with L-glutamine) supplemented with 10% fetal bovine serum and 1% penicillin (50 U ml$^{-1}$)-streptomycin (5 μg ml$^{-1}$) at 37° C. and 5% CO$_2$ and allowed grow until 80% confluent. Cells were then washed with PBS and fixed with 4% paraformaldehyde/PBS for 15 minutes at room temperature before being washed three times with PBS. Cells were heated to 37° C. (as in step 102 of FIG. 1), and 1 μg/ml PE-anti-human CD326 (EpCAM) antibody was applied to the cells (as in step 103 of FIG. 1). After washing away free PE-conjugated antibodies, labeled cells were detected using a fluorescent microscope (Nikon Eclipse TE2000) with a Xe lamp source under ambient conditions (as in step 106 of FIG. 1). The fluorescence signal was filtered by a 556-nm long-pass and a 585/42 nm band-pass filter, and images of PE-stained cells were recorded and analyzed using the computer software suite (FIG. 14B).

PE-anti EpCAM labeled MCF-7 cells were then subjected to a voltage of 5V in strength for 180 seconds and a continuous flow of buffer was applied into the channel. FIG. 14C shows that MCF-7 cells were de-labeled with high efficiency.

Example 9

De-Labeling of a Cell Under Controlled and Timed Fluidic Flow

This example describes de-labeling of cells under controlled and timed flow of a fluid, as described in FIG. 14D-FIG. 14F.

MCF-7 cells were seeded onto a petri dish in Eagle's minimum essential medium (with L-glutamine) supplemented with 10% fetal bovine serum and 1% penicillin (50 U ml$^{-1}$)-streptomycin (5 μg ml$^{-1}$) at 37° C. and 5% CO$_2$ and allowed grow until 80% confluent. Cells were then washed with PBS and fixed with 4% paraformaldehyde/PBS for 15 minutes at room temperature before being washed three times with PBS. Cells were heated to 37° C. (as in step 102 of FIG. 1), and 1 μg/ml PE-anti-human CD326 (EpCAM) antibody was applied to the cells (as in step 103 of FIG. 1). After washing away free PE-conjugated antibodies, labeled cells were detected using a fluorescent microscope (Nikon Eclipse TE2000) with a Xe lamp source under ambient conditions (as in step 106 of FIG. 1). The fluorescence signal was filtered by a 556-nm long-pass and a 585/42 nm band-pass filter, and images of PE-stained cells were recorded and analyzed using the computer software suite (FIG. 14E).

PE-anti EpCAM labeled MCF-7 cells were then subjected to a voltage of 4V in strength for 180 seconds and a controlled and timed application of buffer into the channel. FIG. 14F shows that MCF-7 cells were de-labeled with high efficacy.

Example 10

Labeling and De-Labeling of Cells without Epitope Damage

Figure 15A:
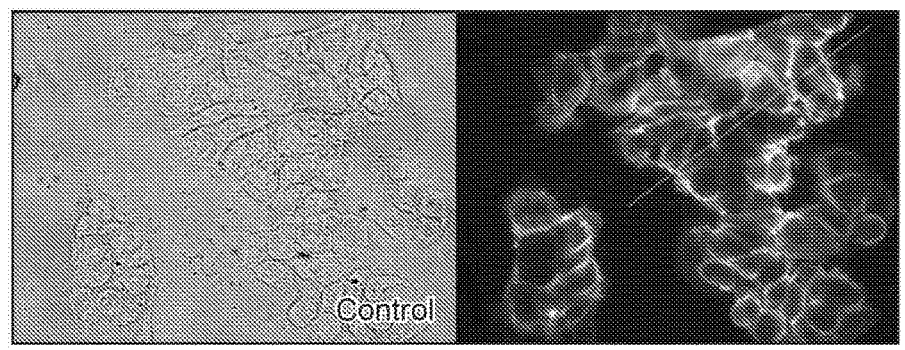
FIGS. 15A-15C show no noticeable differences in brightness between control cells (FIG. 15A) and cells after nine cycles (4 volts for 3 min each) of de-labeling (FIG. 15B), demonstrating that at least nine cycles of labeling and de-labeling can be performed without any noticeable epitope damage on the cells. Brightness profiles along the lines in FIG. 15A and FIG. 15B also demonstrated no noticeable difference between the brightness levels of the two representative images as shown in FIG. 15C, thus indicating no noticeable epitope damage.
Figure 15B:
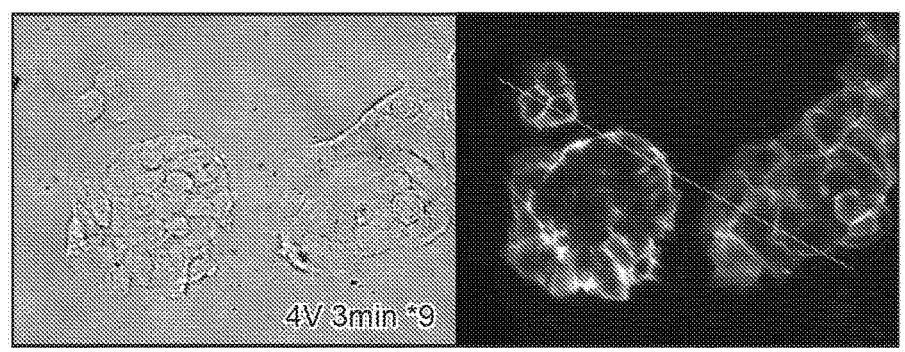
Figure 15C:
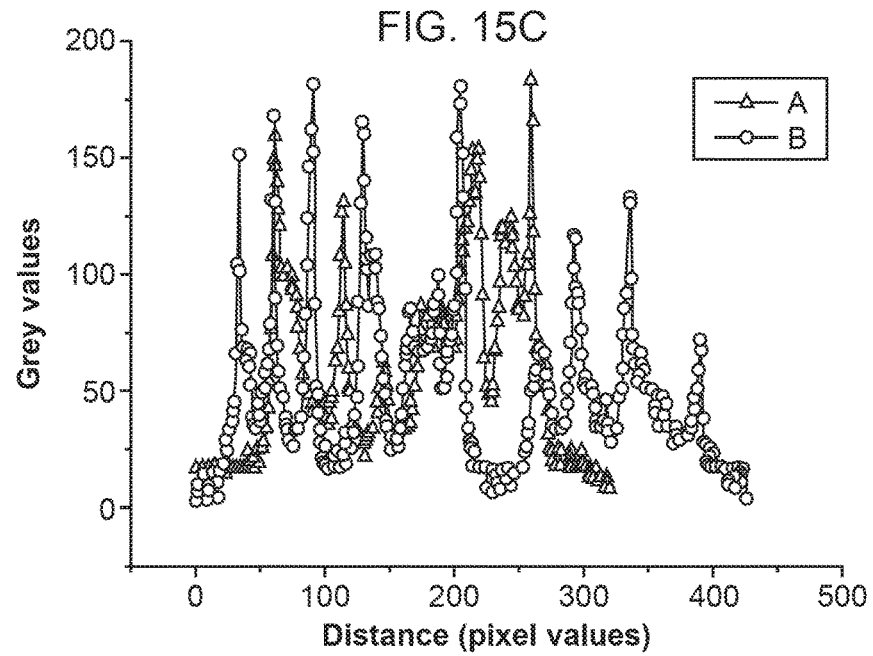

This example describes the labeling and de-labeling of cells in 9 cycles without noticeable epitope damage, as illustrated in FIG. 15A-FIG. 15C. This example demonstrates the ability to carry out at least 9 cycles of labeling and de-labeling (i.e., 10 cycles of imaging) without inducing noticeable epitope damage on the cells.

MCF-7 cells were seeded onto a petri dish in Eagle's minimum essential medium (with L-glutamine) supplemented with 10% fetal bovine serum and 1% penicillin (50 U ml$^{-1}$)-streptomycin (5 μg ml$^{-1}$) at 37° C. and 5% CO$_2$ and allowed grow until 80% confluent. Cells were then washed with PBS and fixed with 4% paraformaldehyde/PBS for 15 minutes at room temperature before being washed three times with PBS. Cells were heated to 37° C. (as in step 102 of FIG. 1), and 0.1 μg/ml PE-anti-human CD326 (EpCAM) antibody was applied to the cells (as in step 103 of FIG. 1). After washing away free PE-conjugated antibodies, labeled cells were detected using a fluorescent microscope (Nikon Eclipse TE2000) with a Xe lamp source under ambient conditions (as in step 106 of FIG. 1). The fluorescence signal was filtered by a 556-nm long-pass and a 585/42 nm band-pass filter, and images of PE-stained cells were recorded and analyzed using the computer software suite (FIG. 15B).

MCF-7 cells were subjected to 9 cycles of de-labeling (4V for 3 minutes each, after which the cells were labeled with 0.1 μg/ml PE-anti EpCAM antibody). Brightfield images and fluorescent microscopy, as shown in FIG. 15B, showed no significant difference in brightness when compared to the control (no voltage application) shown in FIG. 15A, thus indicating no noticeable epitope damage on the cells.

Brightness profiles along the lines in FIG. 15A and FIG. 15B also demonstrated no noticeable difference between the brightness levels of the two representative images (FIG. 15C), thus indicating no noticeable epitope damage.

Example 11

Generation of Single-Cell Arrays for Cyclic Fluorescence Single-Cell Imaging

This example describes the generation of single-cell arrays for use with a method of labeling and de-labeling a cell, as illustrated in FIG. 21. This example demonstrates the preparation and use of single-cell arrays for cyclic fluorescence single-cell imaging.

A glass substrate is first coated with a layer that resists the absorption of cells, such as a PEG (polyethylene glycol) coating. After application of this coating, a patterning technique is used to create an array of patches, where a single cell is strongly attached to each patch (i.e., one cell per patch). This array of patches, created in a background of a coating that resist absorption of cells, can be generated using a wide range of established methods, such as photolithography (as used in FIG. 21) or soft lithography as described in the art. The surface of the patches to which single cells attach also can be selected from a wide range of surface chemistries, such as APTES (3-aminopropyl triethoxysilane) (as used in FIG. 21) or poly-L-lysine.

Instead of coating the surface with a layer (e.g., PEG) that resists cell absorption, then patterning the "sticky" patches to which individual cells attach, it can also be efficient to first pattern "sticky" patches for cell attachment on glass, after which a layer of surface chemistry that resists cell absorption is applied to cover the areas unoccupied by the "sticky" patches. Several methods are available to achieve this goal including attaching the PEG molecules to the exposed Si—OH groups (that are not covered by the "sticky" patches).

Additionally, the "sticky" patches can be a flat surface, or can be recessed (e.g., like a well), depending on both the need of the application, as well as the microfabrication method. Recessed patches can be readily created using tools of microfabrication and patterned surface chemistry known in the art, and offers the advantage of further protecting the cells from detachment caused by fluid flow.

What is claimed is:

1. A method of labeling and de-labeling a cell, the method comprising:
   providing a cell associated with a substrate;
   contacting the cell with a detectable agent thereby labeling a plurality of sites of the cell with the detectable agent, wherein the plurality of detecable agents comprises a fluoorescent detectable agent; and
   applying a voltage with one or more electrodes to a solution in contact with the cell, wherein applying the voltage generates one or more reactive chemical species, thereby quenching or removing a fluoresnce singal from the fluoreescent detecable agent and de-labeling the cell, wherein at least 90% of the plurality of sites of the cell are de-labeled.

2. A method of claim 1, wherein applying voltage to the solution in contact with the cell generates one or more reactive chemical species.

3. The method of claim 1, further comprising detecting the plurality of detecable agents after labeling the plurality of sites, wherein the detecting comprises optically detecting the plurality of detecable agents.

4. The method of claim 1, wherein the labeling de-labeling is performed in less then 20 minutes, less than 15 minutes, less than 10 minutes, less than 9 minutes, less than 8 minutes, less than 7 minutes, less then 5 minutes, less than 4 minutes, or less than 3 minutes.

5. The method of claim 1, wherein the method is repeated for at least 2 times, at least 3 times, at least 4 times, at least 5 times, at least 10 times, at least 50 times.

6. The method of claim 1, further comprising imaging the cell labeled with the plurality of detecable agents.

7. The method of claim 1, wherein a portion of the plurality of sites of the cell are labeled, the portion being at least 25%, at least 25%, at least 50%, at least 60%, at least 70%, at least 75%, at least 80%, at least 90%, or at least 95%, and wherein the portion of the plurality of sites of the cell are labeled with the plurality of detectable agents in a time of not more than 15 minutes, not more than 10 minutes, not more than 7.5 minutes not more than 5 minutes, not more than 4 minutes, not more than 3 minutes, not more than 2 minutes, or not more than 1 minute.

8. The method of claim 1, wherein the saturation of the plurality of detectable agents on the cell is more than 25%, more than 50%, more than 75%, or more than 90% of the saturation as compared to a second cell labeled under the same conditions, except that the labeling of the second cell is performed at 20° C. for 1 hour.

9. The method of claim 1, wherein the voltage applied to the solution in contact with the cell is 1 V to 100 V, 1 V to 50 V, 1 V to 25 V, or 5 V to 15 V, or at least 8 V.

10. The method of claim 1, wherein a continuous flow, an intermittent flow, a timed flow, or a controlled flow of the solution, or a combination thereof, is applied to the labeled cells.

11. The method of claim 1, wherein at least 90% of the plurality of sites are de-labeled in a time of less than 15 minutes, less than 10 minutes, less than 6 minutes, less than 5 minutes, less than 4 minutes, or less than 3 minutes, less than 2 minutes, less than 1 minute, or less than 30 seconds.

12. The method of claim 1, wherein de-labelling the cell further comprises contacting the labeled cell with a quenching agent.

13. The method of claim 1, wherein the plurality of detectable agents is covalently attached to an affinity tag, wherein the affinity tag is selected from the group consisting of an aptamer, an antibody, and a nucleic acid.

14. The method of claim 1 further comprising illuminating the cell with light configured to excite the fluorescent detectable agent.

15. A method of labeling and de-labelling a cell, the method comprising:
   providing a cell associated with a substrate;
   heating the cell to a controlled temperature;
   delivering a plurality of detectable agents to the cell using a flow cell, thereby contacting the cell with the plurality of detectable agents and labeling a plurality of sites of the cell with the plurality of detectable agents, wherein the plurality of detectable agents comprises a fluorescent detectable agent; and
   applying a voltage with one or more electrodes to a solution in contact with the cell, wherein applying the voltage generates one or more reactive chemical species, thereby quenching or removing a fluorescence signal from the fluorescent detectable agent and de-labeling the cell, wherein at least 90% of the plurality of sites of the cell are de-labeled.

16. A method of de-labeling a labeled cell, the method comprising:
   providing a cell associated with a substrate, wherein a plurality of sites of the cell is labeled with a plurality of detectable agents, wherein the plurality of detectable agents comprises a fluorescent detectable agent;

applying a voltage with one or more electrodes to a solution in contact with the cell, wherein applying the voltage generates one or more reactive chemical species, thereby quenching or removing a fluorescence signal from the fluorescent detectable agent and de-labeling at least 75% of the plurality of sites on the labeled cell in less than 15 minutes.

\* \* \* \* \*

UNITED STATES PATENT AND TRADEMARK OFFICE
CERTIFICATE OF CORRECTION

PATENT NO. : 11,668,713 B2  Page 1 of 1
APPLICATION NO. : 16/347502
DATED : June 6, 2023
INVENTOR(S) : Daniel T. Chiu et al.

It is certified that error appears in the above-identified patent and that said Letters Patent is hereby corrected as shown below:

In the Claims

| Column | Line | |
|---|---|---|
| 51 | 45 | Claim 1, delete "a detectable agent" and insert -- a plurality of detectable agents -- |
| 51 | 46-47 | Claim 1, delete "the detectable agent," and insert -- the plurality of detectable agents, -- |
| 51 | 47 | Claim 1, delete "detecable" and insert -- detectable -- |
| 51 | 48 | Claim 1, delete "fluoorescent" and insert -- fluorescent -- |
| 51 | 52 | Claim 1, delete "fluoresnce singal" and insert -- fluorescence signal -- |
| 51 | 53 | Claim 1, delete "fluoreescent detecable" and insert -- fluorescent detectable -- |
| 51 | 56 | Claim 2, delete "A method" and insert -- The method -- |
| 51 | 60 | Claim 3, delete "detecable" and insert -- detectable -- |
| 51 | 62 | Claim 3, delete "detecable" and insert -- detectable -- |
| 51 | 63-64 | Claim 4, delete "labeling de-labeling" and insert -- labeling and de-labeling -- |
| 51 | 64 | Claim 4, delete "less then" and insert -- less than -- |
| 51 | 66 | Claim 4, delete "less then 5 minutes," and insert -- less than 6 minutes, less than 5 minutes, -- |
| 52 | 3 | Claim 5, delete "10 times," and insert -- 10 times, or -- |
| 52 | 5 | Claim 6, delete "detecable" and insert -- detectable -- |
| 52 | 8 | Claim 7, delete "least 25%, at least 25%," and insert -- least 25%, -- |
| 52 | 14 | Claim 7, delete "7.5 minutes" and insert -- 7.5 minutes, -- |
| 52 | 35 | Claim 12, delete "de-labelling" and insert -- de-labeling -- |
| 52 | 42 | Claim 14, delete "claim 1" and insert -- claim 1, -- |
| 52 | 45 | Claim 15, delete "de-labelling" and insert -- de-labeling -- |

Signed and Sealed this
Eleventh Day of March, 2025

Coke Morgan Stewart
*Acting Director of the United States Patent and Trademark Office*